(12) United States Patent
Clandinin et al.

(10) Patent No.: US 8,536,140 B2
(45) Date of Patent: Sep. 17, 2013

(54) METHODS FOR TREATING INFLAMMATORY BOWEL DISEASE

(75) Inventors: Michael Thomas Clandinin, Calmar (CA); Eek J. Park, San Diego, CA (US)

(73) Assignee: MTI Meta Tech Inc., Edmonton, Alberta (CA)

( * ) Notice: Subject to any disclaimer, the term of this patent is extended or adjusted under 35 U.S.C. 154(b) by 191 days.

(21) Appl. No.: 12/966,070

(22) Filed: Dec. 13, 2010

(65) Prior Publication Data

US 2011/0144041 A1 Jun. 16, 2011

Related U.S. Application Data

(63) Continuation-in-part of application No. 11/622,858, filed on Jan. 12, 2007, now Pat. No. 7,851,451, and a continuation-in-part of application No. 10/551,789, filed as application No. PCT/CA2004/000375 on Mar. 12, 2004, now Pat. No. 7,781,408.

(51) Int. Cl.
*A61K 31/7032* (2006.01)
*C07H 15/10* (2006.01)

(52) U.S. Cl.
CPC ............ *A61K 31/7032* (2013.01); *C07H 15/10* (2013.01)
USPC ........................................... 514/25; 536/17.9

(58) Field of Classification Search
None
See application file for complete search history.

(56) References Cited

U.S. PATENT DOCUMENTS

| | | | |
|---|---|---|---|
| 4,762,822 A | 8/1988 | Ettinger | |
| 5,190,925 A | 3/1993 | della Valle et al. | |
| 5,281,702 A | 1/1994 | Tubaro et al. | |
| 6,998,392 B2 | 2/2006 | Clandinin et al. | |
| 2004/0047856 A1 | 3/2004 | Williams et al. | |
| 2005/0107311 A1 | 5/2005 | Berger et al. | |
| 2007/0173480 A1 | 7/2007 | Clandinin et al. | |
| 2007/0238871 A1* | 10/2007 | Tsuji et al. ...................... | 536/53 |
| 2010/0136023 A1 | 6/2010 | Williams et al. | |

FOREIGN PATENT DOCUMENTS

| | | |
|---|---|---|
| EP | 0351784 | 7/1989 |
| EP | 1323424 A1 | 7/2003 |
| GB | 2289274 | 11/1995 |
| JP | 62145015 | 6/1987 |
| JP | 01163125 | 6/1989 |
| WO | WO 90/09185 | 8/1990 |
| WO | WO 95/20959 | 8/1995 |
| WO | WO 9605844 | 2/1996 |
| WO | WO 02/40051 | 5/2002 |
| WO | WO 0245740 | 6/2002 |
| WO | WO2010/065544 | * 6/2010 |

OTHER PUBLICATIONS

Alonso et al., "Dissociation of the Effects of the Antitumour Ether Lipid ET-18-OCH3 on Cytosolic Calcium and on Apoptosis", Brit. J. Pharmacol. 121 (1997) 1364-1368.
Anderson et al., "Essential Fatty Acid Deficiency and Renewal of Rod Outer Segments in the Albino Rat", Invest Ophthalmol. 15, 232-236 (1976).
Anderson, "The Caveolae Membrane System", Annual Review of Biochemistry; 1998;67:199-225.
Andersson et al., "Rates of Cholesterol, Ubiquinone, Dolichol and Doclichyl-P Biosynthesis in Rat Brain Slices", FEBS Lett 1990;269:15-8.
Asou et al., "Changes in Ganglioside Composition and Morphological Features During the Development of Cultured Astrocytes From Rat Brain", Neurosci. Res. 6 (1989) 369-375.
Aydin et al., "Age-Related Changes in GM1, GD1a, GT1b Components of Gangliosides in Wistar Albino Rats", Cell Biochem Funct 2000;18:41-5.
Barbour et al., "Glycolipid Depletion Using a Ceramide Analogue (PDMP) Alters Growth, Adhesion, and Membrane Lipid Organization in . . . ", J. Cell. Physiol. 150, 610-619 (1992).
Basavarajappa et al., "Activation of Arachidonic Acid-Specific Phospholipase A2 in Human Neuroblastoma Cells after . . . ", Clin. Exp. Res. 21 (1997) 1199-1203.
Bastiaanse et al., "The Effect of Membrane Cholesterol Content on Ion Transport Processes in Plasma Membranes", Cardiovasc Res 1997;33:272-83.
Bauldry et al., "Phospholipase A2 Activation in Human Neutrophils", J. Biol. Chem. 263 (1988) 16787-16795.
Bauldry et al., Differential Actions of Diacyl- and Alkylacylglycerols in Priming Phospholipase A2, 5-Lipoxygenase . . . , Biochim. Biophys. Acta 1084 (1991) 178-184.
Bavari et al., "Lipid Raft Microdomains: A Gateway for Compartmentalized Trafficking of Ebola and Marburg Viruses", J Exp Med 2002;195(5):593-602.
Belosevic et al., "*Giardia muris*: Correlation Between Oral Dosage, Course of Infection, and Trophozoite Distribution in the Mouse . . . ", 1983. Exp. Parasitol. 56:93-100.
Bernett et al., "Determination of Serum Phospholipid Metabolic Profiles by High-Performance Liquid Chromatography", J. Liq. Chromatogr. 8 (1985) 1573-1591.
Berger et al., "Nutritional Implications of Replacing Bovine Milk Fat With Vegetable Oil in Infant Formulas", J. Pediatr. Gastroenterol. Nutr. 30 (2000) 115-130.

(Continued)

*Primary Examiner* — Eric S Olson
(74) *Attorney, Agent, or Firm* — Robert M. Gould; Husch Blackwell LLP

(57) ABSTRACT

A method is described for treating inflammatory bowel disease in a subject in need thereof. The method comprises administering a formulation comprising at least one ganglioside to the subject, wherein the formulation comprises at least about 50% GD3 by weight of total ganglioside content.

29 Claims, 14 Drawing Sheets

(56) References Cited

OTHER PUBLICATIONS

Birch et al., "Visual Acuity and the Essentiality of Docosahexaenoic Acid and Arachidonic Acid in the Diet of Term Infants", Pediatr. Res. 44, 201-209 (1998).
Bittman et al., "Influence of Cholesterol on Bilayers of Ester-and Ether-Linked Phospholipis", Biochim. Biophys. Acta 772 (1984) 117-126.
Blank et al., "Meats and Fish Consumed in the American Diet Contain Substantial Amounts of Ether-Linked Phospholipids", J. Nutr. 122 (1992) 1656-1661.
Bouhours et al., "Developmental Changes of Hematoside of Rat Small Intestine", J. Biol. Chem. 258 (1983) 299-304.
Brown et al., "Sorting of GPI-Anchored Proteins to Glycolipid-Enriched Membrane Subdomains During Transport to the Apical Cell Surface", 1992. Cell. 68:533-544.
Brown et al., "Functions of Lipid Rafts in Biological Membranes", Annu Rev Cell Dev Biol 1998;14:111-36.
Buret et al., "Growth, Activities of Enzymes in the Small Intestine, and Ultrastructure of Microvillous Border in Gerbils . . . ", 1991. Parasitol Res. 77:109-114.
Byrne et al., "Ganglioside-Induced Neuritogenesis: Verification That Ganglioside Are the Active Agents, and Comparison of Molecular Species", J. Neurochem. 41 (1983) 1214-122.
Carlson, "N-Acetylneuraminic Acid Concentrations in Human Milk Oligosaccharides and Glycoproteins During Lactation", Am J Clin Nutr 1985;41:720-6.
Carlson et al., "Visual Acuity and Fatty Acid Status of Term Infants Fed Human Milk and Formulas With and Without Docosahexaenoate and . . . ", Pediatr. Res. 39, 882-888 (1996).
Carrie et al., "Docosahexaenoic Acid-Rich Phospholipid Supplementation", Nutr. Neurosci. 5, 43-52 (2002).
Chen et al., "Sphingomyelin Content of Intestinal Cell Membranes Regulates Cholesterol Absorption", Biochem J 1992;286 ( Pt 3):771-777.
Christiansen et al., "Microvillus Membrane Vesicles From Pig Small Intestine", Biochim. Biophys. Acta 647 (1981) 188-195.
Clandinin et al., "Effects of Methionine Supplementation on the Incidence of Dietary Fat Induced Myocardial Lesions in the Rat", J. Nutr. 110 (1980) 1197-203.
Clandinin et al., "Dietary Fat: Exogenous Determination of Membrane Structure and Cell Function", FASEB J 1991;5:2761-9.
Daniels et al., "Disaccharidase Activity in Male and Female C57BL/6 Mice Infected with *Giardia muris*", 1995. Parasitol Res. 81:143-147.
Danielsen et al., "A Transferrin-Like GPI-linked Iron-Binding Protein in Detergent-Insoluble Noncaveolar Microdomains at the Apical . . . Cells", J Cell Biol 1995; 131(4):939-50.
Danielsen, "Involvement of Detergent-Insoluble Complexes in the Intracellular Transport of Intestinal Brush Border Enzymes", Biochemistry 1995; 34(5):1596-1605.
Daniotti et al., "GD3 Ganglioside Is Prevalent in Fully Differentiated Neurons From Rat Retina", J. Neurosci. Res. 26, 436-446 (1990).
Daniotti et al., "Regulation of Ganglioside Composition and Synthesis is Different in Developing Chick Retinal Pigment Epithelium . . . ", J. Neurochem. 62 (1994) 1131-1136.
De Maria et al., "Requirement for GD3 Ganglioside in CD95- and Ceramide-Induced Apoptosis", Science 1997;277:1652-5.
Diamond et al., "A New Medium for the Axenic Cultivation of Entamoeba Histolytica and Other Entamoeba", 1978. Trans. R. Soc. Trop. Med. Hyg. 72:431-432.
Diomede et al., "Role of Cell Cholesterol in Modulating Antineoplastic Ether Lipid Uptake, Membrane Effects and Cytotoxicity", Int. J. Cancer 46 (1990) 341-346.
Diomede et al., "Fluorescence Polarization Changes with Gestational Age in Amniotic Fluid of Rabbit and Guinea Pig", Exp. Lung. Res. 16 (1990) 507-519.
Diomede et al., "Increased Ether Lipid Cytotoxicity by Reducing Membrane Cholesterol Content", Int. J. Cancer 49 (1991) 409-413.
Diomede et al., "Induction of Apoptosis in Human Leukemic Cells by the Ether Lipid 1-Octadecyl-2-Methyl-Rac-Glycero-3-Phosphocholine", Int. J. Cancer 53 (1993) 124-130.
Dreyfus et al., Simplified Ganglioside Composition of Photoreceptors Compared to Other Retinal Neurons, Invest Ophthalmol. Vis. Sci. 37, 574-585 (1996).
Dreyfus et al., "Ganglioside and Neurotrophic Growth Factor Interactions in Retinal Neuronal and Glial Cells", Indian J. Biochem. Biophys. 34, 90-96 (1997).
Faldella et al., "Visual Evoked Potentials and Dietary Long Chain Polyunsaturated Fatty Acids in Preterm Infants", Arch. Dis. Child. 75, F108-F112 (1996).
Fantini. "Synthetic Soluble Analogs of Glycolipids for Studies of Virus-Glycolipid Interactions", Sphingolipid Metabolism and Cell Signaling, Pt A 2000;311:626-38.
Farooqui et al., "Glycerophospholipids in Brain: Their Metabolism, Incorporation into Membranes, Functions . . . ", Chem. Phys. Lipids 106 (2000) 1-29.
Farthing. "Giardiasis", 1996. Gastro. Clin. North Am. 25:493-515.
Fielding et al., "Caveolin mRNA Levels are Up-Regulated by Free Cholesterol and Down-Regulated by . . . ", Proc Natl Acad Sci U S A 1997;94(8):3753-8.
Flickinger et al., "Localization of the Platelet-Activating Factor Receptor to Rat Pancreatic Microvascular Endothelial Cells", Am. J. Pathol. 1999;154(5):1353-8.
Folch et al., "A Simple Method for the Isolation and Purification of Total Lipides From Animal Tissues", 1957. J. Biol. Chem. 226:497-509.
Fontaine et al., "Changes in Ganglioside Composition of Photoreceptors During Postnatal Maturation of the Rat Retina", Glycobiology 8, 183-190 (1998).
Forstner et al., "Plasma Membrane and Mucosal Glycosphingolipids in the Rat Intestine", Biochim. Biophys. Acta 306 (1973) 446-459.
Fujito et al., "Promotion of Sprouting and Synaptogenesis of Cerebrofugal Fibers by Ganglioside Application in the Red Nucleus", Neurosci. Res. 2, 407-411 (1985).
Furuchi et al., "Cholesterol Depletion of Caveolae Causes Hyperactivation of Extracellular Signal-related Kinase (ERK)", J Biol Chem 1998;273:21099-21104.
Gatt et al., "Sphingomyelin Suppresses the Binding and Utilization of Low Density Lipoproteins by Skin Fibroblasts", J Biol Chem 1980;255:3371-6.
Gibson et al., "*Giardia lamblia*: Incorporation of Free and Conjugated Fatty Acids Into Glycerol-Based Phospholipids", 1999. Exp. Parasitol. 92:1-11.
Gillin. "*Giardia lamblia*: The Role of Conjugated and Unconjugated Bile Salts in Killing by Human Milk", 1987. Exp. Parasitol. 63:74-83.
Gillin et al., "Cholate-Dependent Killing of *Giardia lamblia* by Human Milk", 1985 Infect. Immun. 47:619-622.
Giusto et al., "Lipid Metabolism in Photoreceptor Membranes: Regulation and Mechanisms", Neurochem. Res. 22, 445-453 (1997).
Gillon et al., "Features of Small Intestinal Pathology (Epithelial Cell Kinetics, Intraepithelial Lymphocytes, Disaccharidases) in a . . . ", 1982. Gut. 23:498-506.
Glickman et al., "Characterizations, Distribution and Biosynthesis of the Major Ganglioside of Rat Intestinal Mucosa", Biochim. Biophys. Acta 424 (1976) 17-25.
Guelman et al., "GM1 Ganglioside Treatment Protects Against Long-Term Neurotoxic Effects of Neonatal X-irradiation on Cerebellar . . . ", Brain Res. 858 (2000) 303-311.
Hailstones et al., "Regulation of Caveolin and Caveolae by Cholesterol in MDCK Cells", J Lipid Res 1998;39(2):369-79.
Hakomori et al., "Variation in Components and Function of Glycosignaling Domain, and Factors Affecting Them", Glycobiology 2000;10(10):1086-7.
Hara et al., "Occurrence of Sulfatide as a Major Glycosphingolipid in WHHL Rabbit Serum Lipoproteins", J. Biochem. 102 (1987) 83-92.
Ho et al., "Development and Regulation of Rhodopsin Kinase in Rat Pineal and Retina", J. Neurochem. 46, 1176-1179 (1986).
Hoffman et al., "Visual Function in Breast-Fed Term Infants Weaned to Formula With or Without Long-Chain Polyunsaturates at 4 to 6 Months", J. Pediatr. 142, 669-677 (2003).
Hogyes et al., "Neuroprotective Effect of Developmental Docosahexaenoic Acid Supplement Against Excitotoxic Brain . . . ", Neuroscience 119 (2003) 999-1012.

Holgersson et al., "Human Large Intestine Glycolipids", Biochimie 1988;70:1565-74.
Holmgren et al., "Comparison of Receptors for Cholera and Escherichia coli Enterotoxins in Human Intestine", 1985. Gasteroenterology. 89:27-35.
Holub et al., "Nutritional Regulation of Cellular Phosphatidylinositol", in: P.M. Conn and A.R. Means (Eds), Methods in Enzymology, Academic Press, New York, 1987, pp. 234-244.
Honma et al., "Induction of Differentiation of Cultured Human and Mouse Myeloid Leukemia Cells by Alkyl-Lysophospholipids", Cancer Res. 41 (1981) 3211-3216.
Horrocks, "Ether lipids", in: F. Snyder (Ed.), Content, Composition, and Metabolism of Mammalian and Avian Lipids, Academic Press, New York, 1972, pp. 177-272.
Huster, et al., "Strength of Ca2+ Binding to Retinal Lipid Membranes: Consequences for Lipid Organization", Biophys. J. 78, 3011-3018 (2000).
Igarashi et al., "Agonist-Modulated Targeting of the EDG-1 Receptor to Plasmalemmal Caveolae", Journal of Biological Chemistry 2000;275(41):32363-70.
Imaizumi et al., "Effects of Dietary Sphingolipids on Levels of Serum and Liver Lipids in Rats", Nutr Res 1992;12:543-8.
Incardona et al., Cholesterol in Signal Transduction, Curr Opin Cell Biol 2000;12(2):193-203.
Itoh et al., "Modified Bartlett Assay for Microscale Lipid Phosphorus Analysis", Anal Biochem 1986;154(1):200-4.
Itoh, et al., "Inorganic Phosphate Regulates the Contraction-Relaxation Cycle in Skinned Muscles of the Rabbit Mesentric Artery", J. Physiol.—London 376, 231-252 (1986).
Iwabuchi et al., "Reconstitution of Membranes Simulating "Glycosignaling Domain"and Their Susceptibility . . . ", Journal of Biological Chemistry 2000;275(20):15174-81.
Iwamori et al., "Gangliosides of Various Rat Tissues: Distribution of Ganglio-N-Tetraose-Containing Gangliosides . . . ", 1984. J. Biochem. 95:761-770.
IUPAC-IUB, Commission on Biochemical Nomenclature: "The Nomenclature of Lipids", Eur. J. Biochem. 79 (1977) 11-21.
Jarrol et al., "Lipid and Carbohydrate Metabolism of Giardia lamblia", 1981. Mol. Biochem. Parasitol. 2:187-196.
Jennnings et al., "The Significance of Lowered Jejunal Disaccharidase Levels", 1976. Aust. NZ J. Med. 6:556-560.
Jumpsen et al., "During Neuronal and Glial Cell Development Diet n-6 to n-3 Fatty Acid Ratio Alters the Fatty Acid Composition . . . ", Biochim Biophys Acta 1997;1347(1):40-50.
Karlsson et al., "Biochemical Development of Rat Forebrains in Severe Protein and Essential Fatty Acid Deficiencies", J Neurochem 1978;31:657-62.
Karlsson, "Microbial Recognition of Target-Cell Glycoconjugates", 1995. Curr. Opin. Structur. Bio.5:622-635.
Kasahara et al., "Possible Roles of Glyucosphingolipids in Lipid Rafts", Biophysical Chemistry 1999;82(2-3):121-7.
Keenan et al., "The Structure of Milk." In: Handbook of Milk Composition. Jensen RG, ed. Academic Press: New York, pp. 5-85, 1995.
Keenan et al., "Physical Equilibria: Lipid phase", In: Fundamentals of Dairy Chemistry, 3rd ed. Wong NP, ed. Van Nostrand Reinhold Company: New York, pp. 511-582, 1988.
Katagiri et al., "Activation of Src Family Kinase Yes Induced by Shiga Toxin Binding to Globotriaosyl Ceramide . . . ", Journal of Biological Chemistry 1999;274(49):35278-82.
Kobayashi et al., "A Long-Term Feeding of Sphingolipids Affected the Levels of Plasma Cholesterol and Hepatic Triacylglycerol . . . ", Nutr Res 1997;17:111-4.
Koldovsky, "Hormonally Active Peptides in Human Milk", Acta Paediatr Suppl 1994;402:89-93.
Koumanov et al., "Modulation of Human Type II Secretory Phospholipase A2 by Sphingomyelin and Annexin VI", Biochem J 1997;326 ( Pt 1):227-33.
Krajnc et al., "Neonatal Hypoxia; Early Neurotransmitter Responses and the Consequences of Treatment With GM1 Ganglioside", J Pharmacol Exp Ther 1994;271:1299-305.
Kyogashima et al., "Escherichia coli K99 Binds to N-Glycolylsialoparagloboside and N-Glycolyl-GM3 Found in Piglet Small Intestine", 1989. Arch. Biochem. Biophys. 270:391-397.

Laegreid et al., "Trace Amounts of Ganglioside GM1 in Human Mile Inhibit Enterotoxins From Vibrio cholerae and Escherichia coli", Life Sci 1987;40(1):55-62.
Lazzaro et al., "GM1 Reduces Infarct Volume After Focal Cerebral Ischemia", Exp Neurol 1994;125:278-85.
Ledeen, "Biosynthesis, Metabolism, and Biological Effects of Gangliosides", Neurobiology of Glycoconjugates. New York: Plenum Press; 1989.
Ledeen et al., "The Role of GM1 and Other Gangliosides in Neuronal Differentation, Overview and New Finding", Ann. N. Y. Acad. Sci. 845 (1998) 161-175.
Leikin et al., "In Vivo Cholesterol Removal From Liver Microsomes Induces Changes in Fatty Acid Desaturase Activities", Biochim. Biophys. Acta 963 (1988) 311-319.
Lencer et al., "Targeting of Cholera Toxin and Escherichia coli Heat Labile Toxin in Poliarized Epithelia", Journal of Cell Biology 1995;131(4):951-62.
Lencer et al., "Transcytosis of Cholera Toxin Subunits Across Model Human Intestinal Epithelia", Proc Natl Acad Sci USA 1995; 92:10094-8.
Leray et al., "Molecular Species of Choline and Ethanolamine Phospholipids in Rat Cerebellum During Development", J. Neurochem. 54 (1990) 1677-1681.
Liu et al., "Compartmentalized Production of Ceramide at the Cell Surface", J Biol Chem 1995;270(45):27179-85.
Majoul et al.,. "Transport of an External Lys-Asp-Glu-Leu (SKEL) Protein from the Plasma Membrane to the Endoplasmic Reticulum", J Cell Biol 1996;133(4):777-89.
Maekawa et al., "Cholesterol-Dependent Localization of NAP-22 on a Neuronal Membrane Microdomain (Raft)", J Biol Chem 1999;274:21369-74.
Malewicz et al., "Lipids in Gap Junction Assembly and Function", Lipids 1990;25:419-27.
Malisan et al., "GD3 Ganglioside and Apoptosis", Biochim. Biophys. Acta 1585 (2002) 179-187.
Mather. "Proteins of the Milk-Fat Globule Membrane as Markers of Mammary Epithelial Cells . . . ", Neville MC, Daniel CW, eds. Plenum Press: New York, pp. 217-267, 1987.
Mavromoustakos et al., "Ether Phospholipid-AZT Conjugates Possessing Anti-HIV and Antitumor Cell Activity.", J. Med. Chem. 44 (2001) 1702-1709.
Merrill et al., "Sphingolipids—The Enigmatic Lipid Class: Biochemistry, Physiology, and Pathophysiology", Toxicol. Appl. Pharmacol. 142 (1997) 208-225.
Mendez-Otero et al., "Functional Role of a Specific Ganglioside in Neuronal Migration and Neurite Outgrowth", Braz. J. Med. Biol. Res. 36, 1003-1013 (2003).
Merrill et al., "Sphingolipid Biosynthesis de Novo by Rat Hepatocytes in Culture", J. Biol. Chem. 270 (1995) 13834-13841.
Mohand-Said et al., "Intravitreal Injection of Ganglioside GM1 After Ischemia Reduces Retinal Damage in Rats", Stroke 28 (1997) 617-621.
Moran et al., "Engagement of GPI-Linked CD48 Contributes to TCR Signals and Cytoskeletal Reorganization: A Role for . . . ", Immunity 1998;9:787-796.
Morgan et al., "Effects of Administration of N-Acetylneuraminic Acid (NANA) on Brain NANA Content and Behavior", J Nutr 1980;110:416-24.
Moxey et al., "Development of Villus Absorptive Cells in the Human Fetal Small Intestine: A Morphological and Morphometric Study", Anatomical Record 1979;195(3):462-83.
Murphy et al., "Effects of Differentiation on the Phospholipid and Phospholipid Fatty Acid Composition . . . ", Biochim. Biophys. Acta 1167 (1993) 131-136.
Nilsson, "Metabolism of Sphingomyelin in the Intestinal Tract of the Rat", Biochim. Biophys. Acta 164 (1968) 575-584.
Nishizawa et al., "Effect of Dietary DHA on DHA Levels in Retinal Rod Outer Segments in Young Versus Mature Rats", Int. J. Vitam. Nutr. Res. 73, 259-265 (2003).
Nixon et al., "Comparison of Alkylacylglycerol vs. Diacylglycerol as Activators of Mitogen-Activated Protein Kinase . . . ", Biochim. Biophys. Acta 1347 (1997) 219-230.

Ogura et al., "Metabolism of Exogenous Gangliosides GM1 and Chemically Modified GM1 in Mice", J. Biochem. 104 (1988) 87-92.

Oishi et al., "Inhibition of Na, K-ATPase and Sodium Pump by Anticancer Ether Lipids and Protein Kinase C Inhibitors . . . ", Biochem. Biophys. Res. Commun. 157 (1988) 1000-1006.

Okayasu et al., "Platelet-Activating Factor Stimulates Metabolism of Phosphoinositides via Phospholipase A2 in Primary . . . ", J Lipid Res 1987;28(7):760-7.

Ortaldo et al., "T Cell Activation via the Disialoganglioside GD3: Analysis of Signal Transduction", Journal of Leukocyte Biology 1996;60(4):533-9.

Ortega et al., "Cholesterol Effect on Enzyme Activity of the Sarcolemmal (Ca2+ + Mg2+ )- ATPase From Cardiac Muscle", Biochim Biophys Acta 1984;773:231-6.

Ortega-Barria et al., "Growth Inhibition of the Intestinal Parasite *Giardia lamblia* by a Dietary Lectin is Associated with Arrest of the Cell Cycle", 1994. J. Exp. Med. 94:228.

Paltauf, "Ether Lipids in Biomembranes", Chem. Phys. Lipids 74 (1994) 101-139.

Paltauf, "Intestinal Uptake and Metabolism of Alkyl Acyl Glycero Phospholipids and of Alkyl Glycerophospholipids in the Rat", Biochim. Biophys. Acta 260 (1972) 352-364.

Pan et al., "Variation of the Ganglioside Compositions of Human Milk, Cow's Milk and Infant Formulas", Early Hum Dev 2000;57:25-31.

Parker et al., "Evidence of Protein Kinase C Involvement in Phorbol Diester-Stimulated Arachidonic Acid Release . . . ", J. Biol. Chem. 262 (1987) 5385-5393.

Parpal et al., "Cholesterol Depletion Disrupts Caveolae and Insulin Receptor Signaling for Metabolic Control Via Insulin Receptor Substrate-1 . . . ", J Biol Chem 2001;276:9670-8.

Parton, "Ultrastructural Localization of Gangliosides; GM1 Is Concentrated in Caveolae", J Histochem Cytochem 1994;42:155-66.

Patton et al. "The Milk Fat Globule Membrane", Biochim Biophys Acta 415:273-309, 1975.

Perkkio et al., "Time of Appearance of Immunoglobulin-Containing Cells in the Mucosa of the Neonatal Intestine", Pediatr Res 1980;14:953-5.

Polit et al., "Effects of Docosahexaenoic Acid on Retinal Development: Cellular and Molecular Aspects", Lipids 36 (2001) 927-935.

Popik et al., "Human Immunodeficiency Virus Type 1 Uses Lipid Raft-Colocalized CD4 and Chemokine Receptors for Productive . . . ", J Virol 2002;76(10):4709-22.

Principe et al., "Flow Cytometric Monitoring of Anthracycline Accumulation After Anti-Neoplastic Ether Phospholipid Treatment", Anticancer Drugs 5 (1994) 329-335.

Prinetti et al., "Glycosphingolipid-Enriched Signaling Domain in Mouse Neuroblastoma Neuro2a Cells", Journal of Biological Chemistry 1999;274(30):20916-24.

Prescott et al., "Platelet-Activating Factor", J Biol Chem 1990;265(29):17381-4.

Record et al., "Evidence for a Highly Asymmetric Arrangement of Ether- and Diacyl-Phospholipid Subclasses in the Plasma . . . ", Biochim. Biophys. Acta 778 (1984) 449-456.

Reiner et al., "Human Milk Kills *Giardia lamblia* by Generating Toxic Lipolytic Products", 1986. J. Infect. Dis. 154:825-832.

Reiss et al., "Delayed Oxidative Degradation of Polyunsaturated Diacyl Phospholipids in the Presence of Plasmalogen Phospholipids in vitro", Biochem. J. 323 (1997) 807-814.

Rietveld et al., "The Differential Miscibility of Lipids as the Basis for the Formation of Functional Membrane Rafts:", Biochim Biophys Acta 1998;1376:467-79.

Roberts-Thomson et al., "Giardiasis in the Mouse: An Animal Model", 1976. Gastroenterology. 71:57-61.

Rohrer et al., "Killing of *Giardia lamblia* by Human Milk is Mediated by Unsaturated Fatty Acids", 1986. Antimicrob. Agents Chemother. 30:254-257.

Rolsma et al., "Structure and Function of a Ganglioside Receptor for Porcine Rotavirus", Journal of Virology 1998;72(11):9079-91.

Rouser et al., "Curvilinear Regression Course of Human Brain Lipid Composition Changes With Age", Lipids 3 (1968) 284-287.

Rueda et al., "Changes During Lactation in Ganglioside Distribution in Human Milk from Mothers Delivering Preterm and Term Infants", 1996. Biol. Chem. 377:599-601.

Rueda et al., "Addition of Gangliosides to an Adapted Milk Formula Modifies Levels of Fecal *Escherichia coli* in Preterm Newborn Infants", 1998a. J. Pediatr. 133:90-94.

Rueda et al., "Neonatal Dietary Gangliosides", Early Human Development 1998b;53:S135-S147.

Samuel et al. "The Role of Cholesterol and Glycosylphosphatidylinositol-Anchored Proteins of Erythrocyte Rafts in Regulating . . . ", J Biol Chem 2001;276:29319-29.

Sanchez-Diaz et al., "A Critical Analysis of Total Sialic Acid and Sialoglycoconjugate Contents of Bovine . . . ", J Pediatr Gastroenterol Nutr 1997;24:405-410.

Schmelz et al., "Uptake and Metabolism of Sphingolipids in Isolated Intestinal Loops of Mice", J. Nutr. 124 (1994) 702-712.

Schmelz et al., "Colonic Cell Proliferation and Aberrant Crypt Foci Formation Are Inhibited by Dairy Glycosphingolipids in . . . ", J. Nutr. 130 (2000) 522-527.

Sciorra et al., "Sequential Actions of Phospholipase D and Phosphatidic Acid Phosphohydrolase 2b Generate . . . ", Molecular Biology of the Cell 1999;10(11):3863-76.

Seewald et al., "Inhibition of Growth Factor-Dependent Inositol Phosphate Ca2+ Signaling by antitumor Ether Lipid Analogues", Cancer Res. 50 (1990) 4458-4463.

Senn et al., "Gangliosides in Normal Human Serum", Eur J Biochem 1989;181:657-62.

Seyfried, et al., "Gangliosdies Gp3: Structure, Cellular Distribution, and Possible Function", Mol. Cell Biochem. 68, 3-10 (1985).

Simons et al., "Functional Rafts in Cell Membranes", Nature 1997;387 (6633):569-72.

Sindelar et al., "The Protective Role of Plasmalogens in Iron-Induced Lipid Peroxidation", Free Radic. Biol. Med. 26 (1999) 318-324.

Slotte, "Sphingomyelin-Cholesterol Interactions in Biological and Model Membranes", Chem Phys Lipids 1999;102:13-27.

Smart et al., "Hormonal Regulation of Caveolae Internalization", Journal of Cell Biology 1995;131(4):929-38.

Smart et al., "The Caveolae Internalization Cycle: Regulation by PKC α-Mediated Phosphorylation of a 90-kDa Protein", Molecular Biology of the Cell 1995;6:778.

Sonnino et al., "Recognition by Two-Dimensional Thin-Layer Chromatography and Densitometric Quantification of Alkali-Labile . . . ", Anal Biochem 1983;128:104-14.

Sorice et al., "Evidence for the Existence of Ganglioside Molecules in the Antigen of Entamoeba Histolytica", 1996. Parasite Immunol. 18:133-137.

Stauffer et al., "Compartmentalized IgE Receptor-Mediated Signal Transduction in Living Cells", J Cell Biol 1997;139:1447-54.

Stevens et al., "Uptake and Cellular Localization of Exogenous Lipids by *Giardia lamblia*, a Primitive Eukaryote", 1997. Exp. Parasitol. 86:133-143.

Stulnig et al., "Polyunsaturated Eicosapentaenoic Acid Displaces Proteins From Membrane Rafts by . . . ", Journal of Biological Chemistry 2001;276(40):37335-40.

Suzuki, "A Simple and Accurate Micromethod for Quantitive Determination of Ganglioside Patterns", 1964. Life Sci. 3:1227-1233.

Suh, Wierzbicki, and Clandinin, "Dietary Fat Alters Membrane Composition in Rod Outer Segments in Normal and Diabetic Rats . . . ", BBA-Lipid Lipid Met. 1214, 54-62 (1994).

Sun et al., "Age Changes in the Lipid Composition of Whole Homogenates and Isolated Myelin Fractions of Mouse Brain", J Gerontol 1972;27:10-17.

Svennerholm, "Quantitative Estimation of Sialic Acids", Biochimica et Biophysica Acta 1957;24:604-11.

Svennerholm, "Chromatographic Separation of Human Brain Gangliosides", J. Neurochem. 10 (1963) 613-623.

Svennerholm, "The Gangliosides", Journal of Lipid Research 1964;5:145-55.

Svennerholm et al., "Human Brain Gangliosides: Developmental Changes from Early Fetal Stage to Advanced Age", Biochim. Biophys. Acta 1005 (1989) 109-117.

Takamizawa et al., "Selective Changes in Gangliosides of Human Milk During Lactation", Biochim Biophys Acta 1986;879:73-7.

Thompson et al., "Inhibition of the Adherence of Cholera Toxin and the Heat-Labile Enterotoxin of *Escherichia coli* to . . . ", Biochem. Pharmacol. 56 (1998) 591-597.

Triantafilou et al., "Mediators of Innate Immune Recognition of Bacteria Concentrate in Lipid Rafts and Facilitate . . . ", J Cell Sci 2002;115(Pt 12):2603-11.

Underdown et al., "Giardiasis in Mice: Studies on the Characteristics of Chronic Infection in C3H/He Mice", 1981. J. Immunol.; 126:669-672.

Vanier et al., "Developmental Profiles of Gangliosides in Human and Rat Brain", J Neurochem 1971;18:581-92.

Vazquez et al. "Dietary Gangliosides Positively Modulate the Percentages of Th1 and Th2 Lymphocyte Subsets in Small Intestine of Mice at Weaning", Biofactors 15 (2001) 1-9.

Vesper et al., "Sphingolipids in Food and the Emerging Importance of Sphingolipids to Nutrition", J. Nutr. 129 (1999) 1239-1250.

Walterspiel et al., "Secretory Anti-*Giardia lamblia* Antibodies in Human Milk: Protective Effects Against Diarrhea", 1994. Pediatrics. 93:28-31.

Watarai et al., "Gangliosides as a Possible Receptor on the Bovine Erythrocytes for *Theileria sergenti*", 1995. J. Vet. Med. Sci. 57:17-22.

Welte et al., "Stimulation of T Lymphocyte Proliferation by Monoclonal Antibodies Against Gp3 Ganglioside", J Immunol 1987;139:1763-71.

Williams et al., "The Use of Sep-Pak C18 Cartridges During the Isolation of Gangliosides", Journal of Neurochemistry 1980;35(1):266-9.

Williams et al., "Docosahexaenoic Acid (DHA) Alters the Phospholipid Molecular Species Composition . . . ", Biochimica et Biophysica Acta-Biomembranes 1999;1418(1):185-96.

Wilson et al., "Biogenesis of the Apical Endosome-Lysosome Complex During Differentiation of Absorptive Epithelial . . . ", Journal of Cell Science 1991;100:133-43.

Wolf et al., "Uncoupling of the Cholera Toxin-GM1 Ganglioside Receptor Complex Form Endocytosis, . . . ", Journal of Biological Chemistry 2002;277(18):16249-56.

Wolfe "Giardiasis", 1992. Clin. Microbiol. Rev. 5:93-100.

Xi et al., "Effect of Dietary n-3 Fatty Acids on the Composition of Long- and Very-Long-Chain Polyenoic Fatty Acid in Rat Retina", J. Nutr. Sci. Vitaminol. 49, 210-213 (2003).

Yamamura et al., "A Close Association of GM3 with c-Src and Rho in GM3-Enriched Microdomains at the B16 Melanoma . . . ", Biochem Biophys Res Commun 1997;236(1):218-22.

Zheng et al., "Inhibition of Protein Kinase C, (Sodium plus Potassium)-Activated Adenosine Triphosphatase, and Sodium Pump . . . ", Cancer Res. 50 (1990) 3025-3031.

Birecki et al. "Dietary Gangliosdies Enhance in Vitro Lipid Uptake in Weanling Rats, Journal of Pediatric Gastroenterology and Nutrition", Jan. 2006, 22: 59-65.

Park, et al. "Dietary Ganglioside Decreases Cholesterol Content, Caveolin Expression and Inflammatory Mediators in Rat Intestinal Microdormains", Glycobiology 2005, vol. 15.

Park, et al. "Diet-Induced Changes in Membrane Gangliosides in Rat Intestinal Mucosa, Plasma and Brain Journal of Pediatric Gastroenterology and Nutrition", Apr. 2005; 20: 487-495.

Park et al. "Dietary Ganglioside and Long-Chain Polyunsaturated Fatty Acids Increase Ganglioside GD3 Content", Invest. Ophthalmology & Visual Science, Jul. 2005, vol. 46.

Park et al. Dietary Gangliosides Increase the Content and Molecular Percentage of Ether Phospholipids Containing 20: 4n-6 and 22:6n-3 J. Nut. Bio 17 (2006) 337-344.

Suh et al. "Dietary Lipids Containing Gangliosides Reduce *Giardia muris* Infection in Vivo and Survival of *Giardia lamblia* Trophozoites in Vitro", Parasitology (2004) 128: 595.

The Merck Manual of Diagnosis and Therapy, Seventeenth Ed, 1999 Merck Research Laboratories, pp. 283-286, 1249-1250 and 2084.

Machine Translation of DE 4430041, translated online at v3.espacenet.com (published 1996).

Colarow et al. "Characterization and biological activity of gangliosides in buffalo milk" Biochimica et Biophysica Acta 1631, 2003, pp. 94-106.

Pan et al. "Variation of the ganglioside compositions of human milk, cow's milk, and infant formulas", Early Human Development, vol. 57, 2000, 25-31.

Puente et al. "Gangliosides in Bovine Milk" Biol. Chem. Hoppe-Seyler, vol. 373, May 1992, pp. 283-288.

Bucolo et al. "Effects of Mipragoside on Ocular Allergic Inflammation in the Rabbit" Journal of Ocular Pharmacology, vol. 9, No. 4, 1993, 321-332.

Oliveria et al. "GM-1 Ganglioside Treatment Reduces Motoneuron Death After Ventral Root Avulsion in Adult Rats" Neuroscience Letters, vol. 293, No. 2, p. 131 2000.

Sugimoto et al. "Total Synthesis of Gangliosides GM1 and GM2" Carbohydrate Research, vol. 156, 1986m oo C1-C5 XP001053330, (1986).

* cited by examiner

Fatty acid composition of alkenylacyl, alkylacyl and diacyl subclasses in CPG in intestinal mucosa of animals fed control diet or treatment diets[1]

| | Alkenylacyl-CPG | | | Alkylacyl-CPG | | | Diacyl-CPG | | |
|---|---|---|---|---|---|---|---|---|---|
| | Control | SM | GG | Control | SM | GG | Control | SM | GG |
| C 14:0 | 6.2 ± 1.6 | 8.1 ± 5.4 | 5.0 ± 1.3 | 5.4 ± 2.1 | 6.1 ± 2.5 | 6.4 ± 2.5 | 0.8 ± 0.2 | 1.1 ± 0.3 | 0.9 ± 0.2 |
| C 14:1 | 1.9 ± 1.5[a] | 0.5 ± 0.3[b] | 0.4 ± 0.6[b] | 1.0 ± 0.7 | 0.3 ± 0.4 | 0.5 ± 0.5 | - | - | - |
| C 16:0 | 33.7 ± 5.8 | 32.2 ± 8.6 | 32.3 ± 8.2 | 34.3 ± 7.3 | 33.3 ± 6.1 | 33.0 ± 4.3 | 21.0 ± 1.7[b] | 24.4 ± 2.2[a] | 24.3 ± 2.5[a†] |
| C 16:1(7) | 1.4 ± 1.6 | 0.8 ± 0.5 | 1.1 ± 1.6 | 0.4 ± 0.6 | 0.7 ± 0.6 | 0.4 ± 0.4 | 0.4 ± 0.0 | 0.3 ± 0.2 | 0.2 ± 0.1 |
| C 18:0 | 25.5 ± 3.7 | 23.2 ± 5.9 | 22.0 ± 6.7 | 25.8 ± 3.6[a] | 17.6 ± 5.7[b] | 19.0 ± 4.6[b†] | 22.7 ± 1.1[b] | 24.8 ± 3.4[b] | 27.7 ± 3.2[a†] |
| C 18:1(9) | 8.8 ± 4.3 | 8.5 ± 4.3 | 5.9 ± 2.3 | 8.7 ± 3.1 | 7.7 ± 1.5 | 7.4 ± 1.3 | 11.6 ± 0.8[a] | 10.5 ± 0.8[b] | 9.2 ± 1.1[c¶] |
| C 18:2(6) | 3.2 ± 1.8 | 3.2 ± 2.1 | 2.4 ± 1.6 | 5.3 ± 4.1 | 5.5 ± 1.8 | 5.5 ± 2.9 | 30.0 ± 1.6[a] | 26.6 ± 3.1[b] | 23.5 ± 3.4[c‡] |
| C 18:3(6) | 0.5 ± 0.4 | 1.0 ± 1.2 | 0.7 ± 0.8 | 0.8 ± 0.6 | 0.7 ± 0.4 | 0.6 ± 0.7 | 0.1 ± 0.0 | 0.1 ± 0.1 | 0.1 ± 0.1 |
| C 18:3(3) | 0.5 ± 0.6 | 0.3 ± 0.2 | 0.6 ± 0.6 | 0.5 ± 0.9 | 0.1 ± 0.2 | 0.4 ± 0.3 | 0.2 ± 0.0 | 0.1 ± 0.0 | 0.1 ± 0.0 |
| C 20:0 | 1.2 ± 1.2 | 1.0 ± 0.4 | 1.9 ± 1.7 | 1.0 ± 0.2 | 0.8 ± 0.4 | 0.9 ± 0.6 | 0.3 ± 0.0 | 0.3 ± 0.1 | 0.3 ± 0.1 |
| C 20:1 | 0.3 ± 0.4 | 0.6 ± 0.3 | 1.0 ± 0.7 | 0.4 ± 0.3 | 0.4 ± 0.4 | 0.6 ± 1.0 | 0.5 ± 0.1 | 0.4 ± 0.0 | 0.4 ± 0.1 |
| C 20:2 | 0.0 ± 0.1 | 0.1 ± 0.1 | 0.7 ± 1.1 | 0.1 ± 0.3 | 0.1 ± 0.2 | 2.6 ± 3.0 | 0.2 ± 0.1 | 0.1 ± 0.1 | 0.2 ± 0.1 |
| C 20:3(6) | 0.3 ± 0.4 | 0.6 ± 0.7 | 0.4 ± 0.5 | 0.5 ± 0.6[b] | 1.3 ± 1.3[a] | 0.0 ± 0.1[b†] | 0.4 ± 0.1 | 0.4 ± 0.1 | 0.4 ± 0.1 |
| C 20:4(6) | 1.8 ± 0.6[ab] | 1.1 ± 0.5[b] | 3.1 ± 2.1[a] | 5.7 ± 3.7 | 9.5 ± 4.8 | 9.3 ± 6.7 | 9.4 ± 0.4 | 8.8 ± 2.8 | 10.2 ± 1.5 |
| C 20:3(3) | 0.3 ± 0.4 | 0.9 ± 0.8 | 0.7 ± 0.8 | 0.4 ± 0.4 | 0.4 ± 0.4 | 0.3 ± 0.4 | 0.0 ± 0.0 | 0.0 ± 0.0 | 0.0 ± 0.0 |
| C 20:5(3) | 1.5 ± 0.9 | 0.6 ± 0.6 | 2.2 ± 2.0 | 0.7 ± 0.6 | 0.8 ± 0.5 | 1.0 ± 0.5 | 0.3 ± 0.1 | 0.2 ± 0.1 | 0.3 ± 0.1 |
| C 22:0 | 0.5 ± 0.4[b] | 2.6 ± 1.5[a] | 2.2 ± 2.1[ab] | 1.3 ± 0.8 | 2.2 ± 1.3 | 1.8 ± 1.0 | 0.2 ± 0.0 | 0.2 ± 0.1 | 0.3 ± 0.2 |
| C 22:1(9) | 1.3 ± 1.0 | 1.5 ± 2.3 | 1.5 ± 1.6 | 0.1 ± 0.2[b] | 1.2 ± 1.0[ab] | 1.7 ± 1.5[a] | 0.2 ± 0.0 | 0.1 ± 0.0 | 0.2 ± 0.0 |
| C 22:2(6) | 2.1 ± 1.1[ab] | 1.5 ± 0.9[b] | 4.0 ± 2.9[a] | 0.0 ± 0.0[b] | 2.9 ± 2.6[a] | 1.2 ± 1.4[ab†] | 0.0 ± 0.0 | 0.1 ± 0.2 | 0.1 ± 0.1 |
| C 22:4(6) | 0.1 ± 0.3 | 0.0 ± 0.0 | 0.0 ± 0.0 | 0.4 ± 0.4 | 0.7 ± 0.9 | 0.6 ± 0.8 | 0.1 ± 0.1 | 0.1 ± 0.2 | 0.1 ± 0.0 |
| C 24:0 | 2.4 ± 1.5 | 3.3 ± 1.5 | 3.2 ± 2.2 | 1.8 ± 1.0[a] | 1.8 ± 1.0[a] | 0.6 ± 0.8[b] | 0.1 ± 0.0 | 0.1 ± 0.0 | 0.2 ± 0.1 |
| C 22:6(3) | 1.2 ± 1.1 | 0.9 ± 1.1 | tr[2] | 1.2 ± 1.0[b] | 2.7 ± 0.9[a] | 4.2 ± 1.8[a‡] | 1.4 ± 0.2 | 1.1 ± 0.4 | 1.3 ± 0.2 |
| C 24:1(9) | 5.3 ± 2.9 | 7.5 ± 5.4 | 8.8 ± 3.6 | 4.0 ± 1.8[a] | 3.0 ± 0.7[ab] | 1.8 ± 1.4[b] | 0.1 ± 0.0 | 0.1 ± 0.1 | 0.2 ± 0.1 |
| SFA[3] | 69.5 ± 7.3 | 70.4 ± 10.9 | 66.6 ± 6.6 | 69.6 ± 10.6 | 61.8 ± 9.3 | 61.7 ± 7.8 | 45.2 ± 2.3[b] | 50.7 ± 5.5[a] | 53.6 ± 5.8[a†] |
| MUFA | 19.1 ± 4.8 | 19.4 ± 7.3 | 18.7 ± 2.6 | 14.6 ± 2.5 | 13.2 ± 1.9 | 12.4 ± 2.2 | 12.8 ± 0.9[a] | 11.5 ± 0.9[b] | 10.2 ± 1.1[c¶] |
| PUFA | 11.4 ± 3.6 | 10.2 ± 5.2 | 14.8 ± 4.9 | 15.8 ± 8.9[b] | 25.0 ± 7.6[a] | 25.9 ± 6.6[a] | 42.0 ± 1.7[a] | 37.7 ± 5.7[ab] | 36.2 ± 4.8[b] |

[1] Means ± SD (% w/w) in 3 subclasses from 7, 8 and 7 animals, for the control, SM and GG group, respectively. Within a row, values with different superscript letters are significantly different at P< 0.05. Superscript letters with †, ‡, and ¶ are significantly different at P<0.01, P<0.001, and P<0.0001, respectively. [2] tr represents trace amount.
[3] SFA, MUFA and PUFA represent saturated fatty acids, monounsaturated fatty acids and polyunsaturated fatty acids, respectively.

FIG. 3

Fatty acid composition of alkenylacyl, alkylacyl and diacyl subclasses in EPG in intestinal mucosa of animals fed control diet or treatment diets[1]

| | Alkenylacyl-EPG | | | Alkylacyl-EPG | | | Diacyl-EPG | | |
|---|---|---|---|---|---|---|---|---|---|
| | Control | SM | GG | Control | SM | GG | Control | SM | GG |
| C14:0 | 3.9 ± 1.3 | 3.1 ± 1.1 | 3.1 ± 1.2 | 4.4 ± 1.5 | 3.0 ± 1.9 | 2.5 ± 1.5 | 0.7 ± 0.4 | 0.4 ± 0.1 | 0.5 ± 0.2 |
| C14:1 | 0.7 ± 0.3 | 0.9 ± 1.0 | 0.5 ± 0.4 | 0.7 ± 0.6[a] | 0.2 ± 0.2[b] | 0.2 ± 0.1[b] | - | - | - |
| C16:0 | 19.0 ± 3.6[a] | 15.4 ± 1.7[b] | 14.2 ± 2.3[b†] | 18.7 ± 5.4[a] | 12.7 ± 3.2[b] | 11.4 ± 1.9[b†] | 9.8 ± 2.5 | 8.5 ± 1.8 | 8.1 ± 1.9 |
| C16:1(7) | 2.1 ± 1.3 | 2.5 ± 0.7 | 2.3 ± 0.6 | 0.6 ± 0.5 | 0.3 ± 0.2 | 0.3 ± 0.3 | 0.1 ± 0.1 | 0.1 ± 0.1 | 0.1 ± 0.0 |
| C18:0 | 17.6 ± 4.7[a] | 14.4 ± 4.1[ab] | 11.6 ± 2.7[b] | 14.8 ± 3.2[a] | 11.2 ± 4.0[b] | 9.8 ± 2.1[b] | 46.9 ± 8.6 | 43.5 ± 7.4 | 42.6 ± 4.3 |
| C18:1(9) | 9.0 ± 2.0 | 8.2 ± 1.2 | 7.3 ± 0.9 | 12.0 ± 3.1 | 11.6 ± 1.9 | 9.2 ± 1.3 | 12.2 ± 2.9 | 13.1 ± 2.1 | 12.8 ± 1.5 |
| C18:2(6) | 4.0 ± 1.3 | 4.6 ± 0.5 | 4.1 ± 0.7 | 5.4 ± 1.0 | 6.4 ± 0.6 | 5.6 ± 0.8 | 11.8 ± 3.3 | 14.7 ± 3.0 | 14.2 ± 1.8 |
| C18:3(6) | 0.6 ± 0.3[a] | 0.6 ± 0.1[a] | 0.3 ± 0.1[b] | 0.5 ± 0.4 | 0.5 ± 0.3 | 0.4 ± 0.2 | 0.2 ± 0.1 | 0.1 ± 0.1 | 0.2 ± 0.0 |
| C18:3(3) | 2.2 ± 1.2 | 2.1 ± 0.9 | 2.1 ± 1.0 | 0.5 ± 0.3 | 0.6 ± 0.3 | 0.6 ± 0.2 | 0.3 ± 0.5 | 0.2 ± 0.1 | 0.1 ± 0.0 |
| C20:0 | 0.6 ± 0.2 | 0.5 ± 0.2 | 0.5 ± 0.2 | 1.6 ± 1.2 | 1.1 ± 0.2 | 1.1 ± 0.1 | 0.5 ± 0.2 | 0.5 ± 0.1 | 0.3 ± 0.3 |
| C20:1 | 1.0 ± 0.8 | 1.0 ± 0.2 | 0.8 ± 0.1 | 2.1 ± 1.2 | 2.1 ± 0.4 | 2.1 ± 0.5 | 0.3 ± 0.1 | 0.2 ± 0.1 | 0.2 ± 0.1 |
| C20:2 | 1.2 ± 1.4 | 0.5 ± 0.7 | 1.1 ± 0.9 | 0.4 ± 0.3 | 0.5 ± 0.3 | 0.7 ± 0.3 | 0.4 ± 0.6 | 0.2 ± 0.1 | 0.1 ± 0.0 |
| C20:3(6) | 0.8 ± 0.6 | 0.9 ± 0.3 | 0.9 ± 0.2 | 1.0 ± 0.5 | 1.2 ± 0.6 | 1.6 ± 0.5 | 0.4 ± 0.2 | 0.5 ± 0.2 | 0.4 ± 0.3 |
| C20:4(6) | 16.9 ± 5.7 | 21.3 ± 3.9 | 23.1 ± 4.9 | 18.5 ± 6.1[b] | 21.9 ± 4.6[ab] | 25.1 ± 2.6[a] | 11.5 ± 3.6[b] | 14.0 ± 3.5[ab] | 15.7 ± 2.6[a†] |
| C20:3(3) | 0.5 ± 0.2[a] | 0.3 ± 0.2[ab] | 0.2 ± 0.1[b] | 0.4 ± 0.2 | 0.4 ± 0.2 | 0.3 ± 0.2 | 0.1 ± 0.1 | 0.1 ± 0.1 | 0.0 ± 0.0 |
| C20:5(3) | 0.6 ± 0.3 | 0.4 ± 0.3 | 0.5 ± 0.2 | 0.8 ± 0.3 | 0.7 ± 0.4 | 0.6 ± 0.3 | 0.3 ± 0.1 | 0.3 ± 0.2 | 0.2 ± 0.2 |
| C22:0 | 1.3 ± 0.7 | 1.0 ± 0.6 | 0.9 ± 0.2 | 0.7 ± 0.6 | 0.7 ± 0.5 | 1.2 ± 0.9 | 0.5 ± 0.2 | 0.3 ± 0.1 | 0.4 ± 0.2 |
| C22:1(9) | 0.4 ± 0.4 | 0.4 ± 0.4 | 0.8 ± 0.8 | 0.5 ± 0.5 | 1.1 ± 0.9 | 1.0 ± 1.1 | 0.3 ± 0.4 | 0.2 ± 0.1 | 0.2 ± 0.1 |
| C22:2(6) | 1.2 ± 1.5 | 0.5 ± 0.2 | 0.7 ± 0.3 | 1.5 ± 0.9 | 1.6 ± 1.1 | 1.2 ± 0.5 | 0.4 ± 0.3[a] | 0.0 ± 0.0[b] | 0.0 ± 0.1[b†] |
| C22:4(6) | 4.9 ± 2.8[b] | 7.8 ± 1.6[a] | 9.9 ± 2.1[a‡] | 5.8 ± 2.3[b] | 8.3 ± 2.9[ab] | 10.9 ± 2.2[a†] | 0.3 ± 0.2 | 0.4 ± 0.2 | 0.6 ± 0.5 |
| C24:0 | 2.3 ± 1.9 | 1.4 ± 0.7 | 0.9 ± 0.5 | 1.4 ± 0.4[a] | 1.6 ± 0.7[a] | 0.7 ± 0.5[b] | 0.2 ± 0.1 | 0.2 ± 0.1 | 0.3 ± 0.2 |
| C22:6(3) | 7.4 ± 2.6[c] | 10.1 ± 0.9[b] | 12.7 ± 1.8[a‡] | 6.3 ± 1.9[b] | 9.2 ± 2.3[a] | 11.2 ± 1.2[a‡] | 2.0 ± 1.0 | 2.3 ± 1.1 | 2.7 ± 0.5 |
| C24:1(9) | 2.5 ± 1.4 | 2.3 ± 1.5 | 1.5 ± 1.1 | 1.3 ± 0.7 | 2.6 ± 1.6 | 2.4 ± 2.3 | 0.6 ± 0.5 | 0.3 ± 0.1 | 0.2 ± 0.1 |
| SFA[2] | 44.7 ± 9.7[a] | 35.7 ± 5.9[b] | 31.2 ± 5.5[b†] | 41.6 ± 9.8[a] | 30.2 ± 7.1[b] | 26.7 ± 4.4[b†] | 58.6 ± 9.8 | 53.3 ± 8.8 | 50.4 ± 4.9 |
| MUFA | 15.7 ± 4.2 | 15.2 ± 2.5 | 13.2 ± 2.1 | 17.2 ± 3.0 | 17.9 ± 2.8 | 15.2 ± 2.4 | 13.6 ± 2.8 | 13.9 ± 2.1 | 13.4 ± 1.1 |
| PUFA | 39.4 ± 11.3[b] | 49.1 ± 5.4[a] | 55.6 ± 7.4[a†] | 41.2 ± 11.5[b] | 51.9 ± 9.4[a] | 58.1 ± 4.2[a†] | 27.8 ± 7.4[b] | 32.8 ± 7.0[ab] | 36.2 ± 4.2[a] |

[1] Means ± SD (% w/w) in 3 subclasses from 7, 8 and 7 animals, for the control, SM and GG group, respectively. Within a row, values with different superscript letters are significantly different at P<0.05. Superscript letters with †, ‡, and ¶ are significantly different at P<0.01, P<0.001, and P<0.0001, respectively.

[2] SFA, MUFA and PUFA represent saturated fatty acids, mono unsaturated fatty acids and poly unsaturated fatty acids, respectively.

FIG. 4

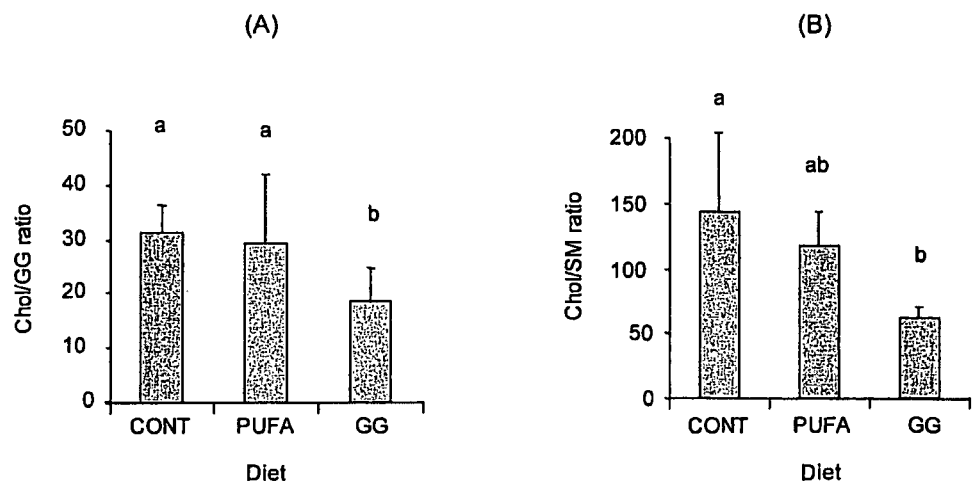
FIG. 7
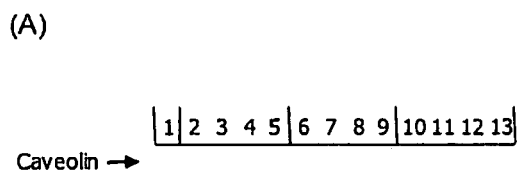
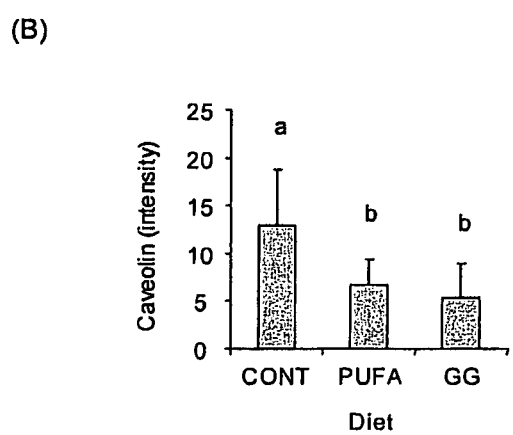
FIG. 8

| Diet group / Statistical P value | Control | SM | GG | P. |
|---|---|---|---|---|
| NANA (mg/DL) | 1.02 ± 0.14[b] | 1.02 ± 0.10[b] | 1.34 ± 0.20[a] | 0.003 |
| Phosphorus (mg/DL) | 6.83 ± 0.71 | 6.92 ± 0.34 | 6.81 ± 0.22 | - |
| Cholesterol (mg/DL) | 111.3 ± 11.4[ab] | 117.8 ± 8.5[a] | 105.4 ± 4.2[b] | 0.03 |
| Triglyceride (mg/DL) | 94.7 ± 27.0[a] | 107.1 ± 18.5[a] | 76.8 ± 10.5[b] | 0.02 |
| NANA / P ratio (mg/mg) | 0.15 ± 0.02[b] | 0.15 ± 0.02[b] | 0.20 ± 0.03[a] | 0.006 |
| Cholesterol / NANA ratio (mg/mg) | 110.1 ± 19.1[a] | 115.5 ± 14.1[a] | 80.4 ± 11.2[b] | 0.002 |
| Cholesterol / P ratio (mg/mg) | 16.26 ± 1.23[a] | 16.97 ± 1.05[a] | 15.34 ± 0.72[a] | 0.06 |

METHODS FOR TREATING INFLAMMATORY BOWEL DISEASE

CROSS REFERENCE TO RELATED APPLICATIONS

This application is a continuation-in-part of and claims priority to U.S. patent application Ser. No. 11/622,858 filed Jan. 12, 2007, which is a continuation-in-part of and claims priority to U.S. patent application Ser. No. 10/551,789, now U.S. Pat. No. 7,781,408, which is a national phase entry of International Patent Application PCT/CA2004/000375 filed Mar. 12, 2004, which claims priority to U.S. patent application Ser. No. 10/404,095 filed Apr. 2, 2003, now U.S. Pat. No. 6,998,392, each of which is incorporated herein by reference.

FIELD

Methods and formulations for treating Inflammatory Bowel Disease are described herein.

BACKGROUND

Gangliosides are specialized sialic acid-containing glycolipids abundant in the outer region of the neuronal lipid bilayer and intestinal brush border. The intestine contains a relatively high amount of ganglioside (as much as 7% of total lipids (Christiansen et al, 1981; Forstner et al., 1973). Change occurs in the composition and molecular structure of gangliosides during intestinal development (Bouhours et al., 1983; Glickman et al, 1976). Total intestinal lipids are comprised of 25 to 35% sphingolipids, including gangliosides and sphingomyelin (Christiansen et al, 1981; Forstner et al., 1973), and microvillus membranes are more enriched in gangliosides than the plasma membranes (Forstner et al., 1973).

Gangliosides are located at the surface of the cell membrane with the hydrophilic oligosaccharide chain extending into the extracellular space. Glycosphingolipid constitutes approximately 20% of the brush border membrane lipids (Forstner et al., 1973). The dominant ganglioside is GM3 which is 7 times more concentrated in the neonatal compared to adult intestine of rats (Bouhours et al., 1983). The specific physiological roles of gangliosides are poorly understood, however, studies showed that gangliosides provide binding sites for a wide range of pathogens including viruses, bacteria and fungi (Holmgren et al., 1985; Kyogashima et al., 1989; Laegreid and Otnaess, 1987; and Rolsma et al., 1998). For example, ganglioside GM3 acts as a natural receptor in pig small intestine for rotavirus (Rolsma et al., 1998) and the enterotoxigenic bacteria Escherichia coli (E. coli) K99 (Kyogashima et al., 1989). Ganglioside GM1 in human intestine (Holmgren et al., 1985) and in human milk (Laegreid et al., 1987) also provides receptors for enterotoxin of Vibrio cholerae and the heat-labile E. coli, thereby acting as a physiological barrier for protection against these enteric infections.

Previous studies showed that gangliosides exist in clusters in the plasma membrane forming glycosphingolipid enriched domains and that these domains are the preferential interaction sites between target cells and pathogens (Karlsson, 1995). Preterm newborn infants fed ganglioside supplemented formula at a concentration of 1.43 mg/100 Kcal, were shown to have significantly lower numbers of E. coli and bifidobacteria in the feces (Rueda et al., 1998).

During early development, important morphological changes occur in the total and relative amounts of gangliosides in neuronal tissues of the brain and retina (Asou et al., 1989; Baumann et al., 1976; Daniotti et al., 1994). One of the primary roles of gangliosides is activation of neuronal cell differentiation and proliferation (Ledeen et al., 1998), influencing synaptogenesis and neuritogenesis (Byrne et al., 1983; Svennerholm et al., 1989) and offering protection against neuronal injury (Guelman et al., 2000; Mohand-Said et al., 1997). Functions in the intestinal mucosa involve toxin receptors of bacterial and viruses (Thompson et al., 1998; Rolsma et al., 1998) and immune activators (Vazquez et al., 2001). Radiolabeling studies have shown that exogenous gangliosides and sphingomyelin are hydrolyzed by enterocyte membrane-bound enzymes such as sphingomyelinase and/or ceramidase (Merrill et al., 1997; Schmelz et al., 1994; Nilsson, 1968). Metabolites such as ceramide, ceramide-1-phosphate, sphingosine, and sphingosine-1-phosphate are transported into enterocytes and reutilized in synthesis of gangliosides or sphingomyelin or both (Merrill et al., 1997; Schmelz et al., 1994). Since gangliosides and sphingomyelin are incorporated into lipoproteins and chylomicrons (Hara et al., 1987; Merrill et al., 1995), dietary gangliosides, sphingomyelin and/or their intestinal metabolites are likely to be transported throughout the body to affect sphingolipid biosynthesis in other organs (Vesper et al., 1999). Studies have suggested a possible interaction between sphingolipids and phospholipids (Merrill et al., 1997; Schmelz et al., 1994; Ogura et al., 1988). Sphingosine-1-phosphate is metabolized into ethanolamine phosphate and hexadecanal, both prerequisite materials for phospholipid synthesis (Merrill et al., 1997; Schmelz et al., 1994). Radiolabeled ganglioside [$^3$H]sphingosine-GM1 when injected intraperitoneally into mice was incorporated into hepatocyte phospholipids in the EPL form (Ogura et al., 1988).

Ether Phospholipids.

To date, there has been no research investigating whether dietary gangliosides can be used for synthesis of EPL in the intestine or influence EPL synthesis in neuronal tissues. EPL have an ester linkage at the sn-2 position, but have an ether linkage, either to an alkyl or alkenyl group, at the sn-1 position. EPL tend to be enriched in mammalian intestinal and neuronal cells (Paltauf, 1972). One type of EPL known as plasmalogens (a group of 1-O-alkenyl-2-acyl-glycero-phospholipids), accounts for about 75% of ethanolamine phosphoglycerides (EPG) in myelin of rat brain, 65% of EPG in human brain (Horrocks, 1972) and 12% of EPG in rat intestinal mucosa (Paltauf, 1972). High content of EPL may contribute to maintenance of cell integrity and function (Alonso et al., 1997; Bittman et al., 1984; Diomede et al., 1993; Honma et al., 1981; Mavromoustakos et al., 2001; Oishi et al., 1988; Paltauf, 1994; Principe et al., 1994; Seewald et al., 1990; and Zheng et al., 1990). EPL can affect membrane properties such as permeability (Bittman et al., 1984) and fluidity (Paltauf, 1994). EPL influence signal transduction to many metabolic pathways by protein kinase C (PKC) (Zheng et al., 1990), Na—K-ATPase (Oishi et al., 1988), inositol-lipid turnover (Seewald et al., 1990), and intracellular calcium (Alonso et al., 1997). EPL induce cell apoptosis (Alonso et al., 1997), cytotoxicity (Diomede et al., 1993; Honma et al., 1981), and antitumor activity (Mavromoustakos et al., 2001; Principe et al., 1994), which could have potential in anti-cancer applications. Selective cytotoxic effects of EPL is dependent on membrane cholesterol amount (Diomede et al., 1990). For example, HL60 cells with a high cholesterol content show lower uptake of EPL into membranes, resulting in decrease in membrane fluidity (Diomede et al., 1990) and higher rates of apoptosis (Diomede et al., 1993). Alkyl-lyso-phospholipids exhibit strong selective cytotoxicity in leukemia cells but not in normal bone marrow cells (Honma et al., 1981).

Gangliosides and EPL may perform similar functions. For example, both of these types of lipids localize in neuronal (Byrne et al., 1983; Svennerholm et al., 1989; and Horrocks 1972) and intestinal tissues (Forstner et al., 1973; Paltauf, 1972). Both gangliosides and EPL exhibit anti-cancer effects (Mavromoustakos et al., 2001; Principe et al., 1994; Schmelz et al., 2000) and contribute to cell differentiation (Ledeen et al., 1998; Honma et al., 1981) and apoptosis (Diomede et al., 1993; Malisan et al., 2002). Gangliosides and EPL are sensitive to membrane cholesterol content (Diomede et al., 1990; Blank et al., 1992).

In American diets daily intake of SPL (including gangliosides and sphingomyelin) is about 300 mg (Vesper et al., 1999) and daily intake of EPL is about 1 mg per gram of food (Berger et al., 2000). Neonates consume SPL and EPL from mothers milk (Diomede et al., 1991), but the metabolic interaction between dietary SPL and EPL is not known.

Cholesterol reduction in membranes causes increased EPL uptake (Diomede et al., 1990; Leikin et al., 1988) and increased activity of Δ-5 and Δ-6 desaturase enzymes (Clandinin et al., 1991). Dietary gangliosides may increase total membrane EPL content and accompanied with higher polyunsaturated fatty acid (PUFA) in subclasses of EPL. Sphingomyelin can be used as a control to compare bioavailability with gangliosides because sphingomyelin and gangliosides have the same ceramide molecule anchored in the cell membrane, but attached to a different head group. Using rats, the present data illustrated herein demonstrates that dietary ganglioside increases total content and composition of EPL containing PUFA in the developing intestine.

Microdomains.

Microdomains, generally called lipid rafts, caveolae, or glycosphingolipid-signaling domains, have been characterized as important domains for signal transduction and lipid (i.e. cholesterol) and protein trafficking (Anderson, 1998; Brown et al., 1998; Hakomori et al., 2000; and Simons et al. 1997). Microdomains are recently known as a site for the cellular entry of bacterial and viral pathogens (Fantini, 2000; Katagiri et al., 1999; and Bavari et al., 2002). For instance, the entry of filoviruses requires lipid rafts as the site of virus attack (Bavari et al., 2002). Cholera toxin entered the cell by endocytosis GM1 as the sorting motif necessary for retrograde trafficking into host cells and such trafficking depends on association with lipid rafts (Wolf et al., 2002).

Physiological and functional roles of microdomains are dependent on cholesterol and sphingolipids including gangliosides. Reduction of cholesterol inhibits pathogen entry by disrupting the structure of microdomains (Popik et al., 2002; Samuel et al., 2001) and impairs inflammatory signalling (Wolf et al., 2002; Triantafilou et al., 2002). Cholesterol upregulates the expression of caveolin, a marker of protein for caveolae (Fielding et al., 1997; Hailstones et al., 1998). Sphingolipid depletion inhibits the intracellular trafficking of GPI-anchored proteins and endocytosis via GPI-anchored proteins (Kasahara et al., 1999), suggesting that lipid-protein interaction directly modulates gene expression and cellular trafficking important for cell development and behaviour.

The neonatal intestine has permeable, endocytic and enzymatic transport systems for absorption of nutrients and immunoglobulins (Moxey et al., 1979; Wilson et al., 1991) but is susceptible to pathogen entry because of higher permeability than that of adults (Koldovsky 1994). High amount of gangliosides in mothers' milk during the neonatal period therefore act as a receptor for viral and bacterial toxins to protect entry of pathogens into enterocytes (Rueda et al., 1998). During development, membrane permeability gradually decreases (Koldovsky 1994) while peptidases and glycosidases become functionally active and enriched in microdomains (Danielsen et al., 1995). Many digestive/absorptive enzymes, such as alkaline phosphatase, aminopeptidase N and A, and sucrase-isomaltase are also increased in apical membrane microdomains (Stulnig et al., 2001). These results seem to suggest the importance of microdomains of intestinal apical membranes for nutrient uptake and metabolism.

Polyunsaturated fatty acids (20:5n-3 or 22:6n-3) can accumulate in microdomains and displace functional proteins by changing the lipid composition of the microdomain (Stulnig et al., 2001; Williams et al., 1999). This observation highlights the importance of dietary lipids in modulating physiological and biological properties of proteins in the microdomain. Little is known of how dietary gangliosides affect the lipid profile and protein components of microdomains during neonatal gut development.

Some previous studies have suggested that cholesterol depletion inhibits inflammatory signaling by disrupting microdomains structure (Wolf et al., 2002; Samuel et al., 2001; Triantafilou et al., 2002). However, it has not been evaluated whether diet-induced cholesterol reduction has any effect on decreasing cholesterol in the microdomain, disrupting microdomain structure and reducing pro-inflammatory mediators such as diglyceride (DG) and platelet activating factor (PAF). DG derived from phospholipids by phospholipase C, binds to protein kinase C (PKC) to phosphorylate targeted proteins, such as the epidermal growth factor receptor and DG resides in microdomains (Sciorra et al., 1999; Smart et al., 1995).

PAF, 1-O-alkyl-2-acetyl-sn-glycero-3-phosphorylcholine, stimulates inflammatory cells such as leukocytes (Prescott et al., 1990) and activates phospholipase A2 (PLA2) in the intestinal tissue to release arachidonic acid (Okayasu et al., 1987). Meanwhile, increased lyso-PC by PLA2 is further used for PAF synthesis with an acetylcholine transferase. PAF binds its receptor to increase intracellular calcium and inositol triphosphate (IP3) production and PKC activation for inflammation (Flickinger et al., 1999). It is unknown if PAF also localizes in the microdomain. Since several studies reported that sphingomyelin (SM), a sphingolipid, has an inhibitory effect on PLA2 activity (Koumanov et al., 1997), it was of interest to determine if dietary ganglioside also decreases PAF synthesis either by increasing sphingolipids or by disrupting microdomains structure in developing intestine. Whether dietary ganglioside reduces DG content in the microdomain was also examined since sphingosine, a derivative of sphingolipids inhibits PKC signaling which is required a structural complex with DG.

Neonates consume SPL including gangliosides from mothers milk (Carlson 1985; Berger et al., 2000). Gangliosides are known to act as receptors for viruses and toxins (Laegreid et al., 1987; Rolsma et al., 1998), activators for T-cells (Ortaldo et al., 1996) and stimulators for Th-1 and Th-2 cytokine-secreting lymphocytes in neonates (Vazquez et al., 2001). Gangliosides are also one of the major lipid components in microdomains. It is not known if dietary ganglioside changes the lipid profile and structure of the intestinal microdomain and modulating inflammatory signalling mechanisms in the developing intestine.

Necrotizing enterocolitis is an Inflammatory Bowel Disease of neonates and remains the leading gastrointestinal emergency in premature infants. Since current treatments disrupt the natural microflora, are invasive and do not target the specific processes underlying development of necrotizing enterocolitis, it remains the leading cause of morbidity and mortality in neonatal intensive care units. Prematurity, hypoxia-ischemia, infection and formula feeding are established risk factors, and breastfeeding is protective.

It is desirable to find a compound, a class of compounds, or composition active in treating inflammation. It is also desirable to find such compounds or compositions that is naturally occurring in the food supply, so as to more easily meet with public acceptance.

Further, it is desirable to find a compound, a class of compounds, or composition active in treating inflammation. Advantageously, such compounds or compositions would be naturally occurring in the food supply, so as to more easily meet with public acceptance.

References discussed herein are identified below:
Alonso et al., Brit. J. Pharmacol. 121 (1997) 1364-1368.
Anderson et al., Invest Ophthalmol. 15, 232-236 (1976).
Anderson, 1998; 67:199-225.
Andersson et al., FEBS Lett 1990; 269:15-8.
Asou et al., Neurosci. Res. 6 (1989) 369-375.
Aydin et al., Cell Biochem Funct 2000; 18:41-5.
Barbour et al., J. Cell. Physiol. 150, 610-619 (1992).
Basavarajappa et al., Clin. Exp. Res. 21 (1997) 1199-1203.
Bastiaanse et al., Cardiovasc Res 1997; 33:272-83.
Bauldry et al., J. Biol. Chem. 263 (1988) 16787-16795.
Bauldry et al., Biochim. Biophys. Acta 1084 (1991) 178-184.
Baumann et al., C. R. Acad. Sci. Hebd. Seances Acad. Sci. D. 283 (1976) 1113-1115.
Bavari et al., J Exp Med 2002; 195(5):593-602.
Belosevic et al., 1983. Exp. Parasitol. 56:93-100.
Bernett et al., J. Liq. Chromatogr. 8 (1985) 1573-1591.
Berger et al., J. Pediatr. Gastroenterol. Nutr. 30 (2000) 115-130.
Birch et al., Pediatr. Res. 44, 201-209 (1998).
Bittman et al., Biochim. Biophys. Acta 772 (1984) 117-126.
Blank et al., J. Nutr. 122 (1992) 1656-1661.
Bouhours et al., J. Biol. Chem. 258 (1983) 299-304.
Brown et al., 1992. Cell. 68:533-544.
Brown et al., Annu Rev Cell Dev Biol 1998; 14:111-36.
Buret et al., 1991. Parasitol Res. 77:109-114.
Byrne et al., J. Neurochem. 41 (1983) 1214-1222.
Carlson, Am J Clin Nutr 1985; 41:720-6.
Carlson et al., Pediatr. Res. 39, 882-888 (1996).
Carrie et al., Nutr. Neurosci. 5, 43-52 (2002).
Chen et al., Biochem J 1992; 286 (Pt 3):771-7.
Christiansen et al., Microvillus membrane vesicles from pig small intestine. Purity and lipid composition, Biochim. Biophys. Acta 647 (1981) 188-195.
Clandinin and Yamashiro, J. Nutr. 110 (1980) 1197-203.
Clandinin et al., FASEB J 1991; 5:2761-9.
Daniels et al., 1995. Parasitol Res. 81:143-147.
Danielsen et al., J Cell Biol 1995a; 131(4):939-50.
Danielsen, Biochemistry 1995b; 34(5):1596-605.
Daniotti et al., J. Neurosci. Res. 26, 436-446 (1990).
Daniotti et al., J. Neurochem. 62 (1994) 1131-1136.
De Maria et al., Science 1997; 277:1652-5.
Diamond et al., 1978. Trans. R. Soc. Trop. Med. Hyg. 72:431-432.
Diomede et al., Int. J. Cancer 46 (1990a) 341-346.
Diomede et al., Exp. Lung. Res. 16 (1990b) 507-519.
Diomede et al., Int. J. Cancer 49 (1991) 409-413.
Diomede et al., Int. J. Cancer 53 (1993) 124-130.
Dreyfus et al., Invest Ophthalmol. Vis. Sci. 37, 574-585 (1996).
Dreyfus et al., Indian J. Biochem. Biophys. 34, 90-96 (1997).
Faldella et al., Arch. Dis. Child. 75, F108-F112 (1996).
Fantini. Sphingolipid Metabolism and Cell Signaling, Pt A 2000; 311:626-38.
Farooqui et al., Chem. Phys. Lipids 106 (2000) 1-29.
Farthing. 1996. Giardiasis. Gastro. Clin. North Am. 25:493-515.
Fielding et al., Proc Natl Acad Sci USA 1997; 94(8):3753-8.
Flickinger et al., Am. J. Pathol. 1999; 154(5):1353-8.
Folch et al., 1957. J. Biol. Chem. 226:497-509.
Fontaine et al., Glycobiology 8, 183-190 (1998).
Forstner et al., Biochim. Biophys. Acta 306 (1973) 446-459.
Fujito et al., Neurosci. Res. 2, 407-411 (1985).
Furuchi et al., J Biol Chem 1998; 273:21099-104.
Gatt et al., J Biol Chem 1980; 255:3371-6.
Gibson et al., 1999. Exp. Parasitol. 92:1-11.
Gillin. 1987. Exp. Parasitol. 63:74-83
Gillin et al., 1985. Infect. Immun. 47:619-622.
Giusto et al., Neurochem. Res. 22, 445-453 (1997).
Gillon et al., 1982. Gut. 23:498-506.
Glickman et al., Biochim. Biophys. Acta 424 (1976) 17-25.
Guelman et al., Brain Res. 858 (2000) 303-311.
Hailstones et al., J Lipid Res 1998; 39(2):369-79.
Hakomori et al., Glycobiology 2000; 10(10):1086-7.
Hara et al., J. Biochem. 102 (1987) 83-92.
Ho et al., J. Neurochem. 46, 1176-1179 (1986).
Hoffman et al., J. Pediatr. 142, 669-677 (2003).
Hogyes et al., Neuroscience 119 (2003) 999-1012.
Holgersson et al., Biochimie 1988; 70:1565-74.
Hollan et al., C. R. Seances Soc. Biol. Fil. 192 (1998) 929-945.
Holmgren et al., 1985. Gasteroenterology. 89:27-35.
Holub et al., Nutritional regulation of cellular phosphotidylinositol, in: P. M. Conn and A. R. Means (Eds), Methods in Enzymology, Academic Press, New York, 1987, pp. 234-244.
Honma et al., Cancer Res. 41 (1981) 3211-3216.
Horrocks, Ether lipids, in: F. Snyder (Ed.), Content, Composition, and Metabolism of Mammalian and Avian Lipids that Contain Ether Groups, Academic Press, New York, 1972, pp. 177-272.
Huster, et al., Biophys. J. 78, 3011-3018 (2000).
Igarashi et al., Journal of Biological Chemistry 2000; 275 (41):32363-70.
Imaizumi et al., Nutr Res 1992; 12:543-8.
Incardona et al., Curr Opin Cell Biol 2000; 12(2):193-203.
Itoh et al., Anal Biochem 1986a; 154(1):200-4.
Itoh, et al., J. Physiol.-London 376, 231-252 (1986b).
Iwabuchi et al., Journal of Biological Chemistry 2000; 275 (20):15174-81.
Iwamori et al., 1984. J. Biochem. 95:761-770.
IUPAC-IUB, Commission on Biochemical Nomenclature: the nomenclature of lipids, Eur. J. Biochem. 79 (1977) 11-21.
Jarrol et al., 1981. Mol. Biochem. Parasitol. 2:187-196.
Jennnings et al., 1976. Aust. NZ J. Med. 6:556-560.
Jumpsen et al., Biochim Biophys Acta 1997; 1347(1):40-50.
Karlsson et al., J Neurochem 1978; 31:657-62.
Karlsson 1995. Curr. Opin. Structur. Bio. 5:622-635.
Kasahara et al., Biophysical Chemistry 1999; 82 (2-3):121-7.
Keenan et al., The structure of milk. In: Handbook of milk composition. Jensen R G, ed. Academic Press: New York, pp 5-85, 1995.
Keenan et al., Lipid phase. In: Fundamentals of Dairy Chemistry, 3rd ed. Wong N P, ed. Van Nostrand Reinhold Company: New York, pp 511-582, 1988.
Katagiri et al., Journal of Biological Chemistry 1999; 274 (49):35278-82.
Kobayashi et al., Nutr Res 1997; 17:111-4.
Koldovsky, Acta Paediatr Suppl 1994; 402:89-93.
Koumanov et al., Biochem J 1997; 326 (Pt 1):227-33.
Krajnc et al., J Pharmacol Exp Ther 1994; 271:1299-305.

Kyogashima et al., 1989. Arch. Biochem. Biophys. 270:391-397.
Laegreid et al., Life Sci 1987; 40(1):55-62.
Lazzaro et al., Exp Neurol 1994; 125:278-85.
Ledeen, Neurobiology of Glycoconjugates. New York: Plenum Press; 1989.
Ledeen et al., The role of GM1 and other gangliosides in neuronal differentiation. Overview and new finding, Ann. N.Y. Acad. Sci. 845 (1998) 161-175.
Leikin et al., Biochim. Biophys. Acta 963 (1988) 311-319.
Lencer et al., Journal of Cell Biology 1995a; 131(4):951-62.
Lencer et al., Proc Natl Acad Sci USA 1995b; 92:10094-8.
Leray et al., J. Neurochem. 54 (1990) 1677-1681.
Liu et al., J Biol Chem 1995; 270(45):27179-85.
Majoul et al., J Cell Biol 1996; 133(4):777-89.
Maekawa et al., J Biol Chem 1999; 274:21369-74.
Malewicz et al., Lipids 1990; 25:419-27.
Malisan et al., Biochim. Biophys. Acta 1585 (2002) 179-187.
Mather. Proteins of the milk-fat globule membrane. In: The mammary gland development, regulation and function. Neville M C, Daniel C W, eds. Plenum Press: New York, pp 217-267, 1987.
Mavromoustakos et al., J. Med. Chem. 44 (2001) 1702-1709.
Merrill et al., Toxicol. Appl. Pharmacol. 142 (1997) 208-225.
Mendez-Otero et al., Braz. J. Med. Biol. Res. 36, 1003-1013 (2003).
Merrill et al., J. Biol. Chem. 270 (1995) 13834-13841.
Mohand-Said et al., Stroke 28 (1997) 617-621.
Moran et al., Immunity 1998; 9:787-96.
Morgan et al., J Nutr 1980; 110:416-24.
Moxey et al., Anatomical Record 1979; 195(3):462-83.
Murphy et al., Biochim. Biophys. Acta 1167 (1993) 131-136.
Nilsson, Biochim. Biophys. Acta 164 (1968) 575-584.
Nishizawa et al., Int. J. Vitam. Nutr. Res. 73, 259-265 (2003).
Nixon et al., Biochim. Biophys. Acta 1347 (1997) 219-230.
Ogura et al., J. Biochem. 104 (1988) 87-92.
Oishi et al., Biochem. Biophys. Res. Commun. 157 (1988) 1000-1006.
Okayasu et al., J Lipid Res 1987; 28(7):760-7.
Ortaldo et al., Journal of Leukocyte Biology 1996; 60(4):533-9.
Ortega et al., Biochim Biophys Acta 1984; 773:231-6.
Ortega-Barria et al., 1994. J. Exp. Med. 94:2283-2288.
Paltauf, Chem. Phys. Lipids 74 (1994) 101-139.
Paltauf, Biochim. Biophys. Acta 260 (1972) 352-364. Reiner et al., 1986. J. Infect. Dis. 154:825-832.
Pan et al., Early Hum Dev 2000; 57:25-31.
Parker et al., J. Biol. Chem. 262 (1987) 5385-5393.
Parpal et al., J Biol Chem 2001; 276:9670-8.
Parton, J Histochem Cytochem 1994; 42:155-66.
Patton et al. Biochim Biophys Acta 415:273-309, 1975.
Perkkio et al., Pediatr Res 1980; 14:953-5.
Polit et al., Lipids 36 (2001) 927-935.
Popik et al., J Virol 2002; 76(10):4709-22.
Principe et al., Anticancer Drugs 5 (1994) 329-335.
Prinetti et al., Journal of Biological Chemistry 1999; 274(30):20916-24.
Prescott et al., J Biol Chem 1990; 265(29):17381-4.
Record et al., Biochim. Biophys. Acta 778 (1984) 449-456.
Reiss et al., Biochem. J. 323 (1997) 807-814.
Rietveld et al., Biochim Biophys Acta 1998; 1376:467-79.
Roberts-Thomson et al., 1976. Gastroenterology. 71:57-61.
Rohrer et al., 1986. Antimicrob. Agents Chemother. 30:254-257.
Rolsma et al., Journal of Virology 1998; 72(11):9079-91.
Rouser et al., Lipids 3 (1968) 284-287.
Rueda et al., 1996. Biol. Chem. 377:599-601.
Rueda et al., 1998a. J. Pediatr. 133:90-94.
Rueda et al., Early Human Development 1998b; 53:S135-S147.
Samuel et al. J Biol Chem 2001; 276:29319-29.
Sanchez-Diaz et al., J Pediatr Gastroenterol Nutr 1997; 24:405-10.
Schmelz et al., J. Nutr. 124 (1994) 702-712.
Schmelz et al., J. Nutr. 130 (2000) 522-527.
Sciorra et al., Molecular Biology of the Cell 1999; 10(11): 3863-76.
Seewald et al., Cancer Res. 50 (1990) 4458-4463.
Senn et al., Eur J Biochem 1989; 181:657-62.
Seyfried, et al., Mol. Cell. Biochem. 68, 3-10 (1985).
Simons et al., Nature 1997; 387(6633):569-72.
Sindelar et al., Free Radic. Biol. Med. 26 (1999) 318-324.
Slotte, Chem Phys Lipids 1999; 102:13-27.
Smart et al., Journal of Cell Biology 1995a; 131(4):929-38.
Smart et al., Molecular Biology of the Cell 1995b; 6:778.
Sonnino et al., Anal Biochem 1983; 128:104-14.
Sorice et al., 1996. Parasite Immunol. 18:133-137.
Stauffer et al., J Cell Biol 1997; 139:1447-54.
Stevens et al., 1997. Exp. Parasitol. 86:133-143.
Stulnig et al., Journal of Biological Chemistry 2001; 276(40): 37335-40.
Suzuki, 1964. Life Sci. 3:1227-1233.
Suh, Wierzbicici, and Clandinin, Dietary fat alters membrane composition in rod outer segments in normal and diabetic rats—impact on content of very long chain (C greater than or equal to 24) polyenoic fatty acids. BBA-Lipid Lipid Met. 1214, 54-62 (1994).
Sun et al., J Gerontol 1972; 27:10-7.
Svennerholm. Biochimica et Biophysica Acta 1957; 24:604-11.
Svennerholm, J. Neurochem. 10 (1963) 613-623.
Svennerholm, The gangliosides. Journal of Lipid Research 1964; 5:145-55.
Svennerholm et al., Biochim. Biophys. Acta 1005 (1989) 109-117.
Takamizawa et al., Biochim Biophys Acta 1986; 879:73-7.
Thompson et al., Biochem. Pharmacol. 56 (1998) 591-597.
Triantafilou et al., J Cell Sci 2002; 115 (Pt 12):2603-11.
Underdown et al., 1981. J. Immunol.; 126:669-672.
Vanier et al., J Neurochem 1971; 18:581-92.
Vazquez et al., Biofactors 15 (2001) 1-9.
Vesper et al., J. Nutr. 129 (1999) 1239-1250.
Walterspiel et al., 1994. Pediatrics. 93:28-31.
Watarai et al., 1995. J. Vet. Med. Sci. 57:17-22.
Welte et al., J Immunol 1987; 139:1763-71.
Williams et al., Journal of Neurochemistry 1980; 35(1):266-9.
Williams et al., Biochimica et Biophysica Acta-Biomembranes 1999; 1418(1):185-96.
Wilson et al., Journal of Cell Science 1991; 100:133-43.
Wolf et al., Journal of Biological Chemistry 2002; 277(18): 16249-56.
Wolfe 1992. Clin. Microbiol. Rev. 5:93-100.
Xi et al., J. Nutr. Sci. Vitaminol. 49, 210-213 (2003).
Yamamura et al., Biochem Biophys Res Commun 1997; 236 (1):218-22.
Zheng et al., Cancer Res. 50 (1990) 3025-3031.

Abbreviations used herein are as follows:

CPG: Choline phosphoglycerides; DG: diacylglycerol; *E. Coli: Escherichia coli*; EPG: Ethanolamine phosphoglycerides; EPL: Ether phospholipids; Gang-High: High concentration of ganglioside; Gang-Low: Low concentration of ganglioside; GD1b: II3 (NeuAc)$_2$-GgOse$_4$Cer; GD3: Ganglioside GD3: II$^3$ (NeuAc)$_2$-LacCer; GLC: Gas liquid chromatography; GG: gangliosides; GM1: Ganglioside GM1: II$^3$ NeuAc-GgOse$_4$Cer; GM2: Ganglioside GM2: II$^3$ NeuAc-GgOse$_3$Cer; GM3: Ganglioside GM3: II$^3$ NeuAc-LacCer; LCPUFA: Long chain polyunsaturated fatty acids; LPC: lysophosphatidylcholine; LPE: lysophosphatidylethanolamine; MUFA: monounsaturated fatty acids; NANA: N-Acetyl neuraminic acid; PAT: platelet activating factor; PBS: Phosphate buffered saline solution; PC: phosphatidylcholine; PE: phosphatidyl ethanoloamine; PI: phosphatidylinositol; PKC: Protein kinase C; PL, phospholipids; PS: phosphatidylserine; PUFA: polyunsaturated fatty acids; SEM: Standard error of the mean; SFA: Saturated fatty acids; sIgA: Secretory immunoglobulin A; SM: sphingomyelin; SPL: Sphingolipids; TG: Triglyceride; and TLC: Thin layer chromatography. Additional abbreviations include: PL=phospholipid, ROS=reactive oxygen species, COX-2=cyclooxygenase-2, 5 LOX=5 lipoxygenase, nNOS=neuronal nitric oxide synthase, iNOS=inducible nitric oxide synthase. BNIP3=bcl-2 nineteen kilodalton interacting protein 3, GM-CSF=granulocyte macrophage-colony stimulating factor.

SUMMARY

It is an object to provide methods for treating Inflammatory Bowel Disease.

A method is provided herein for treating Inflammatory Bowel Disease in a subject in need thereof, the method comprising administering a formulation comprising at least one ganglioside to the subject, wherein the formulation comprises at least about 50% GD3 by weight of total ganglioside content.

The formulation used in the method may additionally include gangliosides GM1, GM2, GM3, or GD1b.

The formulation may be prepared for oral consumption, and may be in the form of a ganglioside supplemented liquid or food, containing for example 0.01 to about 1000 ppm ganglioside.

In the example where the food comprises milk having a fat fraction of from 1 to 4% by weight, the fat fraction may comprise from about 0.1% to about 2.0% by weight ganglioside.

Exemplary formulations may include about 70% to about 90% GD3 and/or from about 0% to about 15% GM3 by weight based on total gangliosides. A level of about 80% GD3 and/or about 5% GM3 by weight based on total gangliosides may be used. Further, the ganglioside fraction may include about 10% GD1b by weight of total ganglioside content.

The formulation may be administered to provide from about 1 mg/day to about 10 g/day of ganglioside. For example, a level of from about 5 mg/day to about 500 mg/day of ganglioside may be provided.

Inflammatory Bowel Disease is considered to comprise Crohn's disease and/or ulcerative colitis.

The lipid components in microdomains may be altered by a reduction in platelet activating factor (PAF), a reduction in the ratio of cholesterol to sphingolipid, or a reduction in total diglyceride in the microdomains.

Other aspects and features will become apparent to those ordinarily skilled in the art upon review of the following description of specific embodiments described herein in conjunction with the accompanying figures.

BRIEF DESCRIPTION OF THE DRAWINGS

Embodiments will now be described, by way of example only, with reference to the attached Figures, wherein:

FIG. 3 shows the fatty acid composition of alkenylacyl, alkylacyl and diacyl subclasses in CPG in intestinal mucosa of animals fed control diet or treatment diets.

FIG. 4 shows the fatty acid composition of alkenylacyl, alkylacyl and diacyl subclasses in EPG in intestinal mucosa of animals fed control diet or treatment diets.

FIG. 7 shows the ratio of cholesterol/GG (A) and cholesterol/SM (B) in intestinal microdomains after feeding different diets for 2 wks.

FIG. 8 shows caveolin content determined by western blotting (A), and the intensity of blots (B) in intestinal microdomains fed control diet or treatment diets for 2 wks.

DETAILED DESCRIPTION

Figure 1:
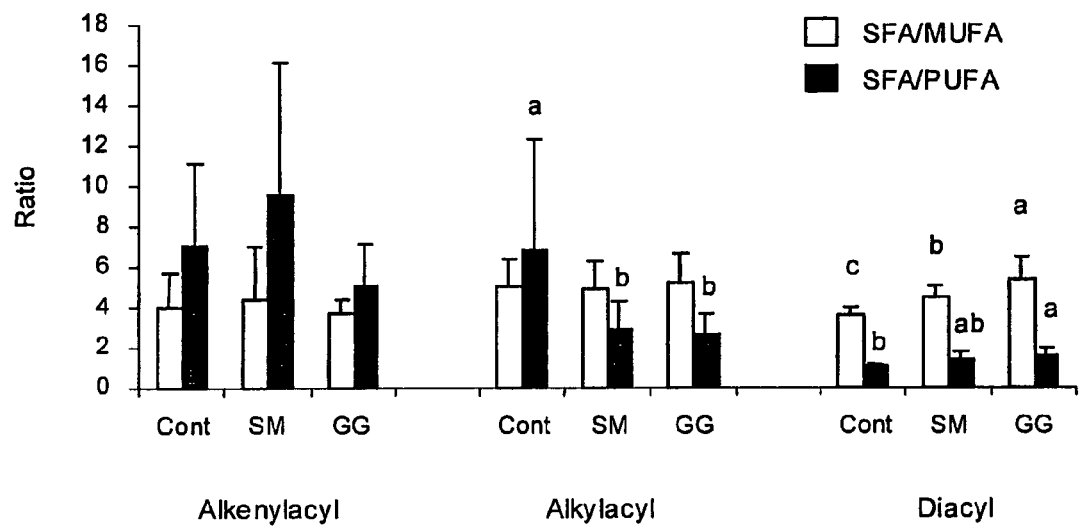
FIG. 1 illustrates the ratio of SFA to MUFA (white columns) and SFA to PUFA (black columns) in alkenylacyl-, alkylacyl- and diacyl subclasses in CPG in intestinal mucosa of animals fed control or treatment diets.

Generally, there is provided methods and formulations for treating Inflammatory Bowel Disease.

It has been found that a ganglioside-containing composition, such as a milk derived dietary component, alters inflammation mediators and has an effect in cholesterol lowering. Inflammation mediation occurs particularly in the intestine, the retina or other neural tissue According to embodiments described herein, a formulation is provided for treating Inflammatory Bowel Disease.

Inflammatory Bowel Disease, as described herein, encompasses bowel disorders attributable to inflammation, and specifically Crohn's disease and ulcerative colitis, which are collectively known as Inflammatory Bowel Disease.

By "treating" it is meant treatment of a patient who is in remission to prevent relapse or recurrence, or treating Inflammatory Bowel Disease when a patient is in an active state. Alleviation of symptoms, maintenance of a remission state, reduced frequency or severity of relapse, and enhanced quality of life may each be individually assessed to evaluate efficacy of treatment. Various parameters, as would be apparent to a physician or other skilled worker knowledgeable in the field of Inflammatory Bowel Diseases, such as Crohn's disease of ulcerative colitis can readily be evaluated.

The formulations described herein may include a ganglioside such as GD3, GM1, GM2, GM3, and GD1b. The formulation may be in the form of a supplemented liquid or food, such as infant formula or infant foods. An exemplary formulation may a total ganglioside composition made up of the following individual components: about 80% GD3, 9% GD1b, and 5% GM3 on a weight/weight basis. A further exemplary formulation may have one additional predominant ganglioside, aside from GM3, for example: GM1, GM2, GM3, and GD1b, that comprises more than 50% of the remaining total ganglioside content.

An embodiment described herein relates to a method for treating inflammation in a subject in need thereof comprising the step of providing at least one ganglioside to the subject for oral consumption. The use of at least one ganglioside for preparation of a medicament for oral consumption to mediate inflammation in a subject in need thereof is also encompassed by an embodiment described herein.

Further, an embodiment described herein encompasses a method for reducing blood cholesterol in a subject in need thereof comprising the step of providing at least one ganglioside to the subject for oral consumption. Additionally, the use of at least one ganglioside is described, for preparation of a medicament for oral consumption to reduce blood cholesterol in a subject in need thereof.

Experiments were done to assess the effects of dietary gangliosides, for example: components isolated from milk, on a variety of parameters indicative of or causal in treating an inflammatory or anti-inflammatory response. These experiments lead to the identification of gangliosides responsible for prophylactic and/or therapeutic effects.

A ganglioside fraction, for example a fraction derived from milk, herein referred to as "Fraction A" may be used. Other sources of gangliosides, such as from dairy products or synthetic sources, may also be used in preparing the formulations described.

The dosage amount of the ganglioside formulation used for oral delivery can easily be determined by one of skill in the art. A daily or one-time only minimum dosage may be from microgram to milligram quantities. A higher level may have a greater effect where the exposure and likelihood of infection is increased. A formulation in food or fluid form having from about 0.01 to about 1000 ppm, for example, a range from about 0.05 to about 100 ppm, a range from about 0.1 to about 100 pmm, or a range from about 0.1 to about 10 ppm of one or more ganglioside can be delivered to a subject in need thereof. An effective concentration falling outside of these ranges may also be used. No upper limit is required because the formulation does not display toxicity, and is not know to be toxic.

An exemplary level of ganglioside supplementation into a milk product may be at a level of from about 0.1% to about 2% (by weight), for example: about 0.4% ganglioside (by weight) within the butter fat fraction of a fluid milk. The fluid milk may contain 1% butter fat, 2% butter fat, 3% butter fat, 4% butter fat, or more. Thus, for example, a typical fluid milk containing 2% butter fat can be supplemented with ganglioside so that the fat fraction of the supplemented milk product comprises 0.4% ganglioside.

To accomplish the effect of treating Inflammatory Bowel Disease, a typical dosage for adults may be from about 10 mg to about 100 mg of ganglioside per person per day, and may be increased to about 1 g per day, for example, based on an adult body weight of about 70 kg. An effective amount of ganglioside may be delivered in a quantity ranging, for example, from about 1 mg/day to about 10 g/day, from about 5 mg/day to about 1 g/day, from about 10 mg/day to about 1 g/day, from about 5 mg/day to about 500 mg/day, or from about 100 mg/day to about 1 mg/day. An exemplary effective amount of 40 mg of ganglioside per day may be provided. Such quantities may be effectively delivered orally or by enteral feeding to an individual in need thereof.

For an infant having a typical body weight of about 3.5 kg, a level of gangliosides that may be delivered in order to accomplish an inflammation treating effect may range from about 0.1 mg/day to about 100 mg/day. Exemplary ranges include from about 0.5 mg/day to about 50 mg/day, from about 0.5 mg/day to about 10 mg/day, from about 1.0 mg/day to about 10 mg/day, per infant. However, it is possible to deliver an effective level of gangliosides in a quantity outside of this range, such as for example about 0.05 mg/day to about 1 mg/day may be delivered in order to accomplish an inflammation treating effect.

Fraction A may be prepared by crude processes, or may be obtained commercially from a source such as New Zealand Dairy, New Zealand. Fraction A is of variable lipid composition, for example, approximately 80% GD3; 9% GD1b, and 5% GM3 by weight, the remaining 6% being comprised of other gangliosides. Fraction B, higher in GM3 can also be prepared depending on the milk used for ganglioside isolation.

Other molecular forms of this complex lipid may be derived with similar or even greater bioactive characteristics. According to one possible composition of the formulation, the fraction may contain one or more gangliosides, such as for example GD3, GM1, GM2, GM3, GD1b, NANA, and sialic acid and is bioactive against *Giardia* producing very high kill rates.

Certain components of the formulation can be isolated from components of the present food supply, and thus would not need drug approval to be added to or to enriched new foods.

Ganglioside supplementation, or supplementation of a lipid fraction containing ganglioside can be used to supplement or fortify existing foods, such as in infant formulas, baby foods, baby cereals, and follow-on formulas which may be used for children up to about 18 months of age. Further, supplementation may also be useful in juices or other fluids packaged particularly for toddlers or older children, or in cereals as a coating or powdered sprinkle. Such foods may advantageously be those which are appealing to children, as this could be used to treat or prevent inflammatory disease at an early age, or to mediate inflammation.

Foods appealing to adults may also be supplemented or fortified with gangliosides or ganglioside-containing fractions in order to target individuals requiring mediation of an inflammatory response. The use of such foods, in treating Inflammatory Bowel Disease or to lower blood cholesterol level, is also envisioned. Typical foods to be supplemented may already include a fat-containing fraction, within which gangliosides are soluble. Exemplary foods include milk, cheese, yogurt, spreads, such as margarine. Further, supplementation may be employed using blending to maintain gangliosides in suspension or emulsion. Blender drinks, for example, may be used. Solids or semi-solid foods may also be supplemented.

In addition to being supplemented into food, the formulation may be provided in a liquid, gel, powder, tablet, pill or capsule form. Tablet, pill or capsule form may appeal to older children and adults, and would avoid the need to consume a food or beverage.

The supplement may also be added to pet foods or supplements, or to foods directed to other domesticated animals. In some instances, it may also be desirable to supplement the formulation to livestock. Such a use of gangliosides would be helpful in treating an inflammatory response in animals in need thereof.

Example 1

Milk Fraction A Containing Gangliosides

Table 1 provides the composition of Fraction A, illustrating the amount of total lipid, calcium and lactose present in 100 g of Fraction A on a dry weight basis. The ganglioside and phospholipid content of the lipid fraction is broken down into specific components. In Table 1, all abbreviations used are those defined previously, and additionally: % GG means percent of total gangliosides; % PL means percent of total phospholipids; x-1, x-2 and x-3 are gangliosides; LPC: lysophosphatidylcholine; SM: sphingomyelin; PC: phosphatidylcholine; LPE: lysophosphatidylethanolamine; PS: phosphatidylserine; PI: phosphatidylinositol; PE: phosphatidyl ethanoloamine.

TABLE 1

| Composition of Fraction A Fraction A 100 g Total Lipids (g) 23.00 | | |
|---|---|---|
| | (g) | |
| Gangliosides (as NANA amt) | 0.82 | (% GG) |
| GM3 | | 4.50 |
| x-1 | | 4.60 |
| x-2 | | 0.80 |
| GD3 | | 79.90 |
| GD1b | | 9.00 |
| x-3 | | 1.20 |
| PL (as 'P') | 0.49 | (% PL) |
| LPC | 0.036 | 7.3 |
| SM | 0.013 | 2.7 |
| PC | 0.012 | 2.5 |
| LPE | 0.093 | 19.0 |
| PS | 0.149 | 30.4 |

TABLE 1-continued

| Composition of Fraction A Fraction A 100 g Total Lipids (g) 23.00 | | |
|---|---|---|
| | (g) | |
| PI | 0.136 | 27.8 |
| PE | 0.050 | 10.2 |
| | 0.49 | 99.9 |
| Neutral lipid | 0.04 | |
| Cholesterol | 0.08 | |
| Ca (g) | 10.00 | |
| Lactose (g) | 65-70 | |

Example 2

Separation of Gangliosides from Fraction A

Fraction A, having the composition described above in Table 1, Example 1, was obtained and gangliosides were separated therefrom using the following method. The separated ganglioside fraction so obtained may be used in a supplementation. Alternatively, individual gangliosides obtained from the separated fraction may be used in a supplementation regime.

Total lipids were extracted from the ganglioside enriched preparation of Fraction A using the Folch method (Folch and Sloane-Stanley, 1957). The ganglioside-containing upper phase was transferred and the lower phase was washed once with Folch upper phase solution (chloroform/methanol/water, 3/48/47 by vol.). The combined ganglioside-containing fractions were passed through Sep-Pak™ C18 reverse-phase cartridges (Waters Corporation, Milford, Mass., USA), eluted with methanol and chloroform and methanol 2:1 (v/v), and dried completely under vacuum at 23° C. using a rotary evaporator. Ganglioside (NANA) content was measured as described by Suzuki (1964).

Example 3

Dietary Gangliosides Increase Content of Ether Phospholipids Containing 20:4n-6 and 22:6n-3 in the Rat Intestine In this Example, the effect of dietary gangliosides on the content of ether phospholipids (EPL) in intestinal mucosa was observed. Male Sprague-Dawley rats (18-day old) were fed a semi-purified diet consisting of 20% fat as a control diet. Two experimental diets were formulated by adding either 0.1% (w/w) gangliosides (GG diet) or 0.2% (w/w) sphingomyelin (SM diet) to the control diet. Fatty acid methyl esters from the alkenylacyl, alkylacyl, and diacyl subclasses of phospholipids were measured to determine total and relative percentage of EPL comprising the choline phosphoglyceride (CPG) and ethanolamine phosphoglyceride (EPG) fractions. The GG diet was shown to increase the overall levels of EPL in both CPG and EPG in intestinal mucosa as well as increasing the PUFA content of the EPL class, specifically in 20:4n-6 and 22:6n-3. As a result of the increase in PUFA content, the ratio of SFA to PUFA in both CPG and EPG was reduced in animals fed the GG diet. The effects of the SM diet were similar but of lesser magnitude than the GG diet. Enhanced EPL content may suppress carcinogenesis, inflammation and lipid oxidative processes in the developing intestine.

Materials and Methods

Animals and diets. The protocol for this study was approved by the Animal Care Committee at the University of Alberta, Canada. Male Sprague-Dawley rats (18-day old, 40±4.5 g) were housed in polypropylene cages and maintained at a constant room temperature of 23° C. and a 12 h light/dark cycle for 2 weeks. Animals had free access to water and were randomized to be fed one of three semi-purified diets containing 20% (w/w) fat (Table 2). The composition of basal diet is reported elsewhere (Clandinin et al., 1980). The fat in the control diet was a blend of triglycerides reflecting the overall fat composition of an infant formula. Two experimental diets were formulated by adding either sphingomyelin (0.2% w/w, Sigma, Mo., USA; SM diet) or a ganglioside enriched lipid powder (0.1% w/w, New Zealand Dairy, New Zealand; GG diet) to the control diet. The ganglioside enriched lipid powder consisted of about 45-50% (w/w of total lipid) as phospholipid and 15-20% (w/w of total lipid) as gangliosides. The ganglioside fraction contained about 80% (w/w) GD3 and GD1b, GM3 and other gangliosides (9, 5 and 6% w/w, respectively). The fatty acid composition of experimental diets was quantitatively analyzed by gas liquid chromatography (GLC, Varian Vista 3400CX). The fatty acid composition was consistent among the three diets: 18:1n-9 (50%), 18:2n-6 (20%), 16:0 (16%), 18:0 (8%), 18:3n-3 (2.8%) and other fatty acids (3.2%). The control diet and experimental diets provided an n-6 to n-3 ratio of 7.1. The cholesterol amount was low (<0.35%, w/w of total lipid). Overall the GG diet contained 19.6% triglycerides, 0.1% gangliosides, 0.2% phospholipid and 0.07% cholesterol (Table 2). Body weight and food intake was measured every other day throughout the experiment.

TABLE 2

Composition of experimental diets[1]

|  | Control | SM | GG |
|---|---|---|---|
| Basal diet (g/100 g) | 80.0 | 80.0 | 80.0 |
| Triglyceride | 20.0 | 19.8 | 19.6 |
| Sphingomyelin | — | 0.2 | tr[2] |
| Ganglioside | — | — | 0.1 |
| Phospholipid | — | — | 0.2 |
| Cholesterol | — | — | tr |

[1]The composition of the control diet are referred from Clandinin et al., 1980, representing an existing infant formula.
[2]tr presents trace amount.

Collection of Intestinal Mucosa.

After anesthetizing animals with halothane, the small intestine (jejunum to ileum) was excised. The intestine was washed with 0.9% cold saline solution to remove visible mucus and debris, opened, and moisture was carefully removed. Intestinal mucosa was scraped off with a glass slide on an ice cold glass plate. All samples were weighed and kept in a −70° C. freezer until used.

Lipid Extraction and Phospholipid Separation.

Total lipid was extracted by using the Folch method (Folch et al., 1957). For extracting total lipid, the intestinal mucosa was washed twice with Folch lower phase solution (chloroform/methanol/water, 86:14:1, v/v/v). The lower phase lipid was pooled, dried and then dissolved in chloroform:methanol (2:1, v/v). Extracted lipid was applied onto pre-coated silica gel "H" thin layer chromatography (TLC) plates (Analtech, Newark, Del.) and developed in the solvent (chloroform/methanol/2-propanol/0.25% KCl/triethylamine, 45:13.5:37.5:9:27, v/v/v/v/v) to separate individual phospholipid classes. After spraying with 0.1% ANSA (anilino naphthalene sulfonic acid) and identifying CPG and EPG bands under UV light, the two bands were scraped into test tubes.

Fatty Acid Composition and Quantification.

Solid phases containing CPG and EPG were eluted with 5 mL of chloroform:methanol (2:1) and then dried under $N_2$. The dried phospholipids were dephosphorylated with phospholipase C (B. cereus, Sigma Chemical Co., St. Louis, Mo.) at 37° C. for 2 hr in a solution of 1 mL diethyl ether, 4 mL 17.5 mM Tris buffer (pH 7.3), and 1.3 mL 1% $CaCl_2$ (Bernett et al., 1985). After extraction of the hydrolyzed lipids with diethyl ether and petroleum ether, lipids were acetylated in 0.1 mL of pyridine with 0.5 mL of acetic anhydride at 80° C. for 1 hr. The acetylated derivatives of alkenylacyl, alkylacyl and diacyl phospholipids were extracted with chloroform/methanol (2:1) solution, applied onto a silica gel high performance TLC plate (HPTLC, Whatman Inc, Clifton, N.J.) and developed in petroleum ether: diethyl ether: acetic acid, (90:10:1, v/v/v) to a migration distance of 10 cm from the solvent line, followed by a second development in toluene (Holub et al., 1987). The plate was sprayed with ANSA and visualized under UV light. Three subclasses of the CPG and EPG fractions scraped from the plate were then methylated in 3N-methanolic-HCl (Supelco, PA, USA) for 16 hr at 70° C. with a known amount of heptadecanoic acid as an internal standard. The fatty acid composition of each of the six fractions was analyzed by GLC equipped with a flame ionization detector and BP-20 fused capillary column (SGE, Australia). The flow rate of helium gas was 1.6 mL/min and the oven, injector and detector temperatures were 200° C., 250° C., and 250° C., respectively. Since only acylated fatty acids (not ethers) can be converted to fatty acid methyl esters for GLC analysis, the fatty acid amount measured in EPL only represents one-half of the total. Thus, this value was multiplied by two to have total and molecular percentage of EPL.

Statistical Analysis.

The values were shown as means±standard deviation from eight animals, with a few exceptions indicated. Significant differences between the control group and experimental groups were determined by one-way analysis of variance (ANOVA) with the SAS system. Effects of diet treatment were determined by a Duncan multiple range test at significance levels of $P<0.05$, $P<0.01$, $P<0.001$ or $P<0.0001$.

Results

Animal Growth and Intestinal Mucosa.

Initial body weight of animals, weight after two weeks of diet treatment was not significantly different between experimental and control groups: Intestinal mucosal weight and length was not affected by dietary treatment. Food consumption was also not influenced by diet treatment.

Fatty Acid Content Corresponding to Alkenylacyl, Alkylacyl and Diacyl Phospholipids in CPG and EPG.

Animals fed the GG diet presented significantly higher amount of fatty acids from alkenylacyl-CPG, alkenylacyl-EPG and alkylacyl-EPG in comparison with control animals (56%, 77% and 54% increases, respectively; Table 3). The highest change in fatty acid content relative to the control was observed in alkenylacyl-EPG ($P<0.0008$). In animals fed dietary gangliosides, a significant decrease in diacyl-CPG occurred, whereas no change was observed in diacyl-EPG. Animals fed the SM diet exhibited a similar increase in fatty acid content corresponding to alkylacyl-GPE, but no change occurred in the other subclasses of GPC and GPE. In the total fatty acid content of EPL (alkenylacyl and alkylacyl together), the GG diet produced significant increase, by 36% and 66% respectively, comprising CPG and EPG phospholipids in intestinal mucosa (Table 3). Feeding animals the SM diet only increased total EPL in EPG by 42% compared to control animals.

animals the GG diet achieved higher levels of alkenylacyl-EPG (12.5% versus 7.4%) and alkylacyl-EPG (10.9% versus 7.3%) with correspondingly lower levels of diacyl-EPG

TABLE 3

Fatty acid content of alkenylacyl, alkylacyl and diacyl subclasses in CPG and EPG from intestinal mucosa of animals fed experimental diets[1]

| Subclass (μg/g tissue) | Control | SM | GG | Effect of diet (P <) |
|---|---|---|---|---|
| Total EPL-CPG[2] | $31.8 \pm 6.7^b$ | $37.8 \pm 8.7^{ab}$ | $43.3 \pm 8.2^a$ | 0.05 |
| Alkenylacyl-CPG | $14.0 \pm 3.6^b$ | $17.0 \pm 3.0^{ab}$ | $21.8 \pm 7.2^a$ | 0.05 |
| Alkylacyl-CPG | $17.8 \pm 3.9$ | $20.8 \pm 7.5$ | $21.5 \pm 4.8$ | |
| Diacyl-CPG | $1.86 \times 10^3 \pm 344^a$ | $1.61 \times 10^3 \pm 469^{ab}$ | $1.22 \times 10^3 \pm 306^b$ | 0.01 |
| Total EPL-EPG | $68.1 \pm 7.9^c$ | $97.1 \pm 15.3^b$ | $113 \pm 20^a$ | 0.001 |
| Alkenylacyl-EPG | $34.4 \pm 7.7^b$ | $45.2 \pm 14.5^b$ | $60.9 \pm 12.3^a$ | 0.0008 |
| Alkylacyl-EPG | $33.7 \pm 4.4^b$ | $51.9 \pm 10.6^a$ | $51.8 \pm 10.7^a$ | 0.0006 |
| Diacyl-EPG | $774 \pm 99$ | $731 \pm 292$ | $801 \pm 174$ | |

[1]Mean ± SD from 7, 8, and 7 animals, for the Control, SM and GG group, respectively.
[2]Fatty acid content of total EPL (alkenylacyl and alkylacyl together) in CPG or EPG.

Changes in Relative Amounts of SFA, MUFA, and PUFA in Alkenylacyl, Alkylacyl and Diacyl Phospholipids Comprising CPG and EPG Classes.

As PUFA levels in alkylacyl-CPG increased in animals fed the GG diet, there was a concomitant decrease in the ratio of SFA to PUFA in alkylacyl-CPG (2.6 versus 6.8, P<0.05; FIG. 1). In contrast, in diacyl-CPG fractions, animals fed the GG diet exhibited an increase in the ratios of SFA to MUFA (5.3 versus 3.6, P<0.0007) and SFA to PUFA (1.5 versus 1.1, P<0.05).

FIG. 1 illustrates the ratio of SFA to MUFA (white columns) and SFA to PUFA (black columns) in alkenylacyl-, alkylacyl- and diacyl subclasses in CPG in intestinal mucosa of animals fed control or treatment diets. Values are means±SD of 7, 8 and 7 animals for the control, SM and GG diet, respectively. Letters represent a significant difference between groups at P<0.05, except for the ratio of SFA to MUFA in the diacyl subclass at P<0.0007.

Figure 2:
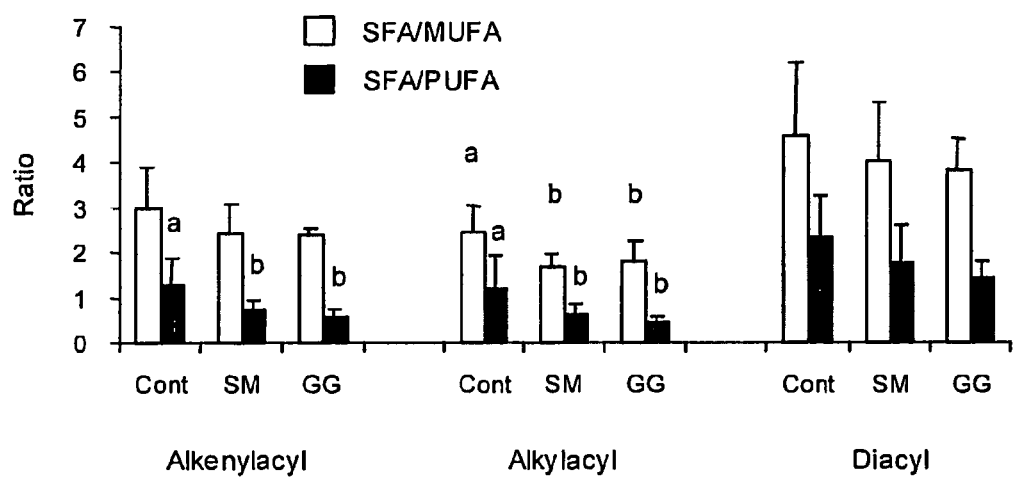
FIG. 2 illustrates the ratio of SFA to MUFA (white columns) and SFA to PUFA (black columns) in alkenylacyl-, alkylacyl- and diacyl subclasses in EPG in intestinal mucosa of animals fed control or treatment diets.

Changes in relative amounts of SFA, MUFA, and PUFA in the three subclasses of EPG are illustrated (FIG. 2). In the GG diet group, alkenylacyl-EPG and alkylacyl-EPG exhibited significantly lower ratios of SFA to PUFA compared to the controls (0.6 versus 1.3 for alkenylacyl-GPE, P<0.005, and 0.5 versus 1.2 for alkylacyl-GPE, P<0.05). There was also a decrease in the SFA/MUFA ratio (1.8 versus 2.5) in the alkylacyl group. Animals fed the SM diet exhibited a lower SFA/PUFA in the both EPL subclasses compared to animals fed the control diet, but effects were more subtle than that of the GG diet. There was no observed effect of SM or GG treatments on the diacyl-EPG class.

FIG. 2 shows the Ratio of SFA to MUFA (white columns) and SFA to PUFA (black columns) in alkenylacyl-, alkylacyl- and diacyl subclasses in EPG in intestinal mucosa of animals fed control or treatment diets. Values are means±SD of 7, 8 and 7 animals for the control, SM and GG diet, respectively. Letters represent a significant difference between groups at P<0.005, except for the ratio of SFA to PUFA in the alkylacyl subclass at P<0.02.

Changes in Relative Composition of Alkenylacyl, Alkylacyl and Diacyl Phospholipids Comprising CPG and EPG.

Animals fed the GG diet exhibited higher levels of alkenylacyl-CPG (3.3% versus 1.6%) and alkylacyl-CPG (3.2% versus 2.1%) with correspondingly lower levels of diacyl-CPG (93.5% versus 96.3%), compared to animals fed the control diet (Table 4). No effect of the SM diet was observed on the relative composition of CPG in the mucosa. Feeding (76.6% versus 85.3%), compared to animals fed the control diet. Animals fed the SM diet showed a relative increase in alkenylacyl-EPG, but the effect was less pronounced than in those fed the GG diet. There was no effect of the SM diet on alkylacyl-EPG. Relative to total phospholipids, animals fed the GG diet also exhibited a marked increase in total EPL (alkenylacyl and alkylacyl together) from 3.7% to 6.5% in CPG and from 14.7% to 23.4% in EPG (Table 4). Feeding the SM diet resulted in a relative increase in EPG, but not in CPG.

TABLE 4

Percentage of alkenylacyl, alkylacyl and diacyl subclasses in CPG and EPG from intestinal mucosa of animals fed experimental diets[1]

| Subclass (%, w/w) | Control | SM | GG | Effect of diet (P <) |
|---|---|---|---|---|
| Total-EPL-CPG[2] | $3.7 \pm 0.8^b$ | $4.8 \pm 1.1^b$ | $6.5 \pm 1.8^a$ | 0.006 |
| Alkenylacyl-CPG | $1.6 \pm 0.4^b$ | $2.2 \pm 0.8^{ab}$ | $3.3 \pm 1.3^a$ | 0.05 |
| Alkylacyl-CPG | $2.1 \pm 0.5^b$ | $2.6 \pm 0.6^{ab}$ | $3.2 \pm 0.8^a$ | 0.05 |
| Diacyl-CPG | $96.3 \pm 0.8^a$ | $95.2 \pm 1.1^a$ | $93.5 \pm 1.8^b$ | 0.007 |
| Total-EPL-EPG | $14.7 \pm 1.6^b$ | $20.4 \pm 5.4^a$ | $23.4 \pm 3.2^a$ | 0.001 |
| Alkenylacyl-EPG | $7.4 \pm 1.5^c$ | $10.2 \pm 2.1^b$ | $12.5 \pm 1.4^a$ | 0.0001 |
| Alkylacyl-EPG | $7.3 \pm 1.1^b$ | $10.2 \pm 3.7^{ab}$ | $10.9 \pm 2.5^a$ | 0.05 |
| Diacyl-EPG | $85.3 \pm 1.6^a$ | $79.6 \pm 5.4^b$ | $76.6 \pm 3.2^b$ | 0.002 |

[1]Mean ± SD from 7, 8, and 7 animals, for the Control, SM and GG group, respectively.
[2]Percent of total EPL (alkenylacyl and alkylacyl together) relative to total phospholipids in CPG or EPG. Changes in fatty acid composition of alkenylacyl-, alkylacyl- and diacyl-CPG Changes in Fatty Acid Composition of Alkenylacyl-, Alkylacyl- and Diacyl-CPG.

In comparison with control animals, animals fed the GG diet did not show significant change in the fatty acid composition of alkenylacyl-CPG except for 14:1, which decreased (FIG. 3). Animals fed the GG diet showed an increase in 20:4n-6 as compared to animals fed the SM diet. Decrease occurred in alkylacyl-CPG content of 18:0, 24:0 and 24:1 for animals fed the GG diet as well as a distinct increase in 22:6n-3 (P<0.0007). The SM diet produced a decrease in 18:0 and an increase in 22:6n-3 content. In diacyl-CPG, higher levels of 16:0 and 18:0 and lower levels of 18:1n-9 and 18:2n-6 were observed in animals fed the GG diet compared to control animals. Similar trends in 16:0, 18:1n-9 and 18:2n-6 were observed for animals fed the SM diet.

Changes in Fatty Acid Composition of Alkenylacyl-, Alkylacyl- and Diacyl-EPG.

The fatty acid composition of alkenylacyl-, alkylacyl, and diacyl-EPG in intestinal mucosa of animals fed experimental diets is illustrated (FIG. 4). Animals fed dietary gangliosides showed higher levels in alkenylacyl-EPG of 22:4n-6 (100% increase, P<0.001) and 22:6n-3 (71% increase, P<0.001) compared to controls, and lower levels of 16:0 and 18:0. Animals receiving the SM diet exhibited a similar change in 22:4n-6, 22:6n-3 and 16:0 fatty acid content, but the effect was smaller than observed for animals fed the GG diet. In alkylacyl-EPG, higher content of 20:4n-6, 22:4n-6, and 22:6n-3 (36%, 87% and 77% increases, respectively) was observed in animals fed the GG diet with a considerable reduction of saturated fatty acids 16:0, 18:0 and 24:0 relative to animals fed the control diet. In diacyl-EPG, dietary gangliosides increased the content of 20:4n-6 by 36%, relative to controls.

Changes in Total SFA, MUFA and PUFA Content of Alkenylacyl-, Alkylacyl- and Diacyl-CPG.

The fatty acid content of SFA, MUFA and PUFA in alkenylacyl-, alkylacyl-, and diacyl-CPG is shown (FIG. 3). Feeding animals the GG diet increased total PUFA content in alkylacyl-GPC, which rose by 63% compared to animals fed the control diet. No changes occurred in MUFA and SFA for this lipid subclass. Animals fed the GG diet had lower content of PUFA and MUFA and increased content of SFA in diacyl-CPG than observed for control animals. For animals given the SM diet, higher level of PUFA in alkylacyl-CPG lipids was found. These animals also exhibited lower MUFA and higher SFA contents in diacyl-CPG compared to controls.

Changes in Total SFA, MUFA and PUFA Content of Alkenylacyl-, Alkylacyl- and Diacyl-EPG.

Animals fed the GG diet exhibited increased content of PUFA in the three EPG lipid subclasses compared to control animals, (increase of 41% in alkenylacyl, 41% in alkylacyl and 30% in diacyl-EPG; FIG. 4). The increase in PUFA content was accompanied with a decrease in SFA content in alkenylacyl and alkylacyl-EPG. No change was observed in MUFA in alkenylacyl, alkylacyl or diacyl phospholipids. Feeding of the SM diet also resulted in increased content of PUFA and decreased content of SFA in alkenylacyl-EPG and alkylacyl-EPG compared to controls. No effect of the SM diet was detected in diacyl-EPG.

Changes in Relative Amounts of SFA, MUFA, and PUFA in Alkenylacyl, Alkylacyl and Diacyl Phospholipids Comprising CPG and EPG Classes.

As PUFA levels in alkylacyl-CPG increased in animals fed the GG diet, there was a concomitant decrease in the ratio of SFA to PUFA in alkylacyl-CPG (2.6 versus 6.8, P<0.05; FIG. 1). In contrast, in diacyl-CPG fractions, animals fed the GG diet exhibited an increase in the ratios of SFA to MUFA (5.3 versus 3.6, P<0.0007) and SFA to PUFA (1.5 versus 1.1, P<0.05).

Changes in relative amounts of SFA, MUFA, and PUFA in the three subclasses of EPG are illustrated (FIG. 2). In the GG diet group, alkenylacyl-EPG and alkylacyl-EPG exhibited significantly lower ratios of SFA to PUFA compared to the controls (0.6 versus 1.3 for alkenylacyl-GPE, P<0.005, and 0.5 versus 1.2 for alkylacyl-GPE, P<0.05). There was also a decrease in the SFA/MUFA ratio (1.8 versus 2.5) in the alkylacyl group. Animals fed the SM diet exhibited a lower SFA/PUFA ratio in the both EPL subclasses compared to animals fed the control diet, but effects were more subtle than that of the GG diet. There was no effect of SM or GG treatments observed on the diacyl-EPG class.

Discussion

Previous studies (Merrill et al., 1997; Schmelz et al., 1994; Ogura et al., 1988) showing a possible mechanism to convert gangliosides to EPL in vivo do not explain whether dietary gangliosides can be absorbed and then used for EPL synthesis. The present study confirms that dietary gangliosides can be utilized for biosynthesis of EPL in developing rat intestinal mucosa. There are two possible mechanisms which may explain this effect. Firstly, it is assumed that hexadecanal, a derivative of gangliosides, is directly utilized for the synthesis of EPL as a precursor of ether-linked fatty alcohols [Merrill et al., 1997; Schmelz et al., 1994]. This hypothesis is supported by a study showing that intraperitoneal injection of [$^3$H]GM1, labeled at the C-3 position of sphingosine, is converted into alkylacyl-EPG in the mouse liver [Ogura et al., 1988]. Secondly, a possible indirect mechanism is that reduction of cholesterol in intestinal cells caused by dietary gangliosides may increase EPL synthesis or uptake. Earlier studies show that a decrease in cholesterol content increase EPL uptake in human leukemia cell lines [Diomede et al., 1990; Diomede et al., 1991]. Since experiments have shown a significant decrease in total cholesterol content in the intestine of animals fed the GG diet, it is logical to assume that dietary gangliosides may increase EPL synthesis by decreasing intestinal cholesterol content.

Several studies have shown that EPL is enriched in neuronal tissues and may play a functional role in neuronal development [Horrocks et al., 1972; Hollan et al., 1998; Sindelar et al., 1999; and Farooqui et al., 2000]. For example, EPL, especially plasmalogen, dramatically increased during 3-90 days in rat cerebellum development [Leray et al., 1990] and within one year of birth in the human brain [Rouser et al., 1968]. Plasmalogen levels are also significantly higher during cell differentiation in N1E-115 neuroblastoma cells [Murphy et al., 1993]. EPL is a major phospholipid present during synaptogenesis and myelination [Leray et al., 1990; Rouser et al., 1968] in which EPL may act as an endogenous antioxidant for membrane peroxidation [Sindelar et al., 1999; Farooqui et al., 2000; and Reiss et al., 1997]. The present results suggest that dietary gangliosides may enhance development of the enteric nerve system during neonatal gut development by providing a means, for increasing EPL content.

Another possible implication of elevated EPL level is an effect on anti-inflammatory response. Alkylacylglycerol, an analogue of diacylglycerol (DG) which is derived from EPL by phospholipase C (PLC), is known to have a potent inhibitory effect on lipoxygenase [Bauldry et al., 1988] and cytosolic phospholipase A2 (cPLA2) activity [Nixon et al., 1997], both of which stimulate an inflammatory response. Alkylacylglycerol also decreases leukotriene B4 and 5-hydroxyeicosatetraenoic acid (5-HETE) production [Bauldry et al., 1991] by inhibiting PKC activity [Parker et al., 1987] compared to DG. Gangliosides also inhibit PLA2 activity [Basavarajappa et al., 1997]. This hypothesis is supported by the recent finding that dietary gangliosides decrease platelet activating factor (PAF) and DG in intestinal microdomains. Alkylacyl-phospholipids are mostly localized at the inner membrane [Record et al., 1984], Results showing a 52% and 49% increase in the level of alkylacyl-CPG and -EPG, respectively, suggest that dietary gangliosides may enhance the inner localization of EPL. This localization of the alkylacyl subclass of EPL at the inner membrane may influence anti-inflammatory response [Bauldry et al., 1988; Nixon et al., 1997; Bauldry et al., 1991; and Parker et al., 1987] by down-regulating cytosolic enzymes and proteins, such as cPLA2 and PKC, known to be inflammatory mediators.

Higher levels of PUFA in EPL in animals fed the GG diet may have resulted from a decrease in total cholesterol content in intestinal mucosa which is known to cause a corresponding increase of Δ-5 and Δ-6 desaturase activities [Leikin et al., 1988]. Finding that dietary gangliosides promoted a higher level of 20:4n-6, 22:4n-6 and 22:6n-3 in EPG raises the question of whether these PUFA may serve a particular function in the enteric nervous system as in other neuronal tissues. For example, 22:6n-3 protects retinal photoreceptors by delaying the onset of apoptosis and activates photoreceptor differentiation, promoting opsin expression and inducing apical differentiation in these neurons [Polit et al., 2001]. Supplementation of LC-PUFAs resulted in a resistance against NMDA-induced excitotoxic degeneration of cholinergic neurons in infant rats [Hogyes et al., 2003].

The present study demonstrates that dietary gangliosides increase total and relative percentage of EPL and the PUFA content of EPL in intestinal mucosa during neonatal development. These results suggest that dietary gangliosides influence gut development and protection by enhancing EPL content which may have a preventative role in carcinogenesis, inflammation, and lipid oxidation. Further investigation is needed to determine if dietary ganglioside also affects the synthesis of EPL in neuronal tissues such as brain, retina and the myenteric plexus in the intestine.

Example 4

Diet-Induced a Decrease in the Ratio of Cholesterol to Sphingolipids Attenuates the Caveolin and Inflammatory Mediator Content in Microdomains of the Rat Intestine Membrane microdomains rich in cholesterol and sphingolipids including gangliosides are known as cellular binding sites for various pathogens. Cholesterol depletion inhibits the cellular entry of pathogens and also reduces inflammatory signals by disrupting microdomain structure. Previous data show that dietary gangliosides increased gangliosides while decreasing cholesterol in the intestinal mucosa. It was hypothesized that diet-induced reduction in the cholesterol content in intestinal microdomains disrupts microdomain structure resulting in reduced pro-inflammatory signals. To test this hypothesis, Sprague-Dawley rats (18-day old) were fed semi-purified diets for 2 wks. The control diet contained 20% triglyceride. Experimental diets were formulated by adding either 0.1% ganglioside enriched lipid (GG diet, w/w of diet) or 1.5%, w/w total fatty acids, polyunsaturated fatty acid (PUFA diet, 1% 20:4n-6 and 0.5% 22:6n-3) as triglyceride to the control diet. The ganglioside enriched lipid contained 70-80% GD3 among the total ganglioside fraction. Levels of cholesterol, ganglioside, caveolin expression and pro-inflammatory mediators, platelet activating factor (PAF) and diglyceride (DG) was measured in microdomains. Feeding animals the GG diet increased GG and decreased cholesterol content in intestinal microdomains by 50% and 23%, respectively. These changes resulted in a significant decrease in the ratio of cholesterol to GG. Increased GD3 and decreased GM3 was found in the intestinal microdomains of animals fed the GG diet in comparison to animals fed the control diet. Caveolin content was significantly reduced in animals fed the GG diet along with reduction in PAF and DG content in the microdomain. Animals fed the PUFA diet also showed decreased cholesterol, caveolin, PAF and DG content in intestinal microdomains compared to animals fed the control diet, without change occurring in the sphingolipid profile. It is concluded that dietary GG decrease the cholesterol/GG ratio, caveolin, PAF and DG content in microdomains and may have a potential anti-inflammatory effect during gut development.

The objective of this example was to determine if cholesterol reduction in intestinal mucosa by dietary gangliosides consequently induces decreases in the ratio of cholesterol/ sphingolipids, structural disruption of microdomains and ultimately attenuates the level of pro-inflammatory mediators in developing gut.

Materials and Methods

Animals and Diets.

The experiments presented in this example were approved by the University of Alberta Animal Ethics Committee. Male Sprague-Dawley rats (18-day-old, n=24), average body weight 41.6±1.6 g, were randomly separated into 3 groups of 8 with 2 or 3 rats housed in each polypropylene cage. Animals were maintained at a constant temperature of 23° C. and a 12 h light/dark cycle. Animals had free access to water and one of three semi-purified diets containing 20% (w/w) fat for 2 weeks. The composition of the basal diets fed has been previously reported (Table 5) (Clandinin et al., 1980). Animal body weight and food intake were recorded every other day throughout the experiment. The control diet (CONT diet) fat was a blend of triglyceride, which reflected the fat composition of an existing infant formula. Fatty acids of the control diet (Jumpsen et al., 1997) were composed of about 31% saturated fatty acids, 48% monosaturated fatty acids and 21% polyunsaturated fatty acids providing a ratio of 18:2n-6 to 18:3n-3 of 7.1. Two experimental diets were formulated by adding either polyunsaturated fatty acids such as 1% arachidonic acid (20:4n-6) and 0.5% docosahexaenoic acid (22:6n-3) (PUFA diet, 1.5% w/w, Martek Biosciences, USA) or a ganglioside-enriched lipid (GG diet, 0.1% w/w, New Zealand Dairy, New Zealand) to the control diet. Ganglioside enriched lipid consisted of about 45-50% (w/w) phospholipids and 15-20% (w/w) gangliosides. The cholesterol content was negligible (<0.35% w/w total lipid). The ganglioside fraction contained about 80% w/w GD3 and GD1b, GM3 and other gangliosides (GM2, GM1 and GT1b) was 9, 5 and 6% w/w, respectively.

TABLE 5

Composition of Experimental Diets[1]

| | Diet Treatment | | |
|---|---|---|---|
| | Control | PUFA | GG |
| Basal diet (g/100 g) | 80.0 | 80.0 | 80.0 |
| Triglyceride | 20.0 | 20.0 | 19.6 |
| 20:4n-6 | — | 1.0 | — |
| 22:6n-3 | — | 0.5 | — |
| Ganglioside | — | — | 0.1 |
| Phospholipid | — | — | 0.2 |
| Cholesterol | — | — | tr[2] |

[1]The composition of the basal diet has been previously published (Clandinin et al., 1980). The fatty acid composition of the control fat blend is similar to that of an infant formula fat mixture (Jumpsen et al., 1997).
[2]tr presents trace amount.

Collection of Samples.

After anesthetizing animals with halothane, the small intestine (jejunum to ileum) was excised. The intestine was washed with ice cold 0.9% saline solution to remove visible mucus and dietary debris, opened and moisture was carefully removed with a paper towel to measure mucosa weight. Intestinal mucosa was scraped off with a glass slide on an ice cold glass plate. All mucosa samples were kept in a −70° C. freezer until extraction.

Sucrose Gradient Separation of Microdomains.

Intestinal microdomains were prepared by ultra-centrifugation of a discontinuous sucrose gradient (Igarashi et al., 2000). Intestinal mucosa was suspended with TME (10 mM Tris-HCl, 1 mM $MgCl_2$, 1 mM EGTA) solution containing 1 mM phenylmethyl sulfonyl fluoride, 0.001% w/v apotinin and 2% v/v Triton X-100 for 30 min in ice and homogenized with 15 strokes of a Dounce homogeniser with a tight-fitting pestle (Wheaton Scientific, USA). The homogenate was adjusted to 45% w/v sucrose by adding the equal vol of 90% w/v sucrose and then homogenized again with 5 strokes of the Dounce homogeniser. A 5-35% discontinuous sucrose gradient was overlaid on the homogenate in 45% w/v sucrose, which left a 45-35-5% sucrose gradient from the bottom. After 16 h centrifugation at 70,000×g at 4° C. in a Beckman SW 28 Ti rotor, interface fraction between 5 and 35% sucrose was collected as the microdomain fraction. Microdomains were washed with TME solution and centrifuged twice at 100,000×g for 1 h at 4° C. to remove sucrose and Triton X-100. The pellet was resuspended in phosphate buffer solution and used for protein and lipid analysis. Enrichment of microdomains was demonstrated by testing the amounts of cholesterol and gangliosides in the intestinal microdomain compared to the protein pellet which was soluble in detergent solution. In the intestinal microdomains, cholesterol content was 10 fold higher compared to the detergent soluble proteins. Intestinal gangliosides were exclusively found in the microdomain compared to negative intensity in the detergent soluble protein pellet by a densitometry assay on TLC plates.

Western Blotting for Caveolin Content.

Protein content from microdomains was measured by QuantiPro BCA™ Assay Kit (Sigma-Aldrich Co. MO. USA). Approximately 25 mg proteins were dissolved with SDS reducing sample buffer and loaded onto 15% SDS-PAGE minigels. After transferring proteins onto nitrocellulose membrane (Amersham Pharmarcia Biotech, UK), membranes were blocked with 5% non-fat dried milk in TBS-T (20 mM Tris; pH 7.6; 137 mM NaCl; 0.1% Tween-20) for 1 h at room temperature. The primary antibody (BD Biosceince, ON. CA), which specifically recognizes caveolin was diluted in TBS-T with 1% non-fat dried milk (1:1000) and incubated for 90 min at room temperature. The membrane was washed three times for 10 min each time in TBS-T. The secondary antibody (goat anti-mouse IgG-HRP conjugate; Bio-Rad, CA. USA) was diluted in 1% non-fat dried milk in TBS-T (1:2000) and incubated for 1 h at room temperature. After washing the membrane with TBS-T three times for 10 min each time, the caveolin protein was developed by enhanced chemiluminescence (ECL) detection reagent according to the protocol supplied by Amersham Pharmarcia Biotech, UK. Blot intensity of caveolin was measured from five animals from each diet group by using an Imaging Densitometer (Bio-Rad, CA. USA).

Ganglioside Extraction and Purification.

Total lipid of the microdomain fraction was extracted using the Folch method (Folch et al., 1957). For extraction of gangliosides (Svennerholm, 1964), the upper phase was collected into a test tube and the lower organic phase was washed twice with the Folch upper phase solution (chloroform/methanol/water, 3/48/47 by vol.) to increase GG content isolated from the microdomain fraction. The upper phase gangliosides were pooled and purified by passage through Sep-Pak™ C-18 cartridges (Waters Corporation, Milford, Mass., USA) prewashed with 10 ml of methanol, 20 ml of chloroform/methanol (2/1, v/v), and 10 ml of methanol as described by Williams and McCluer (Williams et al., 1980). The upper phase extract was loaded onto Sep-Pak C-18 cartridges. Cartridges were then washed with 20 ml of distilled water to remove salts and water-soluble contaminants. Gangliosides were eluted with 5 ml of methanol and 20 ml of chloroform/methanol (2/1, v/v), dried under $N_2$ gas and then redissolved with 500 ul of chloroform/methanol (2/1, v/v). Gangliosides were stored at −70° C. until analysis.

Analysis of Total and Individual Ganglioside Content.

Total NANA of gangliosides was measured as described by Suzuki (Suzuki, 1964). An aliquot of the ganglioside sample purified using Sep-Pak C-18 cartridges was dried under $N_2$ gas and dissolved with each of 0.5 ml of distilled $H_2O$ and resorcinol-HCl (Svennerholm, 1957) in screw-capped Teflon-lined tubes. The purple blue color developed by heating was extracted into butylacetate/butanol (85/15, v/v) solvent. Optical density was read by a spectrophotometer (Hewlett Packard, 8452A) at 580 nm. For quantification, N-acetyl neuraminic acid (NANA; Sigma, Mo., USA) was used as a standard and total ganglioside content is presented as NANA.

Individual gangliosides were separated by Silica gel high performance thin layer chromatography (HPTLC; Whatman Inc, Clifton, N.J., USA) using ganglioside standards, GM3, GM2, GD3 and bovine brain ganglioside mixture (Alexis, San Diego, Calif., USA) in a solvent system of chloroform/methanol/0.2% (w/v) $CaCl_2.2H_2O$ (55/45/10, by vol.). Individual gangliosides were recovered and measured as described above.

Cholesterol Assay.

Cholesterol analysis was completed with a test kit (Sigma, Mo., USA).

Analysis of Sphingomyelin (SM) and Platelet Activating Factor (PAF).

Total lipid extracted from microdomains was applied onto a silica gel 'H' TLC plate using chloroform/methanol/2-propanol/0.2% KOH/triethylamine, 45:13.5:37.5:9:27, by vol) and a silica gel 'G' TLC plate (Fisher Scientific, CA) using chloroform/methanol/water, (65:35:6, by vol) for SM and PAF, respectively. Commercial standards of SM, PAF, and lyso-PC (Sigma, Mo., USA) were also spotted on the plate for identification. After development, TLC plates were dried, sprayed with 0.1% ANSA (anilino naphthalene sulfonic acid) and exposed under UV light to detect SM and PAF. Lipids identified were recovered and lipid phosphate was measured (Itoh et al., 1986).

Analysis of Diglyceride (DG).

To measure DG content, extracted lipid was applied onto a silica gel 'G' TLC plate using a solvent system (petroleum ether/diethyl ether/acetic acid, 80:20:1, by vol). After TLC development, 1,2-DG and 1,3-DG were exposed to 0.1% ANSA and identified under UV light with commercial standards. Cholesterol was recovered with 1,3-DG together as 1,3-DG comigrates with cholesterol. 1,2-DG and 1,3-DG were methylated with a known amount of heptadecanoic acid (C17:0) as an internal standard to measure the total fatty acid amount. To remove cholesterol from 1,3-DG after methylation, fatty acid methyl esters (FAME) were applied onto a silica gel 'G' plate and developed with Toluene. Purified FAME was collected, extracted with hexane and injected into the gas liquid chromatograph (GLC, Varian Model 3400 CX, CA) to measure total fatty acid content in DG. The GLC was equipped with a flame ionization detector and a 25 m BP-20 fused capillary column (SGE, Australia).

Statistical Analysis.

Values shown are means±standard deviation (SD). Significant difference between the control group and experimental groups was determined by one-way analysis of variance (ANOVA) with SAS. Significant effects of diet treatment were determined by a Duncan multiple range test at a significance level of $p<0.05$.

Results

Animal Growth and Tissues.

The initial and final body weight of animals after 2 weeks feeding of experimental diets was not significantly different among Control, PUFA and GG groups. Intestinal mucosal weight and intestinal length was not affected by dietary treatment. Food consumption was not influenced by diet (data not shown).

Ganglioside Content and Composition.

Figure 5:
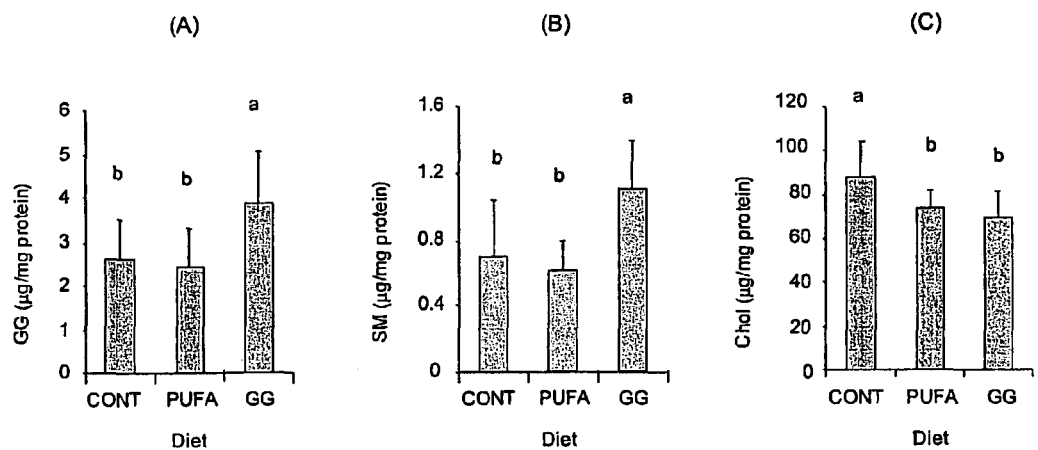
FIG. 5 shows total content of GG (A), SM (B) and cholesterol (C) in intestinal microdomains after feeding different diets for 2 wks.

The effect of dietary ganglioside on total ganglioside content of intestinal microdomains from animals fed either the CONT or experimental diets for 2 weeks is shown (FIG. 5-A). Animals fed the GG diet had higher ganglioside content in intestinal microdomains (up to a 50% increase; P<0.006) when compared to animals fed the CONT diet.

FIG. 5 illustrates the total content of GG (A), SM (B) and cholesterol (C) in intestinal microdomains after feeding different diets for 2 wks. Intestinal microdomains were prepared by a discontinuous sucrose density (5-35-45%) ultracentrifugation from mucosa homogenates suspended by TME solution containing 2% v/v Triton-X 100. GG extracted from the Folch upper phase was purified by Sep-Pak C-18 cartridges and used for color densitometry analysis of total NANA content at 580 nm (Suzuki 1964). SM from the lower phase was identified on TLC plates in chloroform/methanol/2-propanol/ 0.2% KOH/triethylamine solvent system (45:13.5:37.5:9:27, by vol). Phosphate content in SM was measured by a known method (Itoh et al., 1986). Cholesterol content was analyzed by using a test kit. NANA (P<0.006), phosphate (P<0.004) or cholesterol (P<0.02) content in the microdomain was presented as mg/mg protein. Data were presented as Mean±SD with animals in each group.

Figure 6:
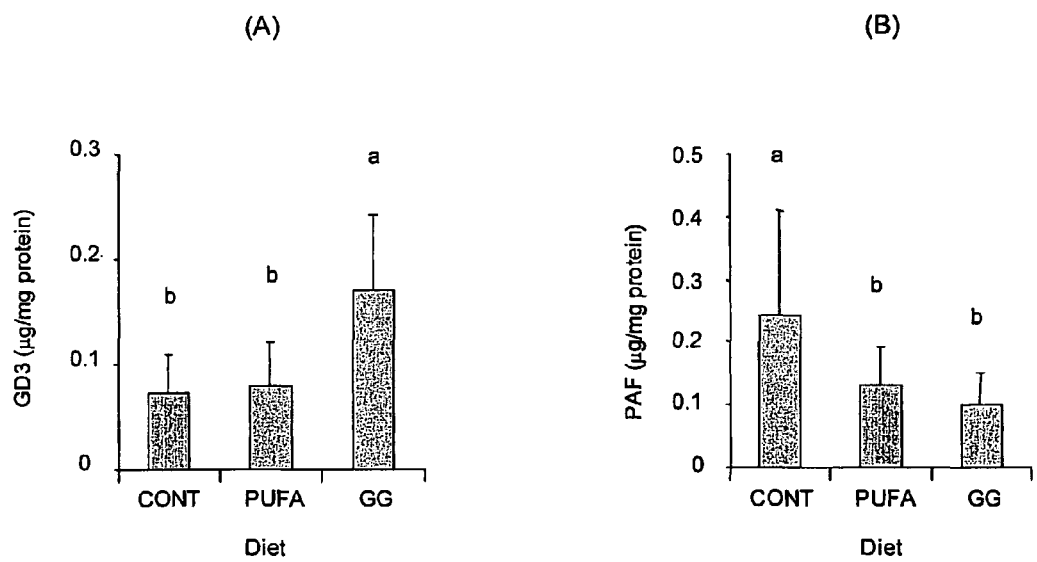
FIG. 6 illustrates total content of GD3 (A) and PAF (B) in intestinal microdomains after feeding different diets for 2 wks.

Animals fed dietary ganglioside significantly decreased GM3 composition in microdomains compared to animals fed the control diet (83.7% to 77.7%, w/w; Table 6) while GD3 increased from 4.4% to 8.3% (w/w; P<0.0008). These compositional changes in GM3 and GD3 were accompanied by a significant change in GD3 content (P<0.002; FIG. 6-A) but not in GM3 content. GM1, GD1a, GD1b and GT1b content was not changed by either diet fed (Table 6). Animals fed the PUFA diet did not exhibit change in either GG content or composition in microdomains from developing animals. The present result confirms that dietary ganglioside significantly increased total GG content resulting in compositional changes such as decreased GM3 and increased GD3 in neonatal intestinal mucosa.

TABLE 6

Composition of Gangliosides in Rat Intestinal Microdomains Fed Either Control or Experimental Diets[1]

| Ganglioside[2] | Diet Treatment | | |
|---|---|---|---|
| | Control | PUFA | GG |
| | | (%)[3] | |
| GM3 | 83.7 ± 2.7[a] | 80.3 ± 4.0[ab] | 77.7 ± 3.3[b] |
| GM1 | 2.7 ± 0.7 | 2.1 ± 1.9 | 2.7 ± 1.4 |
| GD3 | 4.4 ± 1.0[b] | 4.5 ± 1.4[b] | 8.3 ± 2.1[a4] |
| GD1a | 3.5 ± 1.0 | 3.6 ± 1.0 | 3.5 ± 1.2 |
| GD1b | 3.5 ± 1.1 | 5.6 ± 2.1 | 4.2 ± 1.9 |
| GT1b | 2.2 ± 1.9 | 3.9 ± 2.1 | 3.5 ± 0.5 |

[1]Values are means ± SD of 8 rats. Within a row, values with different superscript letters are significantly different at P < 0.02.
[2]Nomenclature was referred from Svennerholm (Svennerholm 1964)
[3]Expressed as a % of total NANA in ganglioside fraction.
[4]Values are significantly different at P < 0.0008.

FIG. 6 shows total content of GD3 (A) and PAF (B) in intestinal microdomains after feeding different diets for 2 wks. Intestinal microdomains were prepared by a discontinuous sucrose density (5-35-45%) ultracentrifugation from mucosa homogenates suspended by TME solution containing 2% v/v Triton-X 100. GG extracted from the Folch upper phase was purified by Sep-Pak™ C-18 cartridges. Individual gangliosides were separated by HPTLC in a solvent system of chloroform/methanol/0.2% (w/v) $CaCl_2 \cdot 2H_2O$ (55/45/10, by vol.). GD3 was recovered and measured as described (Suzuki 1964). Total lipid extracted from microdomains was applied onto a silica gel 'G' TLC plate using chloroform/methanol/ water, (65:35:6, by vol) for PAR Lipid identified was recovered and phosphate in PAF was measured (43). The amount of GD3 (P<0.01) and PAF (P<0.05) in the microdomain was presented as mg/mg protein. Data were presented as Mean±SD with n=8 animals in each group.

Sphingomyelin Content.

Results show that animals fed the GG diet markedly increased SM content in microdomains by 57% (P<0.004), compared to animals fed the CONT diet (FIG. 5-B). No change in SM content in the microdomain was observed in animals fed either the PUFA diet or the CONT diet. This result demonstrates that dietary ganglioside directly increases SM content in intestinal microdomains in developing animals.

Cholesterol Content of Microdomains.

Animals fed the GG diet showed significantly lower levels of cholesterol in microdomains, compared to animals fed the CONT diet for 2 wks (FIG. 5-C). Animals fed the PUFA diet exhibited a lower level of cholesterol in the microdomain, but the effect on cholesterol reduction in the microdomain was smaller than that observed after feeding the GG diet. This result suggests that cholesterol reduction induced by dietary ganglioside in intestinal mucosa is probably due to a decrease in cholesterol content in the microdomain in where cholesterol is enriched.

Ratios of Cholesterol to Gangliosides and Cholesterol to Sphingomyelin.

Animals fed the GG diet showed a highly significant reduction in the ratio of cholesterol to GG, from 31.3 to 18.9, in intestinal microdomains when compared to animals fed the CONT diet (FIG. 7-A). Animals fed the PUFA diet did not exhibit a reduced ratio of cholesterol to ganglioside in intestinal microdomains compared to control animals. Animals fed the GG diet also decreased the ratio of cholesterol to SM in intestinal microdomains. The ratio found was 143, 117 and 63 for animals fed the CONT, PUFA, and GG diet, respectively (P<0.007; FIG. 7-B). These observations suggest that dietary ganglioside increased SM content more than GG content in microdomains since the ratio of cholesterol to SM was more dramatically reduced by 56% in microdomains while the ratio of cholesterol to GG was decreased by 40% when compared to control animals.

FIG. 7 shows the ratio of cholesterol/GG (A) and cholesterol/SM (B) in intestinal microdomains after feeding different diets for 2 wks. Intestinal microdomains were prepared by a discontinuous sucrose density (5-35-45%) ultracentrifugation from mucosa homogenates suspended by TME solution containing 2% v/v Triton-X 100. GG extracted from the Folch upper phase was purified by Sep-Pak C-18 cartridges and used for color densitometry analysis of total NANA content at 580 nm (Suzuki 1964). SM from the lower phase was identified on 'H' TLC plates in chloroform/methanol/2-propanol/ 0.2% KOH/triethylamine solvent system (45:13.5:37.5:9:27, by vol). Phosphate content in SM was measured by a known method (Itoh et al., 1986). Cholesterol content was analyzed by using a test kit. The ratio was obtained by dividing cholesterol content by either GG (P<0.05) or SM (P<0.01) content (mg/mg protein) in the microdomain. Data were presented as Mean±SD with n=8 animals in each group.

Caveolin Content in Microdomains.

Animals fed the GG diet or the PUFA diet exhibited significantly lower expression of caveolin protein in intestinal microdomains compared to animals fed the CONT diet (FIG. 8-A). The blot intensity of caveolin in animals fed the GG and the PUFA diet was 55% and 45% lower, respectively, than that observed for animals fed the CONT diet (FIG. 8-B).

FIG. 8 shows caveolin content determined by western blotting (A), and the intensity of blots (B) in intestinal microdomains fed control diet or treatment diets for 2 wks. Intestinal microdomains were prepared by a discontinuous sucrose density (5-35-45%) ultracentrifugation from mucosa homogenates suspended by TME solution containing 2% v/v Triton-X 100. Proteins lysed (approximately 25 mg/lane) in SDS reducing sample buffer loaded onto 15% SDS-PAGE minigels and immunoblotted with anti-caveolin-1 antibody. A: lane 1, caveolin standard (21-24 kDa); lane 2-5, Control diet; lane 6-9; PUFA diet; lane 10-13, GG diet. B: Blot intensity was analysed by an Imaging Densitometer and each data represents the Mean±SD derived from five animals (n=5) fed different diets.

Content of Inflammatory Mediators, Diglyceride (DG) and Platelet Activating Factor (PAF).

DG and PAF content in microdomains was measured to determine if dietary ganglioside has potential anti-inflammatory effects resulting from reduction of pro-inflammatory signals. Animals fed either the GG diet or PUFA diet showed lower levels of 1,2-DG and total DG content, but not in 1,3-DG, in microdomains compared to control animals (Table 7). Animals fed the GG diet significantly decreased 1,2-DG and total DG by 44% and 43% of controls, respectively. Animals fed the PUFA diet exhibited a smaller reduction compared to control animals (33% and 32% for 1,2-DG and total DG, respectively). Animals fed either the GG diet or the PUFA diet showed significantly lower levels of PAF in microdomains when compared to the animals fed the CONT diet (FIG. 6-B). Feeding the GG or the PUFA diet decreased PAF content up to 59% and 47%, respectively. Taken together, these results suggest that dietary ganglioside and PUFA have potential anti-inflammatory effects in developing animals and that dietary ganglioside is more effective in reducing two inflammatory factors than feeding PUFA.

TABLE 7

Content of 1,2-, 1,3-, and Total Diglyceride in Rat Intestinal Microdomains Fed Either Control or Experimental Diets[1]

| | Diet Treatment | | |
|---|---|---|---|
| | Control | PUFA | GG |
| 1,2-diglyceride[2] | 15.4 ± 2.3$^a$ | 10.4 ± 3.3$^b$ | 8.6 ± 4.4$^b$ |
| 1,3-diglyceride | 1.7 ± 0.2 | 1.3 ± 0.6 | 1.2 ± 0.2 |
| Total diglyceride | 17.1 ± 2.2$^a$ | 11.7 ± 3.8$^b$ | 9.8 ± 4.6$^b$ |

[1]Values are means ± SD of 8 rats. Within a row, values with different superscript letters are significantly different at $P < 0.009$.
[2]Content was expressed as ug/mg protein.

Discussion

Diet Induced-Change. Diet induced-change in the microdomain GD3 and GM3 Content is significant because GD3 and GM3 are involved in cellular function. GM3 is co-localized with signalling molecules such as c-Src, Rho, and Fak in microdomains (Iwabuchi et al., 2000; Yamamura et al., 1997). GD3 activates T-cells (Ortaldo et al, 1996) and has an anti-carcinogenic effect in the mouse colon (Schmelz et al., 2000) Thus, these results may suggest that decreased GM3 alters signals related to these molecules and that increased GD3 (FIG. 6-(A)) enhances immune function and gut protection during development. Results showing accumulation of dietary gangliosides in the microdomains are supported by a previous study demonstrating that administration of [$^3$H] GM3 to Neuro 2a cells showed enrichment of [$^3$H]GM3 in microdomains (Prinetti et al., 1999). These observations suggest that exogenous supplementation of gangliosides directly incorporates into the microdomain.

Cholesterol is an important lipid involved in compartmentalizing microdomains with lipids and proteins (Incardona et al., 2000). Recent studies found that viral pathogens and cholera toxin appear to reach the ER by caveolae (Lencer et al., 1995; Majoul et al., 1996). However, cholesterol reduction in cell membranes inhibits the invasion of HIV-1 (Popik et al., 2002), cholera toxin (Wolf et al., 2002), and malarial parasite (Samuel et al., 2001) by disruption of microdomain structure. Cholesterol depletion by drugs down-regulates caveolin gene expression (Hailstones et al., 1998). The present study confirmed that diet-induced cholesterol reduction in the microdomain also decreased caveolin protein expression. The present data therefore suggests a potential anti-infective effect of dietary ganglioside by reducing cholesterol content leading to less caveolin expression.

The present study provides new information indicating dietary ganglioside decreased pro-inflammatory DG and PAF signals in intestinal microdomains in developing animals. DG located in microdomains modulates the structure and function of microdomains through PKC (Liu et al., 1995; Smart et al., 1995). PAF binds to a PAF receptor in cell membranes to initiate inflammatory signalling events (Flickinger et al., 1999). Together, these observations suggest that PAF may colocalize in microdomains as either ether phospholipids or with its receptors and that diet-induced increase in gangliosides or decrease in cholesterol or caveolin in the microdomain may disrupt PAF and DG localization in the microdomain, thereby resulting in inhibition of inflammatory signalling events.

This example shows that a physiological level of dietary ganglioside has anti-inflammatory effects in developing animals. Thus present results also illustrate that gangliosides have a protective role in gut development in infants.

Example 5

Dietary Gangliosides and Long-Chain PUFA Alter GD3 and Phospholipids in Neonatal Rat Retina Dietary long-chain polyunsaturated fatty acids (LCP) such as arachidonic acid (AA) and docosahexaenoic acid (DHA) have been shown to improve visual acuity in infants (Birch et al., 1998; Carlson et al., 1996; Faldella et al., 1996; and Hoffman et al., 2003). It is thought that dietary LCP stimulate neonatal retinal development by altering membrane phospholipids, which in turn affect cell signaling pathways (Giusto et al., 1997; Huster et al., 2000). During early development, the ganglioside composition of the retina also changes significantly whereby GD3 becomes the primary ganglioside in mammalian retina (Daniotti et al., 1994; Daniotti et al., 1990). Since gangliosides play an important role in neuronal cell differentiation and proliferation (Byrne et al., 1983; Fujito et al., 1985; and Ledeen et al., 1998), this change in ganglioside profile may indicate retinal maturation. A ganglioside diet enriched in GD3 increases ganglioside content by 39% in neonatal rat retina, with a relative increase in GD3. Furthermore, dietary AA and DHA significantly increase the relative levels of GD3 in the retina of neonatal rats, providing evidence that dietary LCP affects ganglioside metabolism in the developing retina and suggesting a new mechanism by which these dietary lipids may promote'maturation of photoreceptor cells.

Introduction

An unusual simplified ganglioside composition is observed in adult retinal photoreceptor cells, compared to that in other central nervous system-derived neurons (Dreyfus et al., 1996). Changes in specific ganglioside content occurs within photoreceptor cells during postnatal maturation to reach an end stage characterized by a predominance of GD3 in the outer retina and only trace amounts of less complex gangliosides (Dreyfus et al., 1996). Since GD3 is the most prevalent ganglioside in fully mature mammalian retinas (Daniotti et al., 1990; Dreyfus et al., 1996), it can be used as a biological marker to evaluate the stage of retinal development. Although the majority of gangliosides are localized in the inner retinal membranes, GD3 is primarily found in photoreceptors in the outer retina (Dreyfus et al., 1996; Dreyfus et al., 1997), where it plays an important role increasing membrane permeability and fluidity (Barbour et al., 1992; Seyfried et al., 1985).

In embryonic chicken retina, total gangliosides increase up to three-fold from the 8-day-old embryo to the 15-day-old stage while GD3 content decreases by 50% Daniotti et al., 1994). In rats, GM1 is downregulated and GD1b is upregulated during the period corresponding to formation of the outer segment, a time which correlates with onset of retinal function (Fontaine et al., 1998). The outer segments, photoreceptor cells, synaptic cells and rhodopsin kinase in the rat retina become functionally active between 10 and 30 days after birth (Fontaine et al., 1998; Ho et al., 1986) during which time GD3 becomes the predominant ganglioside (Daniotti et al., 1990; Dreyfus et al., 1996; Dreyfus et al., 1997).

Dietary long-chain polyunsaturated fatty acids (LCP) such as docosahexaenoic acid (DHA) and arachidonic acid (AA) influence the lipid composition of retinal membranes, particularly during developmental stages (Birch et al., 1998; Carlson et al., 1996; Faldella et al., 1996; Anderson et al., 1976; Carrie et al., 2002; and Suh et al., 1994).

Dietary DHA alters the lipid composition of neuronal tissues in retina and brain, affecting the turnover time for rhodopsin in photoreceptor membranes (Carrie et al., 2002; and Suh et al., 1994). Dietary DHA increases DHA levels, and levels of other very long-chain fatty acids in rod outer segment membranes in young rats, whereas it does not change the fatty acid composition of these retinal membranes in mature rats (Nishizawa et al., 2003; Xi et al., 2003). Inclusion of DHA and AA in infant formulas improves visual development and acuity in infants, but little is known about the biological basis for this effect. Gangliosides are associated with neuronal cell differentiation and proliferation processes including migration, neurite outgrowth, axon generation, and synapse formation (Byrne et al., 1983; Fujito 1985; Ledeen et al., 1998; and Mendez-Otero et al., 2003), processes crucial to visual maturation, but the influence of dietary lipids on retinal ganglioside composition during development is poorly understood.

Figure 9:
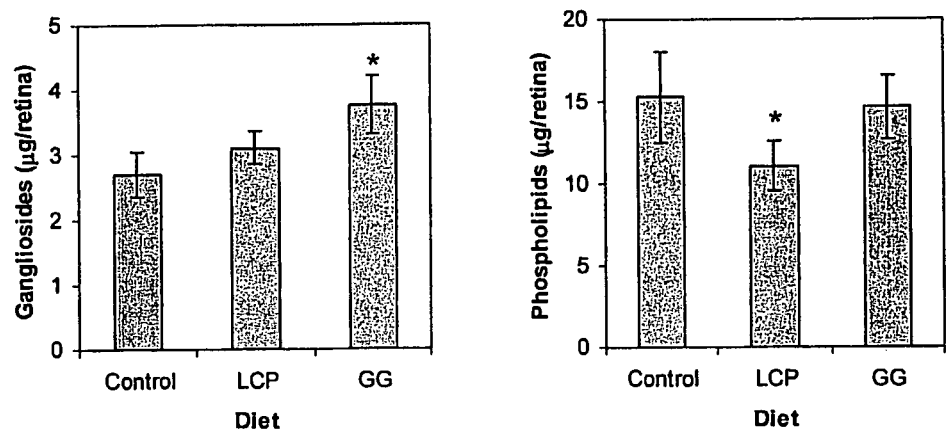
FIG. 9 illustrates the total content of a) gangliosides and b) phospholipids in the retina of control and treatment groups.

In this example, it was hypothesized that dietary gangliosides and LCP could exert biological effects on visual development through modification of retinal gangliosides, which change in composition during maturation. To test this hypothesis, a study was devised that would explore whether an LCP-enriched diet (LCP diet) or a ganglioside-enriched diet (GG diet) could alter retinal ganglioside composition during early development of neonatal rats. The GG diet caused a 39% increase in the total retinal ganglioside content, indicating that gangliosides can be absorbed and incorporated into body tissues (FIG. 9).

More unusual was the finding that the LCP diet as well as the GG diet caused significant increases in the relative proportion of GD3, by 19% and 13%, respectively (Table 8). The specific increase in this particular ganglioside may indicate that dietary ganglioside or LCP stimulate neuronal development in neonates through enhancing the expression of GD3, with possible implications for neonatal development of visual neural pathways and photoreceptor cell function.

Concurrent with changes in ganglioside profile was an alteration in retinal phospholipid composition attributed to both the GG and the LCP diets. Both diets were associated with increases in the relative amounts of phosphatidylinositol and lyso-phosphatidylethanolamine, and a decrease in phosphatidylserine and phosphatidylcholine (Table 9). There was no effect of the GG diet on total phospholipids, whereas the LCP diet was associated with a decrease in total retinal phospholipids (FIG. 9). All other parameters measured, including total retinal cholesterol content, remained unchanged with diet treatment. Phospholipid turnover alters electric surface potential by affecting calcium and cation concentration in retinal rod outer segments (Huster et al., 2000) and is tightly regulated by light and phosphorylation-dephosphorylation reactions (Giusto et al., 1997). Thus, compositional changes in retinal phospholipids in response to dietary ganglioside or LCP may affect light adaptation and activation of protein kinases, which ultimately may lead to enhanced development of retinal function in neonates.

Our study demonstrates that even small physiologic amounts of dietary gangliosides or LCP can have profound effects on the lipid profile of membranes within the developing retina. Further study is needed to assess the mechanism by which these dietary lipids exert the observed effects on retinal lipid composition and to determine whether other neural tissues are similarly affected.

Materials and Methods

Animals and Diets. Two experimental diets or a control diet were fed to male weanling (18-day-old, 40+4.5 g) Sprague-Dawley rats for two weeks. Animals had free access to water and one of three semi-purified diets containing 20% (w/w) fat. The control diet was formulated as 80% basal diet 25 plus 20% fat as a triglyceride blend, reflecting the overall fat composition of infant formula. The LCP-enriched diet (LCP diet) was formulated by including 1% AA and 0.5% DHA by weight as triglyceride in the control diet. The ganglioside-enriched diet (GG diet) was formulated by including in the control diet 0.1% by weight of a ganglioside-enriched powder (70-80% GD3, 9% GD1b, 5% GM3, 6% other gangliosides). The GG diet also contained 0.2% (w/w) phospholipid and 0.07% (w/w) cholesterol. Body weight and food intake were measured every other day throughout the experimental period.

Collection of Retina, Lipid Extraction and Ganglioside Separation.

After decapitation of animals, whole retinas were removed. All samples were weighed and kept in a −70° C. freezer until analysis. Total lipids were extracted using the Folch method (Folch et al., 1957). Gangliosides were extracted into the Folch upper phase solution. The lower organic phase was washed twice with chloroform/methanol/water (3/48/47, v/v/v) and the upper phase extracts combined. Gangliosides were purified by passing the upper phase extract through Sep-Pak™ C18 cartridges (Waters Corporation, Milford, Mass.) preconditioned with 10 mL of methanol, 20 mL of chloroform/methanol (2/1, v/v), and 10 mL of methanol.

Cartridges were then washed with 20 mL of distilled water to remove salts and water-soluble contaminants. Gangliosides were eluted with 5 mL of methanol and 20 mL of chloroform/methanol (2/1, v/v), dried under $N_2$ gas and then redissolved with 500 mL of chloroform/methanol (2/1, v/v). Gangliosides were stored at −70° C. until analysis.

Analysis of Ganglioside Content. Measurement of total gangliosides as N-acetyl neuraminic acid (NANA) was performed as described by Suzuki (1964). An aliquot of the purified ganglioside sample was dried under $N_2$ gas and dissolved with 0.5 mL each of distilled $H_2O$ and resorcinol-HCl (Svennerholm, 1957). The purple-blue color developed by heating was extracted into butyl acetate/butanol (85/15, v/v). Optical density was read at 580 nm. Commercial NANA (Sigma, Mo.) was used as a standard.

Individual gangliosides were separated by silica gel high performance thin layer chromatography (HPTLC; Whatman Inc, Clifton, N.J.) in a solvent system of chloroform/methanol/0.2% (w/v) $CaCl_2.2H_2O$ (55/45/10, v/v/v) and identified using ganglioside standards GM3, GM2, GD3 and bovine brain ganglioside mixture (Alexis, San Diego, Calif.). Individual gangliosides were recovered and measured as described above.

Analysis of Phospholipid Content.

Phospholipids were separated from total retinal lipids by thin layer chromatography (TLC) on silica gel 'G' (Fisher Scientific, CA) using chloroform/methanol/water, (65:35:6, by vol.). Individual phospholipids were resolved on silica gel 'H' TLC plates using chloroform/methanol/2-propanol/0.2% KOH/triethylamine (45:13.5:37.5:9:27, by vol). and identified by comparison to authentic phospholipid standards (Sigma, Mo.). Plates were visualized by 0.1% anilinonaphthalene sulfonic acid under UV exposure. Lipid fractions were recovered and lipid phosphate was measured according to the method of Itoh et al., (1986).

Statistical analysis.

Six retinas from three animals were pooled to constitute one replicate to analyze retinal lipids because of the small amount of lipids in the retina. Values presented are mean±standard deviation (SD) from 6 replicates (n=6) except for individual phospholipid analysis (n=5). Significant differences between the control group and experimental groups were determined by one-way analysis of variance (ANOVA) with SAS (SAS Institute Inc, V6, Fourth Edition, Cary, N.C.). Significant effects of diet treatment were determined by a Duncan multiple range test at a significant level of P<0.05.

Results

Animal Growth and Tissues.

The initial and final body weight of animals, food consumption or retina weight after 2 weeks feeding of experimental diets was not different among groups.

Ganglioside Content, Composition and Ratio of GT1b to GD3 in Retina.

Animals fed the GG diet increased total ganglioside content in the retina by 39% (P<0.001) when compared to animals fed the CONT diet, indicating bioavailability of dietary ganglioside. Feeding animals either the LCP or the GG diet showed an increase in the relative percentage of GD3 in the retina in comparison with feeding animals the CONT diet (by 19% and 13%, respectively). The composition of GM3, GM1, GD1a, GD1b and GT was not changed by either diet fed. The ratio of GT1b to GD3 in the retina was reduced in the both LCP and GG fed animals compared to animals fed the CONT diet.

FIG. 9 illustrates the total content of a) gangliosides and b) phospholipids in the retina of control and treatment groups.

Values are the mean±SD of 6 samples. Asterisks represent significant difference at levels of p<0.0008 and p<0.001, respectively.

TABLE 8

Percent composition of gangliosides in the retina of animals fed different diets[1]

| Ganglioside[2] | Control | LCP | GG | Significant effect of diet (p < x) |
|---|---|---|---|---|
| GM3 | 7.6 ± 2.8 | 5.8 ± 3.2 | 7.7 ± 2.3 | |
| GM1 | 7.3 ± 1.8 | 6.8 ± 2.0 | 7.7 ± 2.2 | |
| GD3 | 25.0 ± 1.8[b] | 29.8 ± 1.7[a] | 28.2 ± 3.5[a] | 0.01 |
| GD1a | 14.3 ± 3.3 | 15.4 ± 3.5 | 16.1 ± 1.8 | |
| GD1b | 19.1 ± 2.2 | 19.0 ± 2.4 | 16.7 ± 1.0 | |
| GT1b[3] | 26.9 ± 2.9 | 23.2 ± 3.1 | 23.6 ± 1.3 | |

[1]Values are mean ± SD where n = 6 for each group. Percentage of gangliosides was measured as % of total NANA content (μg/retina) in the ganglioside fraction.
[2]Nomenclature of gangliosides is described by Svennerholm.
[3]GT1b fraction included GQ1b fraction because of close proximity during TLC separation.

Phospholipid Composition.

Feeding animals the LCP diet, but not the GG diet, reduced total phospholipid content in the retina compared to animals fed the CONT diet. Animals fed either the LCP diet or the GG diet showed lower levels of phosphatidylinositol and lysophosphatidylethanolamine (PE) and higher levels of phosphatidylserine and phosphatidylcholine (PC) compared to animals fed the CONT diet. PE and sphingomyelin (SM) were not changed by either diet treatment fed. Ratios of PE to PC, major phospholipids in the retina, and PC to SM were not affected by both the LCP and GG diet treatment.

TABLE 9

Percent composition of phospholipids in the retina of animals fed different diets[1]

| Phospholipid[2] | Control | LCP | GG | Significant effect of diet (p < x) |
|---|---|---|---|---|
| PE | 35.2 ± 4.7 | 33.4 ± 1.5 | 34.4 ± 2.3 | |
| PI | 7.4 ± 1.6[a] | 5.1 ± 1.3[b] | 4.6 ± 0.7[b] | 0.01 |
| PS | 2.3 ± 0.4[b] | 2.8 ± 0.4[a] | 3.1 ± 0.1[a] | 0.01 |
| LPE | 8.3 ± 0.6[a] | 6.6 ± 0.4[b] | 6.4 ± 1.0[b] | 0.001 |
| PC | 40.4 ± 3.3[b] | 45.5 ± 2.8[a] | 45.6 ± 2.7[a] | 0.04 |
| SM | 6.5 ± 1.3 | 6.6 ± 2.2 | 6.0 ± 0.7 | |

[1]Values are the mean ± SD for n = 5 in each group. Percentage of phospholipids was measured as phosphate content (μg/retina) in the phospholipid fraction.
[2]PE = phosphatidylethanolamine, PI = phosphatidylinositol, PS = phosphatidylserine, LPE = lysophosphatidylethanolamine, PC = phosphatidylcholine, SM = sphingomyelin Cholesterol Content. Cholesterol content in animals fed either the LCP or GG diet was not different from that of animals fed the CONT diet. Animals fed dietary gangliosides exhibited a highly significant reduction in the ratio of cholesterol to gangliosides and phospholipid to gangliosides compared to retinas of animals fed the CONT diet, (28%, P<0.005 and 30%, P<0.0003, respectively). Feeding animals the LCP diet reduced the ratio of cholesterol to gangliosides and phospholipids to gangliosides, but not the ratio of cholesterol to SM, compared to animals fed the CONT diet. The ratio of cholesterol to phospholipids in animals fed the LCP increased compared to animals fed the CONT diet. No change was observed in the ratio of cholesterol to phospholipid and cholesterol to SM in animals fed the GG diet compared to controls.

Discussion

Dietary GG or LCP modifies the lipid classes and the composition of gangliosides and phospholipids in the developing retina. For example, animals fed the LCP diet increased the relative percentage of GD3, but not total ganglioside content, compared to animals fed the CONT diet. The increase in the relative percentage of GD3 was accompanied with significant changes in total and individual phospholipids. The effect of dietary LCP on the compositional change of GD3 may suggest that dietary LCP influence activity of GD3 synthase, an enzyme in the outer retina required to synthesize GD3 from GM3 (Daniotti et al., 1992). Trafficking of DHA-containing PL from the trans-Golgi network to the retina outer segment is accompanied with rhodopsin (Rodriguez et al., 1997). Sphingolipids including GG are enriched in microdomains called lipid rafts or caveolae, which are important domains for lipid trafficking. Thus, the present study suggests that diet-induced increase in GD3 induced by the LCP diet may influence the trafficking of DHA and rhodopsin from the trans-Golgi network to the outer segment of the retina. This result also imply that beneficial effects known that dietary LCP influence visual acuity by altering the LCP composition in the retinal membrane may be a synergistic effect of the compositional change of gangliosides in the retina.

In the retina of the rat, the outer segments, photoreceptor cells, synaptic cells and rhodopsin kinase become functionally active between 10 days and 1 month after birth (Fontaine et al., 1998; Ho et al., 1986) while GD3 becomes the predominant ganglioside (Daniotti et al., 1990; Dreyfus et al., 1997; and Dreyfus et al., 1996). GD3 in the outer retina is involved in increasing membrane permeability and fluidity and is enriched in differentiated retinas. Since animals used in the present study were fed for 2 wks from 17 days of age, this study suggests that dietary LCP and GG may stimulate retinal maturation and development by increasing GD3 content.

Change in the ratio of cholesterol to gangliosides may induce signal transduction for retinal development as known functional involvement of lipid microdomains. The finding that animals fed the LCP or the GG diet showed significant changes in the ratio of cholesterol to gangliosides suggests structural and functional changes of microdomains in retinal membranes. For instance, administration of gangliosides into the plasma membrane of MDCK cells displaces GPI-anchored signaling proteins from microdomains (Simons et al., 1999). Exogenous addition of [$^3$H]GM3 to mouse neuroblastoma Neuro2a cells shows enrichment of [$^3$H]GM3 in microdomains resulting in induction of neuritogenesis by c-SRC activation (Prinetti et al., 1999).

In summary, this study demonstrates that dietary LCP and gangliosides modify metabolism of phospholipids and gangliosides in developing retinal membranes. The present study indicates that a small physiologic amount of phospholipids or gangliosides has a profound effects on the lipid profile of membranes in the retina. The bioavailability of gangliosides in the diet is high rapidly altering the GD3 composition in structural components of the photoreceptor membrane. Dietary gangliosides would thus alter ganglioside content in other neuronal cell types.

Example 6

Diet Induces Change in Membrane Gangliosides in the Intestinal Mucosa, Plasma and Brain In this example the role of gangliosides in plasma membranes of mammalian cells as biologically important molecules is examined. Gangliosides are involved in cell differentiation, proliferation, neuritogenesis, growth, inhibition, signaling and apoptosis (Byrne et al., 1983; De Maria et al., 1997; Ledeen, 1989; and et al., 1996). GM32 and GM1 can act as receptors for enterotoxins such as rotavirus in animals (Rolsma et al., 1998) and *Vibrio cholerae* and *Escherichia coli* in humans (Laegreid et al., 1987). GD3 stimulates T-cell activation in human peripheral blood lymphocytes (Ortaldo et al., 1996; Welte et al., 1987). Ganglioside content and composition is significantly different between stages of development. For example, in human brain, GM1 increases from birth to the age of 1 year while GD1a decreases in the white matter (Vanier et al., 1971). The ratio of GM3/GD3 is about 0.2-0.3 in human colostrum while the ratio is greater than 3 in mature milk since GM3 gradually becomes a major ganglioside upon lactation (Takamizawa et al., 1986). Recent studies have also shown neuroprotective effects of GM1. GM1 treatment of neonatal rats prevents hypoxic damage (Krajnc et al., 1994). GM1 intervitreally injected is protective against rat retinal ischemia induced by pressure (Mohand-Said et al., 1997), and intravenous administration of GM1 reduces infarct volume caused by focal cerebral ischemia (Lazzaro et al., 1994). Despite evidence that gangliosides are involved in development, it is still not clear if dietary gangliosides induce changes in membrane gangliosides or where GM3 and GD3 are localized in the enterocyte membrane. This information is vital to understanding the biological functions of these molecules during the period of development in which their role is the most significant.

The cholesterol content of membrane is also important in maintaining an optimal cell membrane environment. Recent work shows that cholesterol homeostasis is related to sphingomyelin content (Slotte 1999), and cholesterol absorption is regulated in part by sphingomyelin content in intestinal cell membranes (Chen et al., 1992). Cholesterol is enriched in membrane microdomains such as rafts and caveolae, perhaps mediating signal transduction (Maekawa et al., 1999). Gangliosides have the same ceramide as the anchored hydrophobic moiety of sphingomyelin, with the only difference occurring in a polar head group. No studies have reported the effect of gangliosides on cholesterol turnover or membrane content of cholesterol in vivo.

The present research was designed to determine whether dietary ganglioside increases the content of total and individual gangliosides and affects the level of cholesterol, thereby changing the ratio of cholesterol to gangliosides in the intestinal mucosa, plasma and brain in developing rats. This is also the first study showing the localization of GM3 and GD3 in the enterocyte membrane.

Materials and Methods

Animals and Diets.

Male 18-day-old Sprague Dawley rats (n=24), average body weight 40±4.5 g, were randomly separated into 3 groups of 8 with 2 or 3 rats housed in each polypropylene cage. Animals were maintained at a constant temperature of 23° C. and a 12 h light/dark cycle. Animals had free access to water and one of three semi-purified diets containing 20% (w/w) fat for 2 weeks. The composition of the basal diets fed has been reported (Clandinin et al., 1980). Animal body weight and food intake were recorded every other day throughout the experiment. The control diet fat was a blend of triglyceride, which reflected the fat composition of an existing infant formula. Dietary fatty acids were composed of about 31% saturated fatty acids, 48% monounsaturated fatty acids and 21% polyunsaturated fatty acids with a ratio of 18:2n-6 to 18:3n-3 of 7.1. Two experimental diets were formulated by adding either sphingomyelin (SM, 1% w/w, Sigma, Mo., USA) or a ganglioside-enriched lipid (GG, 0.1% w/w, New Zealand Dairy, New Zealand) to the control diet. Ganglioside-enriched lipid consisted of about 45-50% (w/w) phospholipids and 15-20% (w/w) gangliosides. The cholesterol content was <0.35% w/w total lipid. The ganglioside fraction contained about 80% w/w GD3, with GD1b, GM3 and other gangliosides accounting for 9, 5 and 6% w/w, respectively.

Collection of Samples.

After anesthetizing animals with halothane, blood was collected by cardiac puncture and immediately spun at 1000×g (JA-20 Rotor, Beckman, USA) for 30 min to recover plasma. Following decapitation, the brain and small intestine (jejunum to ileum) were excised. The intestine was washed with ice-cold 0.9% saline solution to remove visible mucus and dietary debris, opened and moisture was carefully removed with a paper towel to correctly measure mucosa weight. Intestinal mucosa was scraped off with a glass slide on an ice-cold glass plate. All mucosa samples were weighed and kept in a −70° C. freezer until extraction.

Immunofluorescence Study.

Intestinal sections were collected from animals. Samples were washed with cold phosphate buffered saline (4° C.), cut into 5 mm pieces and fixed with 4% paraformaldehyde in PBS for 1 h at 4° C. After washing with cold PBS, samples were infiltrated with 15% and 30% sucrose in PBS for 90 min and overnight, respectively, at 4° C. for cryostat protection. The tissue sections were placed on plastic molds and covered with embedding medium by optimal cutting temperature (O.C.T.; Tissue Tek, Sakura Finetek USA) on dry ice. Frozen sections (1 mm thickness) were mounted on polylysine-coated microscope slides and washed in cold PBS for 30 min at room temperature. The sections were blocked with 2% bovine serum albumin in PBS for 1 h at room temperature and then incubated with anti-ganglioside GM3 (Mouse IgM, Seikagaku Co., USA) (diluted 1:25), or anti-ganglioside GD3 monoclonal antibody (Mouse IgM, Seikagaku Co., USA) (diluted 1:25), for 2 h at room temperature. After washing the sections 3 times for 10 min with cold PBS, the sections were incubated with fluorescein isothiocyanate (FITC)-conjugated anti-mouse IgM (Sigma, Mo., USA) (diluted 1:300) for 1 h at room temperature in the dark room and washed with PBS again 3 times for 10 min. After staining, a drop of N-propyl gallate was added onto the section before mounting a cover slip. All samples were sealed with nail polish and examined with a confocal microscope (Zeiss Confocal Laser Microscope 510, Carl Zeiss, Germany) with an Argon laser line (488 nm excitation, barrier filter LP505, Plan-Neofluar 40X, 1.3 oil immersion objective).

Ganglioside Extraction and Purification.

Total lipid was extracted using the Folch method (Folch et al., 1957). For extracting gangliosides, the lower phase was washed twice with Folch upper phase solution (chloroform/methanol/water, 3/48/47 by vol.). The upper phase gangliosides were pooled and then purified by passing through Sep-Pak™ C18 cartridges (Waters Corporation, Milford, Mass., USA) prewashed with 10 mL of methanol, 20 mL of chloroform/methanol (2/1, v/v), and 10 mL of methanol as described by Williams and McCluer (1980). The upper phase extract was loaded onto C18 cartridges. Cartridges were then washed with 20 mL of distilled water to remove salts and water-soluble contaminants. Gangliosides were eluted with 5 mL of methanol and 20 mL of chloroform/methanol (2/1, v/v), dried under $N_2$ gas and then redissolved with 500 mL of chloroform/methanol (2/1, v/v). Gangliosides were stored at −70° C. until analysis.

Analysis of total and individual ganglioside content by measuring NANA

Total NANA-gangliosides were measured as described by Suzuki (1964). An aliquot of the ganglioside sample purified by Sep-Pak C18 cartridges was dried under $N_2$ gas and dissolved with each of 0.5 mL of distilled H2O and resorcinol-HCl (Svennerholm 1957) in screw-capped Teflon-lined tubes. The purple blue color developed by heating was extracted into butylacetate/butanol (85/15, v/v) solvent. Optical density was read by a spectrophotometer (Hewlett Packard, 8452A) at 580 nm. For quantitative analysis, N-acetyl neuraminic acid (Sigma, Mo., USA) was used as a standard.

Individual gangliosides were separated by silica gel high performance thin layer chromatography (HPTLC; Whatman Inc, Clifton, N.J., USA) along with standards of ganglioside GM3, GM2, GD3 and bovine brain ganglioside mixture (Alexis, San Diego, Calif., USA) in a solvent system of chloroform/methanol/0.2% (w/v) $CaCl_2.2H_2O$ (55/45/10, by vol.). Individual ganglioside fractions were scraped off and measured as described above.

Cholesterol Assay.

Cholesterol analysis was completed with a test kit (Sigma, Mo., USA).

Statistical Analysis.

The values shown are means±standard deviation (SD). Significant differences between the control group and experimental groups were determined by one-way analysis of variance (ANOVA) with SAS. Significant effects of diet treatment were determined by a Duncan multiple range test at a significance level of $p<0.05$.

Results

Animal Growth and Tissues.

There were no significant differences among the control, SM and GG groups either in terms of the initial body weight of animals or their final weight after 2 weeks feeding of experimental diets (Table 10). Brain weight, intestinal mucosal weight and intestinal length were not affected by dietary treatment. Food consumption was not influenced by diet.

TABLE 10

Weight of Animals and Tissues Fed Control or Experimental Diets[1]

| | Diet Treatment: | | |
|---|---|---|---|
| | Control | SM | GG |
| Initial Body Wt. (g) | 39.9 ± 4.5 | 40.6 ± 4.4 | 40.3 ± 4.5 |
| Final Body Wt. (g) | 117 ± 13.5 | 118 ± 12.1 | 120 ± 13.1 |
| Intestine Length (cm) | 82.0 ± 5.8 | 79.8 ± 6.2 | 84 ± 6.0 |
| Mucosa Wt. (g) | 2.1 ± 0.3 | 2.2 ± 0.3 | 2.1 ± 0.3 |
| Brain Wt. (g) | 1.8 ± 0.1 | 1.8 ± 0.1 | 1.7 ± 0.1 |

[1]Values are mean ± SD with 8, 8, and 6 for mucosa, plasma and brain, respectively.

The Localization of GM3 and GD3 in the Enterocyte by Confocal Microscopy.

Figure 10:
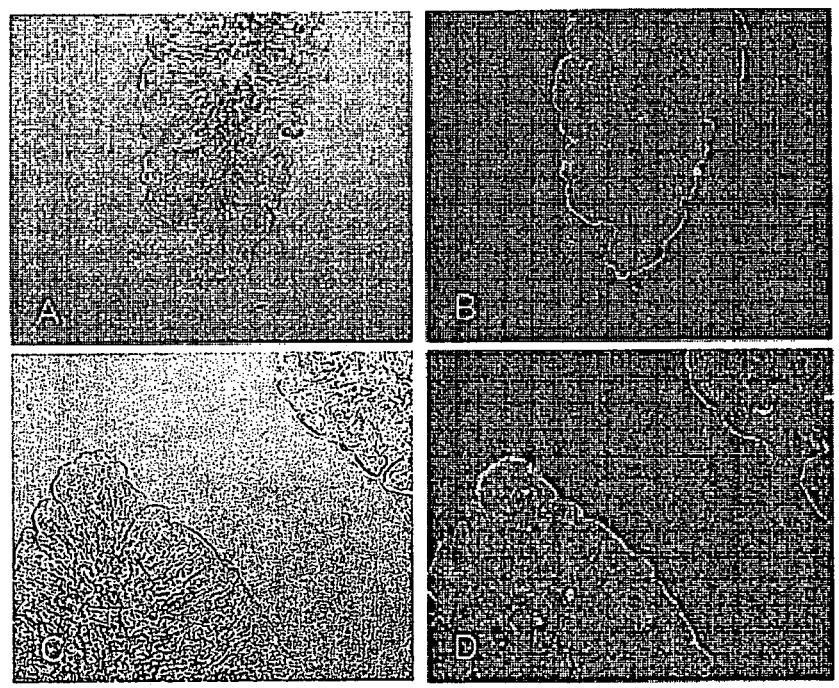
FIG. 10 illustrates immunofluorescent detection of GM3 localization.

Localization of GM3 and GD3 in the enterocyte was determined using a confocal microscope. GM3 stained with FITC-conjugate was almost exclusively localized at the apical membrane of the enterocyte (FIG. 10). The majority of the GD3 was found in the basolateral membrane of the enterocyte with only minor staining in the apical membrane (FIG. 10).

FIG. 10 shows immunofluorescent detection of GM3 localization. Immunofluorescent detection of GM3 in intestinal villi was analyzed with (B, D) or without (A, C) treatment of anti-GM3 visualized with FITC-conjugate IgM and confocal microscopy. GM3 was almost exclusively localized at the apical membrane of enterocytes.

Figure 11:
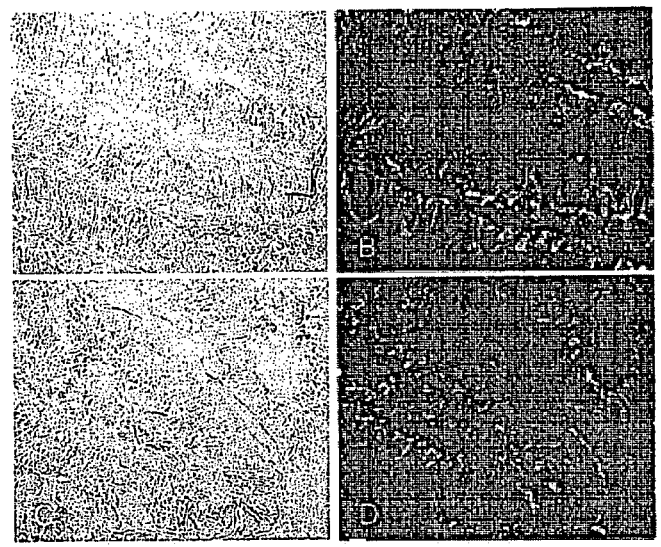
FIG. 11 illustrates immunofluorescent detection of GD3 localization.

FIG. 11 shows Immunofluorescent detection of GD3 localization. Immunofluorescent detection of GD3 in intestinal villi was analyzed with (B, D) or without (A, C) treatment of anti-GD3 visualized with FITC-conjugate IgM and confocal microscopy. GD3 was mostly localized at the basolateral membrane with minor staining at the apical membrane of enterocytes.

Total Ganglioside Content in Tissues and Plasma.

Figure 12:
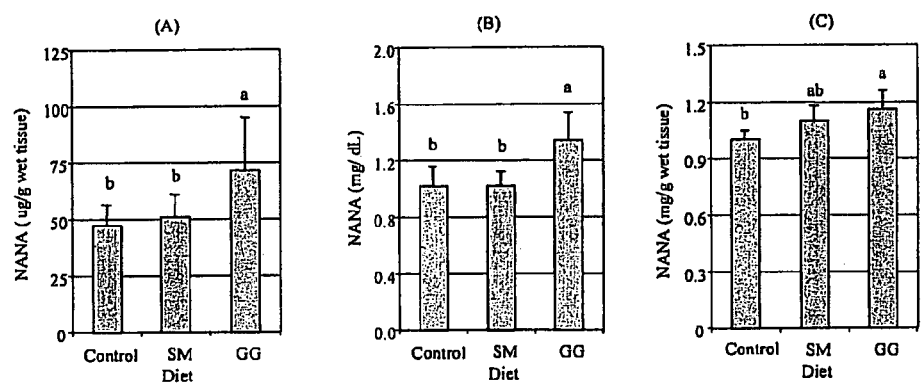
FIG. 12 shows the effect of dietary treatment on total content of gangliosides in (A) the intestinal mucosa, (B) plasma and (C) brain for animals fed either the control or experimental diet for two weeks.

The effect of dietary ganglioside on total ganglioside content of the intestinal mucosa, plasma and brain from animals fed the control and experimental diets for 2 weeks are shown (FIG. 12). Animals fed the GG diet had significantly higher ganglioside content in the intestinal mucosa, plasma and brain compared to control animals. The highest tissue level of ganglioside was observed in the intestinal mucosal membrane. The lowest level of ganglioside was found in brain membrane. No change in total ganglioside content of either tissues or plasma was found after feeding the SM diet.

FIG. 12 illustrates the effect of dietary treatment on total content of gangliosides in (A) the intestinal mucosa, (B) plasma and (C) brain for animals fed either the control or experimental diet for two weeks. Values are means±SD, p<0.02 for A and C, and p<0.003 for B. Treatment values represent the means of n=7, 8 and 6 animals for mucosa, plasma and brain, respectively.

Individual Ganglioside Composition in Tissues and Plasma.

Animals fed the GG diet showed a higher level of GD3 and GQ1b in the intestinal mucosal membrane compared to control animals (Table 11, p<0.001 and p<0.05, respectively). This result was accompanied by significant reduction of ganglioside GM3, which is normally a major ganglioside in the intestinal mucosa. Feeding the GG diet did not affect the level of GM2, GM1, GD1a, GD1b or GT1b in the intestinal mucosa compared to the control. Animals fed the SM diet did not exhibit any change in individual ganglioside patterns, but showed increase in GM2 compared to control animals (p<0.05).

TABLE 11

Composition of Gangliosides in the Rat Intestinal Mucosa Fed Either Control or Experimental Diets[1]

| Ganglioside[2] | Diet Treatment: | | |
|---|---|---|---|
| | Control | SM | GG |
| | | (%)[3] | |
| GM3 | 83.5 ± 6.7$^a$ | 82.4 ± 7.5$^a$ | 76.4 ± 6.9$^b$ |
| GM2 | 2.0 ± 0.9$^b$ | 4.1 ± 2.4$^a$ | 2.8 ± 0.8$^{ab}$ |
| GM1 | 2.7 ± 1.7 | 3.0 ± 1.7 | 1.7 ± 1.2 |
| GD3[4] | 3.2 ± 1.3$^b$ | 2.2 ± 0.9$^b$ | 7.5 ± 1.9$^a$ |
| GD1a | 2.3 ± 1.5 | 2.8 ± 1.5 | 1.9 ± 0.9 |
| GD1b | 1.9 ± 1.0 | 1.5 ± 0.8 | 2.2 ± 1.4 |
| GT1b | 2.1 ± 2.2 | 1.6 ± 1.6 | 3.1 ± 2.2 |
| GQ1b | 2.3 ± 1.6$^b$ | 2.6 ± 1.6$^b$ | 4.5 ± 1.6$^a$ |

[1]Values are mean ± SD of 7 rats. Within a row, values with different superscript letters are significantly different at P < 0.05.
[2]Nomenclature was referred from Svennerholm.
[3]Expressed as a % of total ganglioside fraction.
[4]Values are significantly different at P < 0.001.

In plasma, only four major ganglioside fractions (GM3, GD1a, GD1b and GT1b) were measured since the total ganglioside content was much lower compared to either tissue. The GD3 fraction could not be quantified because unknown fraction partially overlapped with GD3. Two minor gangliosides, GM2 and GM1, were faintly visible on the TLC plate. Animals fed the GG or SM diet did not show a significant change in the individual ganglioside composition of plasma compared to control animals (Table 12). There was a trend toward increased GM3 in animals fed the GG diet compared to control animals (p<0.07). GD1a and GD1b represented 33.9% to 36.0% and 16.1 to 19.6% of the plasma ganglioside fraction, respectively.

TABLE 12

Composition of Gangliosides in Plasma of Rats Fed Either Control or Experimental Diets[1]

| Ganglioside | Diet Treatment: | | |
|---|---|---|---|
| | Control | SM | GG |
| | | (%)[2] | |
| GM3 | 21.6 ± 3.3 | 26.5 ± 3.5 | 28.5 ± 5.3 |
| GD1a | 36.0 ± 5.5 | 30.2 ± 3.6 | 33.9 ± 2.7 |
| GD1b | 16.3 ± 1.8 | 19.6 ± 6.2 | 16.1 ± 3.5 |
| GT1b | 26.1 ± 2.2 | 23.7 ± 4.1 | 21.4 ± 5.5 |

[1]Values are mean ± SD of 5 samples.
[2]Expressed as a % of the total ganglioside fraction.

Brain ganglioside fractions were separated into 14 fractions as shown by Sonnino et al. (1983). The five major gangliosides were GD1a, GT1b, GD1b, GQ1b and GM1. Minor components were GT1a, GD3 and GM3. The remaining six fractions were collected as others. Animals fed the GG diet or SM diet exhibited no change in individual ganglioside composition in the brain compared to control animals (Table 13), but the total ganglioside content increased.

TABLE 13

Composition of Gangliosides in Brain of Rats Fed Either Control or Experimental Diets[1]

| GANGLIOSIDE | DIET TREATMENT | CONTROL | SM |
|---|---|---|---|
| | | (%)[2] | |
| GM3 | 2.5 ± 0.8 | 2.8 ± 1.5 | 2.6 ± 0.5 |
| GM1 | 6.3 ± 0.3 | 6.0 ± 0.3 | 6.2 ± 0.5 |
| GD3 | 3.0 ± 0.7 | 3.0 ± 0.3 | 3.0 ± 0.5 |
| GD1a | 23.2 ± 2.8 | 24.0 ± 2.0 | 23.6 ± 2.5 |
| GT1a | 4.3 ± 0.4 | 4.5 ± 0.3 | 4.8 ± 0.5 |
| GD1b | 11.3 ± 0.8 | 11.0 ± 1.2 | 11.4 ± 0.9 |
| GT1b | 22.4 ± 2.5 | 21.7 ± 1.6 | 21.9 ± 0.9 |
| GQ1b | 6.8 ± 0.3 | 6.5 ± 0.1 | 6.4 ± 0.6 |
| Others[3] | 20.3 ± 4.4 | 20.5 ± 3.8 | 20.0 ± 3.4 |

[1]Values are mean ± SD of 4 rats.
[2]Expressed as a % of the total ganglioside fraction.
[3]Six minor fractions were gathered as others.

Cholesterol Content in Tissues and Plasma.

Figure 13:
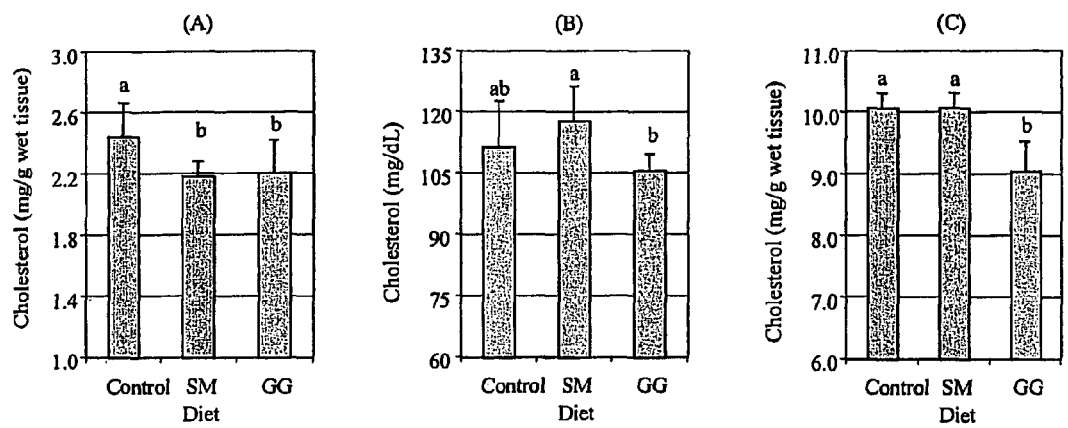
FIG. 13 illustrates the effect of dietary treatment on cholesterol content in (A) the intestinal mucosa, (B) plasma and (C) brain of animals fed either the control or experimental diets for two weeks.

Animals fed the GG diet showed a lower level of cholesterol in the intestinal mucosa and brain, but not in the plasma, compared to animals fed the control diet (FIG. 13). Animals fed the SM diet did not exhibit any change in total cholesterol content in the plasma and brain, but exhibited a significant difference in the intestinal mucosa compared to control animals (p<0.03). Unlike a previous report (Slate 1999), the SM diet did not increase cholesterol content in the intestinal membrane, but reduced cholesterol content compared to animals fed the control diet. Animals fed the GG diet showed lower cholesterol in plasma compared to those fed the SM diet (FIG. 13B).

FIG. 13 illustrates the effect of dietary treatment on cholesterol content in (A) the intestinal mucosa, (B) plasma and (C) brain of animals fed either the control or experimental diets for two weeks. Values are means±SD, p<0.03 for A and B, and p<0.0002 for C. Treatment values represent the means of n=7, 8 and 6 animals for mucosa, plasma and brain, respectively Ratio of Cholesterol to Gangliosides.

Animals fed the GG diet showed a highly significant reduction in the ratio of cholesterol to ganglioside in the intestinal mucosa, plasma and brain compared to animals fed the control diet (FIG. 14), and a lower level of cholesterol in plasma compared to feeding SM, which is an appropriate single lipid control. Animals fed the SM diet also exhibited a reduced ratio of cholesterol to ganglioside in the intestinal mucosa and brain, but not in plasma compared to control animals. Of the three dietary treatments, the lowest ratio of cholesterol to ganglioside was observed in animals fed the GG diet. In contrast, the highest ratio was found in animals fed the control diet in both tissues but not in the plasma. In the plasma, the highest ratio of cholesterol to gangliosides was observed in animals fed the SM diet.

Figure 14:
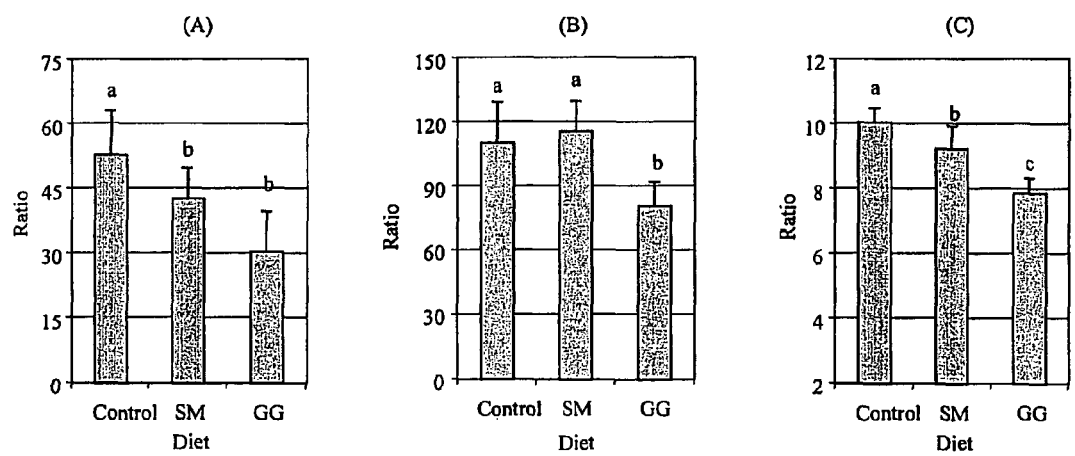
FIG. 14 shows the effects of dietary treatment on the ratio of cholesterol to ganglioside in (A) the intestinal mucosa, (B) plasma and (C) brain of animals fed either the control or experimental diets for two weeks.

FIG. 14 illustrates the effects of dietary treatment on the ratio of cholesterol to ganglioside in (A) the intestinal mucosa, (B) plasma and (C) brain of animals fed either the control or experimental diets for two weeks. Data values are means±SD, A: $p<0.0007$, B: $p<0.002$ and C: $p<0.0001$. Treatment values represent the means of n=7, 8 and 6 animals for mucosa, plasma and brain, respectively. The ratio was obtained by dividing the tissue cholesterol content (mg/g wet weight) by the total tissue content of ganglioside (mg/g wet weight).

Discussion

The notion that gangliosides may have beneficial effects in development has prompted studies of the influence of dietary ganglioside on intestinal and brain development. GM1 acts as a receptor for cholera toxin and *E. coli*. GM3 is the major ganglioside in the enterocyte of humans and animals (Holgersson et al., 1988; Bouhours et al., 1983) but the intracellular localization is not known. The present study clearly shows that gangliosides GM3 and GD3 are localized at the apical and basolateral membrane of the enterocyte, respectively. As GM3 is the major ganglioside in the enterocyte of humans and animals, the present study suggests that the different localizations of GM3 and GD3 probably have different biologic and/or physiologic functions for protection and development. GM1 bound with cholera toxin is transcytosized from the apical to the basolateral membrane to activate the basolateral effecter, adenylate cyclase (Lencer et al., 1995). The present study did not examine the possibility that GM3, like GM1, may also be transcytosized. Total ganglioside content and individual ganglioside composition were significantly changed, but the degree of change could not be quantitatively estimated by confocal microscopy.

Dietary ganglioside significantly increases membrane ganglioside content in the intestinal mucosa, plasma and brain, thereby having potential to cause developmental change. Increased membrane ganglioside in the intestinal mucosa might influence enterocyte immune functions since gangliosides activate immune functions and provide attachment sites for enterotoxins and viruses. Neonatal intestinal mucosa has a relatively low level of immunoglobulin-containing cells after birth to about 2 weeks of age (Perldcio et al., 1980). Mother's milk and the intestine have a compensatory high level of gangliosides during this period (Bouhours et al., 1983; Carlson 1985), suggesting that gangliosides may have a key role in protection of the neonate from antigens.

In the present example, increased membrane ganglioside was accompanied by changes in the individual ganglioside composition of the intestinal mucosa. GD3 was increased by feeding gangliosides while the major ganglioside in the intestine, GM3, decreased compared to control animals. Since GD3 activates T-cells and has an anticarcinogenic effect in the mouse colon (Schmelz et al., 2000), it is logical to suggest that increased GD3 might influence enterocyte functions and infection by altering the interaction with the developing immune system. In plasma, diet treatment considerably increased total gangliosides, but no change was found in the composition of individual gangliosides. In contrast to human serum, where GM3 is the major ganglioside (Senn et al., 1989), GD1a was the major ganglioside in rat plasma. Dietary ganglioside markedly increased total ganglioside content in the brain compared to animals fed the control diet. The present data suggests that dietary ganglioside may affect brain development since an increase of ganglioside content in the brain may effect protection against neuronal injury, induce neurite growth, and is observed in well-fed animals compared to undernourished animals (Karlsson et al., 1978; Morgan et al., 1980). The present study agrees with previous results describing the pattern of major brain gangliosides. In rodents, GM1 increases from the 3rd to 24th month (Aydin et al., 2000) during development (Sun et al., 1972). The low level of GM1 observed in the present study may be due to the younger animal age compared to that of previous work. The lack of significant change in individual ganglioside patterns observed in the brain may be attributed to a short experimental period (2 weeks), the lack of change in ganglioside patterns in the plasma or specific control of individual ganglioside composition in the brain.

The SM content used in this experiment was relatively much higher (>10 fold) than the ganglioside content of the GG diet. This higher level of dietary SM did not alter tissue ganglioside content, suggesting that dietary GG is a better source for enhancing membrane GG and that dietary SM may not be used for GG synthesis during the early stage of development.

The present example indicates that animals fed the GG diet exhibited a significant reduction of cholesterol content in the intestinal mucosa compared to animals fed the control diet. A disruption in microdomain structures caused by reduced cholesterol content may prevent endocytosis of toxins or invasions by bacteria (Parpal et al., 2001; Samuel et al., 2001). A similar result was also observed for animals fed the SM diet. Long term feeding of 1% sphingolipid in the diet significantly reduces plasma cholesterol content (Kobayashi et al., 1997). This study, in agreement with Imaizumi (Imaizumi et al., 1992), showed that feeding SM for two weeks did not alter plasma cholesterol content. This observation may be due to differences in age, diet, species or in vivo and in vitro experimental conditions.

Animals fed the GG diet showed a significant decrease in cholesterol in the brain compared to animals fed the control diet. Cholesterol is maintained in the brain by regulating its de novo synthesis and the uptake of LDL-cholesterol as well as the release of HDL-cholesterol (Bastiaanse et al., 1997). Cholesterol turnover takes place very slowly in brain (Andersson et al., 1990). In comparison with Kobayashi et al., (1997), these data suggest that the effect of gangliosides on cholesterol reduction in the brain may be dependent on NANA combined with glycosphingolipid since sphingolipids, such as cerebroside and SM that do not contain NANA, do not affect brain cholesterol content.

It appears that individual gangliosides have different roles in the regulation of cell behaviour, as each ganglioside is localized in different enterocyte membrane sites. Cholesterol is an important factor involved in cell permeability, fluidity (Rietveld et al., 1998), gap junctions (Malewicz et al., 1990) and membrane microdomains called rafts or caveolae (Brown et al., 1998). Change in membrane cholesterol content in the intestinal mucosa and brain might affect membrane functions during development.

The ratio of cholesterol to gangliosides was decreased in the intestinal mucosa, plasma and brain by feeding the GG diet compared to animals fed the control diet. Changes in this ratio, in both tissues and plasma, could suggest that dietary gangliosides alter membrane functions. This suggestion is supported by early studies showing that changes in membrane lipid composition (Clandinin et al., 1991) and membrane cholesterol content (Rietveld et al., 1998) influence membrane functions. The present research also suggests that dietary gangliosides might affect the traffic of lipids and proteins in membrane microdomains since GM3 and GD3 are localized in different sites and (glyco)sphingolipids including gangliosides and cholesterol are the most abundant lipids present in rafts and caveolae (Incardona et al., 2000; Parton, 1994). The functions of caveolae are closely involved with cholesterol content (Incardona et al., 2000). Depletion of cholesterol content in caveolae inhibited the MAP kinase complex, stimulated Erk enzymes and increased mitogenesis (Furuchi et al., 1998).

Gene expression of caveolin, a marker of protein for caveolae, was upregulated with cholesterol (Fielding et al., 1997), suggesting that cholesterol-protein interaction directly modulates gene expression important for cell development and behaviour. In the sarcolemma, reduction in cholesterol content results in increased $Ca^{2+}/Mg^{2+}$-ATPase activity and decreased $Ca^{2+}/Mg^{2+}$-ATPase activity when the level of cholesterol is high (Ortega et al., 1984). It is also logical to suggest that dietary ganglioside might influence intestinal immune functions by modulating the lipid profile in membrane lipid rafts since activation of signal transduction by IgE receptors and T-cell receptors is dependent on membrane lipid rafts (Moran et al., 1998; Stauffer et al., 1997).

In summary, this study suggests that dietary gangliosides are absorbed by the intestine, remodelled in the enterocyte and induce changes in membrane total content of ganglioside and cholesterol in the intestinal mucosa and brain. The observations suggest that dietary ganglioside fed at a physiological level will alter membrane lipid profiles that influence membrane functions involved in a wide variety of cell functions in neonatal development. Infant formulas have lower levels of gangliosides and a different ganglioside composition compared to that of human breast milk (Pan et al., 2000; Sanchez-Diaz et al., 1997). The bioavailability of dietary gangliosides demonstrated in this paper and the impact on the lipid composition of developing tissues indicates that these differences in feeding regimens are of biological importance.

Example 7

Dietary Ganglioside

Functions in the Intestine During Development

This example illustrates the role of dietary gangliosides in decreasing inflammatory factors PAF and DG in microdomains of the rat intestine. The intestines of rats fed either a control diet (Cont) or a diet high in gangliosides (GG), as described in previous Examples, were assessed for GM3 and GD3 in microdomains. The methodology used for assessing ganglioside composition is as described in previous Examples.

The increase in GD3 composition of microdomains for animals fed the ganglioside-enriched diet correlated to a decrease in both PAF and DG in microdomains. These parameters are indicative of a decrease in inflammatory factors in the intestine and thus show inflammation mediation induced by dietary gangliosides.

Figure 15:
FIG. 15 illustrates the composition of GM3 and GD3 in microdomains of rat intestine.

FIG. 15 illustrates the composition of GM3 and GD3 in microdomains of rat intestine. While GM3 is reduced on the GG diet, GD3 is increased.

Figure 16:
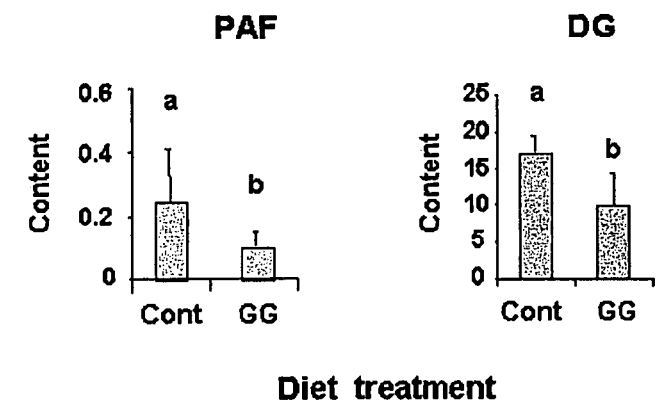
FIG. 16 illustrates the composition of PAF and DG in microdomains of rat intestine. Both PAT and DG are reduced with a GG diet.

FIG. 16 illustrates the composition of PAF and DG in microdomains of rat intestine. Both PAF and DG are reduced with a GG diet. Data shown is presented on a μg/mg protein basis.

Figures 17, 18:
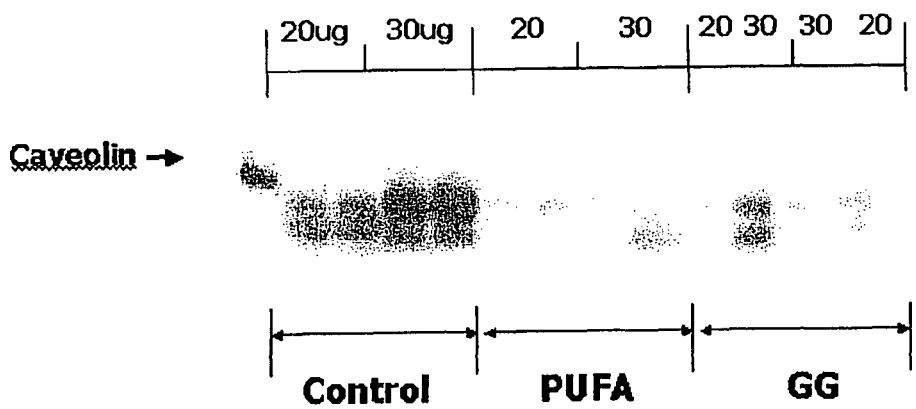
FIG. 17 illustrates the caveolin content of microdomains for animals fed a control, PUFA or GG diet.
FIG. 18 illustrates that feeding a diet high in ganglioside resulted in decreased plasma cholesterol and triglyceride.

FIG. 17 illustrates the caveolin content of microdomains for animals fed a control, PUFA or GG diet. The presence of caveolin is reduced for both the PUFA and GG diets, relative to control. This decrease in caveolin protein, a marker of microdomains, was observed in rat intestines from animals fed a ganglioside-enriched diet. A reduction in caveolin is also indicative of a reduced likelihood of bacterial and/or viral infection through an intestinal entry route.

Example 8

Dietary Gangliosides Effect Plasma Lipid Content and Ratios of Plasma Lipids

This example illustrates the effect of dietary gangliosides on decreasing plasma lipid content, specifically cholesterol and triglyceride, as well as the lipid ratios cholesterol: NANA and cholesterol: phosphorus in the rat.

Plasma was sampled from rats fed either a Control, SM or GG (high in ganglioside) diet, as described in previous Examples. Plasma NANA, phosphorus, cholesterol, and triglyceride, was evaluated as described in previous Examples.

FIG. 18 illustrates that feeding a diet high in ganglioside resulted in decreased plasma cholesterol and triglyceride. This finding suggest reduced cholesterol and lipid absorption from the intestine. Further, because of the decreased cholesterol and increased NANA with the GG diet, a striking reduction in the cholesterol:NANA ratio was observed, illustrating that the GG diet effects lipid composition in plasma.

Example 9

Preparation of a Crude Fraction Enriched in Natural Gangliosides

This example provides a formulation of natural gangliosides which may be used according to an embodiment described herein. The crude fraction described is derived from whole milk, and in particular, fat globules from whole milk.

The initial step in preparing the crude fraction involved in MFGM isolation involves separating the fat globules from fresh, uncooled milk. Centrifugation at low g forces readily separates all but the smallest fat globules from milk, and helps to minimize physical damage to the fat globules (Patton et al., 1975; Mather, 1987). The second step in the process is to wash the fat globules, this will remove entrained or adsorbed components of milk serum as well as caseins and whey (Keenan et al., 1988). Washing involves resuspension and reflotation of lipid globules in buffered or unbuffered water made isotonic with milk serum by addition of sucrose or sodium chloride (Keenan et al., 1988). Two wash cycles at temperatures above 25° C. is sufficient to remove caseins and whey proteins from globules prepared in a laboratory centrifuge, while milk separated via a mechanical cream separator may require 3 or 4 washes (Keenan et al., 1988). The final composition of the material that is recovered as MFGM will vary according to the method and extent of washing of lipid globules (Keenan et al., 1995), and thus intermittent analytical testing carried out to ensure that the product yield and composition conform to specifications.

The final steps in the procedure release the membrane from the globule via slow and successive freeze/thaw cycles.

Finally, the membrane is pelleted via centrifugation at 100 000×g for 60-90 mins (Patton et al., 1975).

Small milk batches of 10 L can be used to test the method during the initial phases of progressing to 100 L, and finally to 1000 L batches.

Example 10

Gangliosides in Prevention and Treatment of Necrotizing Enterocolitis

Necrotizing enterocolitis is an inflammatory bowel disease of neonates and remains the leading gastrointestinal emergency in premature infants. Since current treatments disrupt the natural microflora, are invasive and do not target the specific processes underlying development of necrotizing enterocolitis, it remains the leading cause of morbidity and mortality in neonatal intensive care units. Prematurity, hypoxia-ischemia, infection and formula feeding are established risk factors and breastfeeding is protective.

The role of local vasoactive and inflammatory mediators in the underlying pathogenesis remains elusive due to limitations in current models. Existing models of necrotizing enterocolitis are limited in that they often use animals, immortalized cell lines or diseased tissue to study single risk factors. These models do not contain the aspect of prematurity that is the predisposing factor in infant necrotizing enterocolitis. Moreover, past studies have focused their measurements on plasma or serum vasoactive and inflammatory mediators which reflect the systemic response rather than the local intestinal response. Several vasoactive and inflammatory mediators including endothelin-1, nitric oxide, platelet activating factor, leukotrienes, prostaglandins, cytokines (tumor necrosis factor-α (TNF-α), interleukin-1β (IL-1β), interleukin-6 (IL-6), interleukin-8 (IL-8), interleukin-10 (IL-10), interleukin-12 (IL-12) and interleukin-18 (IL-18)) and reactive oxygen species may play a synergistic and central role in the inflammatory pathway leading to necrotizing enterocolitis. Serotonin promotes bacteria translocation and is elevated during bowel inflammation, bowel obstruction and infection, but the role of serotonin in necrotizing enterocolitis has not been investigated.

Evidence suggesting that breast-fed infants are one tenth less likely to develop necrotizing enterocolitis than formula-fed infants leads to the hypothesis that bioactive factors in human milk might be responsible for protective effects. Gangliosides are sialic acid-containing glycosphingolipids located at the surface of cell membranes and within the milk fat globule membrane.

In this example, a model to study the role of gangliosides in the inflammatory response of human neonatal bowel to infection and hypoxia is employed. These data show that gangliosides reduce neonatal bowel necrosis by reducing production of nitric oxide, LTB4, IL-1b, IL-6 and IL-8 in response to enterotoxic *E. coli* LPS and hypoxia. These findings reveal that gangliosides improve bowel survival in necrotizing enterocolitis by suppressing the local inflammatory response of human neonatal bowel to both infection and hypoxia.

Example 11

Gangliosides Alleviate Symptoms in Inflammatory Bowel Disease Patients

Inflammatory Bowel Disease (IBD) severely impedes quality of life in afflicted individuals. A sensitive and specific biomarker measurable in a readily available specimen is not available, but is desired for diagnosis and prognosis. Some individuals with Inflammatory Bowel Disease do not respond to drug treatment or suffer from drug side effects, and severe cases require surgery to remove bowel. Effective disease management options are limited, and a better understanding of Inflammatory Bowel Disease pathogenesis is desirable. Gangliosides are dietary fats found in milk and are important constituents of intestinal cells. Ganglioside degradation is elevated in the gut of Inflammatory Bowel Disease patients. In the pre-clinical study outlined below, a ganglioside supplement was able to restore ganglioside content and ameliorate gut inflammation. Provision of ganglioside in the diet replaces ganglioside in the gut, consequently restoring proper structure and function to the diseased intestine, and inducing disease remission.

Rate of Inflammatory Bowel Disease is high in the United States; about 1.1 million Americans per year are expected to have Inflammatory Bowel Disease, although the highest reported rate of Inflammatory Bowel Disease is in Canadians.

Ganglioside have impact on catabolism in Inflammatory Bowel Disease, and are associated with increased signaling from pro-inflammatory mediators. Tissue samples from active disease sites in Inflammatory Bowel Disease patients compared to adjacent-to-affected sites, sites in patients with inactive disease, and also sites in healthy control subjects undergoing routine colonoscopy are made. Observations of prevalence and post-operative recurrence of Inflammatory Bowel Disease are considered. The molecular mechanisms by which gangliosides alter gut permeability, inflammatory mediators, and cell surface signalling are considered.

Activity of sphingolipid catabolizing enzymes (sialidase, glycosylhydrolases) is increased preceding active Inflammatory Bowel Disease, enabling a permissive environment for inflammatory signals. Ganglioside treatment improves intestinal integrity (GBP-1), gut permeability (lactulose/mannitol), and quality of life (symptoms, social/emotional function) in Inflammatory Bowel Disease patients. Mucosal ganglioside species GM3 and GD3 mitigate production of proinflammatory mediators (PGE2, LTB4) in intestine and decrease the number of ($\alpha_4\beta_7$+/CCR9+) T-cells that target gut. GM3 and GD3 impair recruitment of inflammatory mediator receptors (IL23R, TNFR, TLR4) to plasma membrane of immune cells and block transcription of products (TNFα, IL6) in NFκB pathway. Ganglioside also decreases proliferation of immune cells isolated from patient with Inflammatory Bowel Disease. Variants in genes related to sphingolipid catabolism (sialidase, glycosylhydrolases) may influence mucosal ganglioside content, predict prevalence, severity, and recurrence of Inflammatory Bowel Disease.

Collectively known as Inflammatory Bowel Disease (IBD), Crohn's disease (CD) and ulcerative colitis (UC) severely impede quality of life in afflicted individuals. Inflammatory Bowel Disease presents with abdominal pain, gastrointestinal bleeding, diarrhea, weight loss, and malnutrition; all of which negatively impact social and emotional welfare. Inflammatory Bowel Disease can be associated with development of joint, liver and kidney diseases, and an elevated risk of lymphoma and colorectal cancer. Severe cases require surgery to remove the affected bowel. The etiologies of Crohn's disease and ulcerative colitis are poorly understood and there is no cure for Inflammatory Bowel Disease. Disease management is difficult, consisting of costly drug treatment. Some individuals with Inflammatory Bowel Disease do not respond to standard drug treatment, while others experience toxic adverse effects. There is a clear need for knowledge of disease mechanisms to enable novel treatment strategies.

Gangliosides are integral to the structure and function of cell membranes. Ganglioside composition of the lipid raft in the brush border of the intestine and apical surface of the colon influence numerous cell processes including microbial attachment, cell division, differentiation, signaling, and mucosal integrity. Ganglioside species allocate to different areas of the enterocyte cell membrane. GM3 predominantly allocates to the brush border membrane and GD3 to the basolateral membrane, indicating that ganglioside species localize to particular regions of the enterocyte to carry out specific functions. Providing ganglioside in the diet increases ganglioside content in intestinal mucosa.

Ganglioside metabolism in the intestinal mucosa of patients with Inflammatory Bowel Disease is fundamental to the etiology of Inflammatory Bowel Disease. Accelerated catabolism of ganglioside in Inflammatory Bowel Disease results may increase pro-inflammatory signaling. Restoring proper structure and function to the diseased intestine may be responsible for induced disease remission in individuals having Inflammatory Bowel Disease. By increasing dietary ganglioside intake, treatment of Inflammatory Bowel Disease is enacted.

Figure 19:
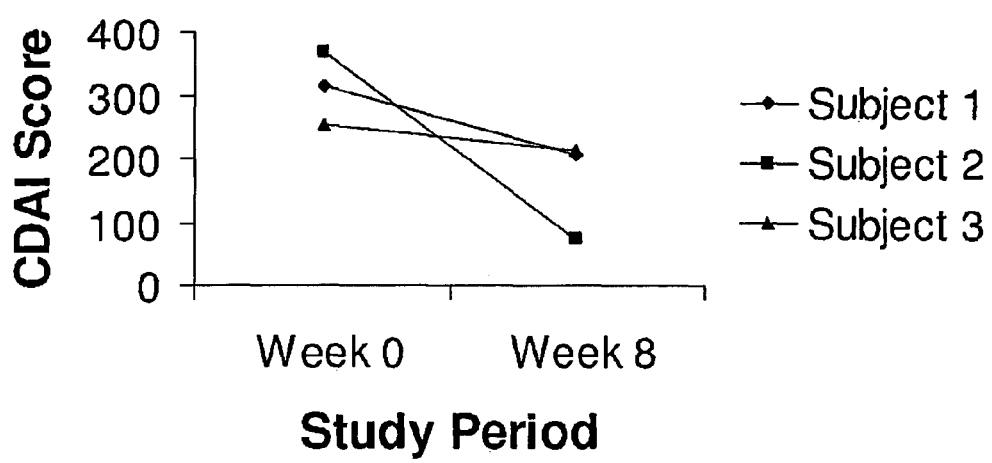
FIG. 19 illustrates the improved Crohn's Disease Activity Index (CDAI) for each of 3 human subjects supplemented with dietary ganglioside.

In this study, three human subjects with a form of Inflammatory Bowel Disease (Crohn's Disease) already receiving standard steroid treatment for Crohn's Disease, were placed on diets to increase consumption of dietary ganglioside, using formulations of ganglioside-enriched milk described herein. FIG. 19 illustrates that the consumption of ganglioside remarkably improved the Crohn's Disease Activity Index (CDAI) for each subject. Consumption over an 8-week period resulted, on average, in subjects having a 43% decrease in CDAI, relative to baseline assessment.

Inflammatory Bowel Disease can thus be relieved, treated, and/or managed to some extent by dietary ganglioside supplementation. Results from this study have implications for dietary treatment strategies for lifetime management of Inflammatory Bowel Disease.

Example 12

Uptake and Fate for Ganglioside GC3 in Human Intestinal CaCo-2 Cells

The Ganglioside GD3 is a glycosphingolipid abundant in colostrum, developing tissues and tumors that regulates cell growth, differentiation, apoptosis and inflammation. Feeding a GD3 enriched diet to rats increases GD3 in intestinal lipid rafts and blood. A model to study GD3 uptake by human intestinal cells was developed to evaluate how enterocyte GD3 uptake is time- and concentration-dependent with uptake efficiency and fate influenced by route of delivery. CaCo-2 cells were exposed to GD3 on the apical or basolateral membrane (BLM) side for 6, 24 and 48 h. GD3 uptake, retention, transfer and metabolism were determined. GD3 uptake across the apical and BLM was time- and concentration-dependent and reached a plateau. GD3 uptake across the BLM was more efficient than apical delivery. Apical GD3 was metabolized with some cell retention and transfer while basolateral GD3 was completely metabolized. This Example demonstrates efficient GD3 uptake by enterocytes and suggests route of delivery influence on ganglioside uptake efficiency and fate. These findings support use of ganglioside-containing enteral or parenteral products to promote intestinal development or to treat or prevent intestinal disorders, such as Inflammatory Bowel Disease.

GD3 uptake into enterocytes is both time- and concentration-dependent and reaches a plateau. The fate of ganglioside taken up by the intestine depends on the route in which it was delivered. Basolateral GD3 is destined for metabolism by the enterocyte while apical GD3 is metabolized with some cellular retention in the membrane and some transfer across the basolateral membrane for distribution to other tissues.

Methods.

Zeta dairy lipid powder was supplied by Fonterra (Cambridge, New Zealand). All cell culture plates and flasks were obtained from Costar (Cambridge, Mass.). Trypsin-EDTA, antibiotic/antimycotic and fetal bovine serum (FBS) were ordered from Gibco (Invitrogen Canada, Burlington, ON). High performance thin layer chromatography plates were purchased from Whatman Inc. (Clifton, N.J., USA). Earle's and Hank's minimum essential media and all other chemicals were purchased from Sigma (St. Louis, Mo.) and were declared to be cell culture grade and high purity.

The human colon cancer cell line, CaCo-2, was obtained from American Type Culture Collection (Manassas, Va.) and was grown (passage 50-65) under standard incubator conditions (humidified atmosphere, 5% $CO_2$, 37° C.) as adherent monolayer cultures in T-flasks containing Earle's minimum essential medium (EMEM). The cell culture growth medium (pH 7.2) was supplemented with 10% (v/v) fetal bovine serum, 1% (v/v) antibiotic/antimycotic, 26 mM sodium bicarbonate, 10 mM HEPES and 1 mM pyruvic acid. Media was changed every 2-3 days and cell density and viability was assessed with a hemocytometer using the trypan blue dye exclusion method.

Total lipids were extracted from a GD3-enriched zeta dairy lipid powder. In short, zeta lipid 2 was dissolved in chloroform/methanol 2:1 (v/v) and homogenized. After vortexing, the tubes were placed on a shaker overnight and $ddH_2O$ was added to give a 5:1 ratio of chloroform/methanol 2:1 (v/v) to ddH20. To extract gangliosides, the ganglioside containing upper aqueous phase was collected and the lower organic phase was washed twice with Folch upper phase solution (chloroform/methanol/water, 3/48/47 by volume). The pooled upper phase ganglioside containing fractions were purified by passage through pre-washed Sep-Pak C18 reverse-phase cartridges (Waters Corporation, Milford, Mass., USA). Once the upper phase extract was loaded onto the column and washed with ddH20, gangliosides were eluted from the column with methanol and chloroform/methanol 2:1 (v/v). The eluate was dried under $N_2$ gas (Prax Air, Mississauga, Ontario) and the ganglioside powder re-dissolved in chloroform/methanol 2:1 (v/v). Gangliosides were stored at −20° C.

Individual gangliosides were separated on silica gel high performance thin layer chromatography plates (HPTLC; Whatman Inc., Clifton, N.J.) with ganglioside standards in a solvent system of chloroform/methanol/ammonium hydroxide/water (60:35:7:3, v/v). To visualize ganglioside bands, HPTLC plates were sprayed with 0.1% (w/v) ANSA (8-anilino-1-napthalene-sulfonic acid) and viewed under ultraviolet light. The GD3 ganglioside bands were scraped off HPTLC plates and pooled together. GD3 was extracted from silica using the same method as ganglioside extraction from zeta lipid powder. Extracted GD3 was purified, eluted, dried and re-dissolved as previously described.

Gangliosides were isolated from CaCo-2 cells by sonication in Tris-mannitol lysis buffer and extraction in chloroform/methanol (2:1, v/v). Extraction and purification was completed as described previously.

Human intestine CaCo-2 cells were seeded at a density of 400,000 cells/ml on a 24 well plate. At confluence, cells were switched into EMEM-4 (4% FBS) and treated with a range of GD3 concentrations (0-64 µg/ml) similar or higher than the amount in human milk on the apical side for 24 h under standard incubator conditions. Cell necrosis was accessed using a lactate dehydrogenase (LDH) release cytotoxicity assay kit (Promega, Madison, Wis.). In brief, cell lysates and supernatants were incubated with an enzyme/substrate solution for 30 min at room temperature and the absorbance of colored formazan product was measured at 490 nm with a microtiter plate reader (Molecular Devices, Sunnyvale, Calif.). Absorbance background reading under kit conditions was less than 0.075. Data were expressed as percentage LDH release from cells. The concentration of GD3 chosen for absorption experiments was based on intestine cell sensitivity to gangliosides.

Polarized, differentiated monolayers of CaCo-2 cells grown on trans-well plates were used as a model to study apical and basolateral GD3 uptake. CaCo-2 cells were seeded at a density of $2.5 \times 10^7$ cells/ml on 0.4 μm pore inserts in 24 well trans-well plates (Corning Inc., Acton, Mass.). The apical (upper) and basolateral (lower) compartments contained 100 μl and 600 μl of EMEM-10, respectively. CaCo-2 cells were grown to confluence and were differentiated twenty days prior to delivering gangliosides. After 20 days, CaCo-2 cells were differentiated and polarized with intact tight junctions, as confirmed by alkaline phosphatase activity and trans-epithelial resistance measurements (data not shown). On day 21, CaCo-2 cells were transferred into Hank's MEM-4, a low serum, low calcium medium containing no antibiotics to limit serum and calcium interference with ganglioside uptake and antibiotic effects on tight junction permeability. Serum present in the media aided in GD3 solubilization and micelle formation during sonication. CaCo-2 cells were incubated under standard conditions in the absence (control, MEM-4 alone) or presence of purified ganglioside GD3 in MEM-4 for 6, 24 and 48 h at a concentration of 5 or 10 μg/ml. The time frame for exposing human intestine CaCo-2 cells to ganglioside GD3 was chosen to be 6-48 h as previous work on ganglioside GM1 uptake by cultured cells predicts slow and incomplete ganglioside absorption from the apical side. The GD3 concentration chosen for absorption experiments is physiological; close to the concentration of gangliosides in mature human milk (9.07 μg lipid bound sialic acid per ml) and high enough to exert biological effects without exhibiting toxicity. The ganglioside treated cells received GD3 on either the BBM (apical) side or the BLM side of CaCo-2 cell monolayers. GD3 delivery on the apical and BLM side of CaCo-2 cells was used as an in vitro model for enteral and intravenous nutrient delivery, respectively. After GD3 incubation, apical and BLM supernatants were collected and cells were washed with PBS and Tris buffer containing EDTA. CaCo-2 cells from each trans-well insert were trypsinized, pooled together in Tris-mannitol buffer and sonicated to form cell lysates. Cell lysates were saved for protein and ganglioside analysis.

The amount of protein in cell lysates was determined using the bicinchoninic acid (BCA) assay. Cell lysates were diluted 1 in 4 with ddH2O. Bovine serum albumin standards and diluted cell lysates (10 μl) were each mixed with 190 μl of a 50:1 mixture of BCA solution and 4% $CuSO_4 \times 5H_2O$ for 30 min at 37° C. The absorbance at 562 nm was measured with a microplate reader (Molecular Devices Co., USA).

Total and individual gangliosides were measured with a colorimetric sialic acid assay as ganglioside bound N-acetyl neuraminic acid (GG-NANA). An aliquot of purified ganglioside sample was dried under $N_2$ gas and dissolved with 0.5 ml of ddH20 and 0.5 ml of resorcinol-HCl in screw-capped Teflon-lined tubes. The purple-blue color developed by reacting resorcinol reagent with ganglioside sialic acid at 160° C. for 8 min was extracted into butylacetate/butanol (85:15, v/v) solvent. Optical density was read by a spectrophotometer at 580 nm. For quantitative analysis, N-acetyl neuraminic acid (also known as sialic acid) was used as a standard.

The following equations were used to calculate the percentage and amount of ganglioside GD3 taken up, retained, transferred and metabolized by human intestinal CaCo-2 cells following brush border membrane or basolateral membrane GD3 delivery. For all calculations the values obtained from the control were subtracted off the test groups to correct for small levels of ganglioside present in the serum and cells. In Equation 1, the % uptake=[(amount delivered−amount remaining)*100%] divided by the amount delivered. In Equation 2, the % retention=[amount cell*100%] divided by the amount uptake. In Equation 3, the % transfer=[amount receiving compartment*100%] is divided by the amount uptake. In Equation 4, the % metabolism=[amount uptake−amount retained−amount transferred*100%] divided by the amount uptake.

Sample size determination for a one tailed comparison at 80% power to detect a 4-5 fold increase in GM1 levels in skin fibroblasts (0.2 nmol/mg protein to 0.9 nmol/mg protein, P<0.05) requires a sample size of 3. All data are expressed as the mean±the standard error of the mean for a sample size of n=4 (4 different cell passages) for intestine cell sensitivity experiments and n=3-4 (3-4 different cell passages) for ganglioside GD3 absorption experiments. Significant differences between the control and experimental group were determined by a one way analysis of variance (ANOVA) and a Tukey test using SAS statistical software version 9.1. Differences between all treatments were considered statistically significant at an alpha of P<0.05.

Results.

To determine the GD3 concentration range that does not exhibit toxicity to the enterocyte for absorption experiments, human intestinal CaCo-2 cells were exposed to a range of ganglioside GD3 concentrations (0-64 μg/ml) for 24 h and cell necrosis was assessed by measuring percentage lactate dehydrogenase (LDH) release from cells. Exposure of CaCo-2 cells to 64 μg/ml GD3 induced significant release of LDH from cells. Although GD3 was not tested at higher concentrations, a crude mixture of gangliosides containing 80% GD3 continues to induce enterocyte toxicity at concentrations as high as 775 μg/ml although the mixture was less potent than pure GD3 at the same concentration. Knowing that the concentration of gangliosides in mature human milk is 9.07 μg of lipid bound sialic acid per ml and in human serum is 10.5 nmol of lipid bound sialic acid per ml, a concentration of 10 μg/ml was chosen as the physiological concentration of GD3 for absorption experiments. A concentration of 10 μg/ml exerts anti-inflammatory effects on infant bowel without exhibiting toxicity.

Human intestinal CaCo-2 cells were exposed to 10 μg/ml ganglioside GD3 on the apical and basolateral membrane side for 6, 24 and 48 h at 37° C., to determine if uptake of exogenous ganglioside GD3 is time-dependent. The time course of GD3 uptake was rapid and linear for the first 6 h, slowed from 6 h to 48 h and reached a plateau. Ganglioside GD3 uptake was faster and more efficient when GD3 was delivered on the basolateral membrane side of CaCo-2 cell monolayers when compared to apical delivery.

Human intestinal CaCo-2 cells were exposed to 5 or 10 μg/ml ganglioside GD3 on the basolateral membrane side for 6 h at 37° C., to determine if uptake of exogenous ganglioside GD3 is concentration-dependent. The amount of ganglioside GD3 taken up from the basolateral membrane side by human intestinal CaCo-2 cell monolayers was twice as high when the concentration of GD3 added was doubled.

Changes in cellular retention, metabolism and transfer of ganglioside GD3 taken up by human intestinal CaCo-2 cells over time was followed to determine the fate of GD3 taken up from the brush border membrane and basolateral membrane side. The amount of GD3 taken up from the BBM side was not significantly higher at 24 or 48 h when compared to 6 h. After 6 h apical exposure to GD3, 96% percent of GD3 taken up was metabolized with small amounts retained in the cell membrane and trace amounts transferred across the basolateral membrane. After 24 h apical exposure to GD3, the percentage GD3 metabolized dropped 32% and significantly larger amounts of GD3 were retained in the cell membrane and transferred across the basolateral membrane. The amount of GD3 taken up from the BLM side was significantly higher at 24 h and 48 h when compared to 6 h. Similar to apical GD3, basolateral membrane GD3 uptake following 6 h exposure was almost completely destined for metabolism with trace amounts retained in the cell membrane or transferred across the apical membrane. In contrast to apical GD3, basolateral membrane GD3 uptake following 24 h exposure was completely metabolized with significant turnover of cell membrane GD3 and transfer of small insignificant amounts of GD3 across the apical membrane. Human intestinal CaCo-2 cells were exposed to 10 µg/ml GD3 for 6, 24 and 48 h on the brush border membrane (BBM) side of cell monolayers. For BBM delivery, 24 µg of GD3 was delivered to the top compartment of 24 pooled trans-wells (1 µg/100 µl/trans-well). Human intestinal CaCo-2 cells were exposed to 10 µg/ml GD3 for 6, 24 and 48 h on the basolateral membrane (BLM) side of cell monolayers. For BLM delivery, 144 µg of GD3 was delivered to the bottom compartment of 24 pooled trans-wells (6 µg/600 µl/trans-well).

Discussion.

Using human intestine CaCo-2 cell monolayers grown on trans-well inserts as a model for enteral and intravenous ganglioside absorption, this Example identifies the physiological concentration range of ganglioside GD3 for the enterocyte and reveals the time frame, efficiency, mechanism and fate of GD3 uptake from the apical and basolateral side of enterocytes.

Human intestine CaCo-2 cell sensitivity experiments with a range of ganglioside GD3 concentrations demonstrated that ganglioside GD3 begins to exhibit toxicity to enterocytes after 24 h exposure at concentrations greater than 32 µg/ml. Knowing that the concentration of gangliosides in mature human milk is 9.07 µg of lipid bound sialic acid per ml, ganglioside GD3 may be safely administered enterally at concentrations several times higher than that present in human milk to access nutrient kinetics and distribution in animals and humans. This study also suggests that a stronger therapeutic effect in the absence of toxicity may potentially be achieved when GD3 is administered at concentrations greater than 9 and less than 32 µg/ml.

This study is the first to examine the time frame and efficiency for apical ganglioside GD3 uptake. The results of this study demonstrate that apical GD3 uptake by human enterocytes begins rapidly within 6 h and reaches a plateau after 24 h. The drop in apical GD3 uptake after 48 h may be explained by disruption of ganglioside concentration gradients by ganglioside shedding as 10 µg/ml GD3 is not toxic to other epithelial cell lines after 48 or 72 h.

Dietary sulfatide, an acidic glycosphingolipid, has been shown to be primarily absorbed in the rat ileum with small amounts incorporated in 2 h, larger amounts incorporated in 6 h and most of the sulfatide disappearing from the intestine by 24 h. When applied for 24-72 h at 37° C., ganglioside GM1 incorporates into fibroblasts in the range of a few nanomoles per mg cellular protein. Compared to GM1 uptake studies using other cell lines, the time frame for GD3 uptake by intestine cells was similar, however, in contrast to GM1, GD3 incorporated in the range of a few micrograms per mg cell protein. Given that the amount of GM1 given to cells was similar or higher (1-150 µg/ml) than the amount of GD3 used in this absorption study (5-10 µg/ml) may suggest that GD3 is more bioavailable than GM1.

Uptake efficiency of ganglioside is influenced by ganglioside structure, formulation, route of delivery, serum, temperature, pH, divalent cations and cell type, morphology and density35. Temperature, pH and cell density were fixed for GD3 absorption experiments while serum and divalent cation levels were kept low. In this absorption study, apical GD3 uptake efficiency of intestine cells reached a maximum of 73% and incorporated 18.5 µg of GD3 after 24 h. In contrast to the intestine, *Giardia* cells exposed to the same amount of ganglioside GM1 under similar experimental conditions reached a maximal uptake efficiency of only 10% and incorporated 2.4 µg of GM1 after 2 h. Ganglioside GM1 is a microbial receptor and modulates ion-sensitive surface proteins while GD3 is implicated in intracellular signal regulation.

Based on ganglioside function, it seems reasonable that most GM1 should remain near the cell membrane surface for membrane protection while most GD3 should be taken up into the intestine cell to alter cell signaling. In translating these findings to clinical use, it is important to consider that in vitro systems provide estimates of uptake and may overestimate since they are isolated systems that do not account for possible ganglioside losses due to gastric acidity, luminal secretions of digestive enzymes and gastrointestinal motility. A small amount of serum was included in the media so lipids and bile salts were present to aid in ganglioside solubilization and micellar formation. An apical ganglioside uptake efficiency of 73% by intestine cells in vitro seems reasonable as dietary cholesterol and sphingomyelin, other amphiphilic lipids, have apical uptake efficiencies of 50% and 22-43%, respectively for rat intestine in vivo. The study shows that apical GD3 uptake by intestine cells is time-dependent, fast and efficient with clinical potential to enterally deliver GD3 to the intestine and perhaps other tissues via the circulation.

This Example suggests that at most 6% of GM1 and 47.4% of GM3 could have been distributed to the intestine. In this study, basolateral GD3 uptake was linear and rapid for the first 6 h then slowed down from 6-48 h. It can be anticipated that GD3 uptake levels off at a later time point as the percentage GD3 uptake approaches 100%. As the GD3 concentration was increased from 5 to 10 µg/ml on the basolateral side, twice as much GD3 was taken up by human intestine cells indicating that GD3 uptake is concentration-dependent.

To access the fate of ganglioside GD3 taken up by human intestine cells, the amount of GD3 retained in the cell, transferred across the membrane and metabolized by intestine cells was calculated. This Example demonstrates that apical GD3 was mostly metabolized after 6 h with small amounts retained by enterocytes or transferred across the basolateral membrane. After 24 h, the additional GD3 taken up by cells was retained or transferred resulting in a significant drop in the percentage of GD3 targeted for metabolism. Thus, apical GD3 that was taken up by intestine cells was prioritized to meet the needs of the enterocyte first. GD3 may be metabolized to release bioactive metabolites or may be incorporated into the plasma membrane as an intact or modified form. Once the needs of the enterocyte were met, any extra GD3 that entered the intestine cell was transferred across the basolateral membrane for transport in the circulation to other tissues. In contrast to apical GD3, basolateral GD3 was completely targeted for metabolism, likely into ceramide, sphingosine or a free fatty acid. Extra GD3 taken up by enterocytes was not retained in the cell but metabolized with trace amounts moving across the apical membrane.

Ganglioside GD3 uptake by human intestine cells is time-dependent, concentration-dependent and efficient when delivered on both the apical and basolateral side of enterocytes. This Example indicates that ganglioside uptake may involve a carrier or concentration gradient with intracellular concentrations of GD3 tightly regulated by the enterocyte. Furthermore, this Example indicates that route of delivery is important to consider when using GD3 for therapeutic purposes as the uptake efficiency and fate differs depending on the route.

Example 13

Gangliosides Protect Bowel by Suppressing Pro-Inflammatory Signals of Infection and Hypoxia A human necrotizing enterocolitis model was used to study the role of local vasoactive and inflammatory mediators in the pathogenesis of the disease and the role of gangliosides in modulating the inflammatory response of infant bowel to infection and hypoxia. In this Example, serotonin and GM-CSF are identified as mediators involved in the pathogenesis of necrotizing enterocolitis (NEC). Gangliosides markedly reduced neonatal bowel necrosis by reducing local nitric oxide, endothelin-1, LTB4, PGE2, $H_2O_2$, IL-1β, IL-6 and IL-8 production in response to enterotoxic *E. coli* LPS and hypoxia. This Example reveals that gangliosides protect the bowel in NEC by suppressing local inflammatory responses of the bowel to both infection and hypoxia.

Methods.

Bowel tissue was obtained from subjects as approved by The Health Ethics Research Board of the Faculty of Medicine and Dentistry, University of Alberta, Edmonton, Canada. The study and written informed consent was obtained from at least one of the parents. Nine infants between 28 and 42 weeks gestational age requiring open bowel surgery for intestinal atresias, and insertion or re-connection of jejuno/ileostomies were recruited from the neonatal intensive care unit at the Stollery Children's Hospital. Up to 1 cm of normally discarded stoma bowel and/or full thickness bowel were resected from close to the re-anastomosis site for tissue culture experiment. Pediatric surgeons minimized the tissue ischemic period to less than 1 min. Inflammatory or infectious bowel, infants with Hirschsprung's disease and neonatal bowel with associated morbid anomalies was excluded from the study.

Details regarding enterocyte culture, and collection, transport, and culture of infant bowel are not provided here in the interests of brevity. Percentage oxygen consumption was assayed using a biological oxygen monitoring system and oxygen probe (Yellow Springs Instrument Co, Ohio, USA) with high sensitivity membranes. Samples were stirred and maintained at 37° C. during measurements. Extraction, Purification and Analysis of Gangliosides. Total lipids were extracted from a ganglioside enriched lipid milk powder (Fonterra, Cambridge, New Zealand) into chloroform/methanol 2:1 (v/v) by vortex, homogenization and shaking overnight. A 5:1 ratio of chloroform/methanol 2:1 (v/v) to dd$H_2O$ was used to extract gangliosides into the upper aqueous phase. The pooled upper phase ganglioside containing fractions were purified by passage through prewashed Sep-Pak C18 reverse-phase cartridges (Waters Corporation, Milford, Mass., USA). Gangliosides were eluted from the column, dried under $N_2$ gas and redissolved in chloroform/methanol 2:1 (v/v). Total ganglioside content was measured as ganglioside bound N-acetyl neuraminic acid (also known as sialic acid) in a colorimetric assay previously described.

Infant bowel tissue was incubated under standard conditions (humidified atmosphere, 37° C., 5% $CO_2$) for 10 h in the presence or absence of 10 μg/ml ganglioside. After 10 h, the supernatant was collected and replaced with bowel culture medium (control), 1 μg/ml enterotoxic *Escherichia coli* lipopolysaccharide (LPS treatment, serotype O111:B4), 0.5 mg/ml oxygen chelating sodium thioglycollate (hypoxia treatment) or LPS and sodium thioglycollate combined for 12 h under standard incubator conditions. After 12 h, supernatant was collected and bowel tissue lysates were prepared by homogenization and stored for subsequent analyses.

Bowel viability and structural integrity was accessed by immunohistochemistry and a lactate dehydrogenase release assay. Nitric oxide production was estimated by analyzing total nitrite (a by product of nitric oxide metabolism) concentration in bowel culture supernatants using a colorimetric assay kit based on the nitrate reductase and Griess reaction (Active Motif, California). Endothelin-1 levels in infant bowel lysates were measured with a commercially available enzyme-linked immunosorbent assay (ELISA) kit (R & D Systems Inc., Minneapolis, Minn.). Cross reactivity with endothelin-2 was reported to be 45%. Endothelin-2 is estimated to be present at less than 20% of the endothelin-1 level and is produced in smaller amounts during stress or disease compared to endothelin-1. Serotonin production was estimated by acylating serotonin in bowel culture supernatants and measuring N-acyl-serotonin concentration using a colorimetric competitive ELISA (Research Diagnostics Inc., New Jersey).

Leukotriene $B_4$ ($LTB_4$) and prostaglandin $E_2$ ($PGE_2$) were measured in bowel lysates with established protocols provided with commercially available enzyme-linked immunosorbent assay kits (R & D Systems, Minneapolis, Minn.). Cross-reactivity with other leukotriene and prostaglandin species was reported to be <0.2% and <17.5%, respectively.

The production of hydrogen peroxide by infant bowel was measured using a Quantichrom Peroxide Assay Kit (Bioassay Systems, California, USA). Cytokine Production. The IL-18 content of bowel lysates was measured with an ELISA kit (Biosource, Camarillo, Calif.). The remaining mixture of proinflammatory, anti-inflammatory and TH1/TH2 cytokines including GM-CSF, IL-1β, TNF-α, IFN-γ, IL-2, IL-4, IL-5, IL-6, IL-8, IL-10 and IL-12 were measured in bowel lysates using the human cytokine 10 panel multiplex kit mixed with the IL-12 single plex kit (Biosource, Camarillo, Calif.). Data was collected using the Luminex 100 IS System and XY Platform (Applied Cytometry). Acquired fluorescence data were analyzed using Star Station software (Version Applied Cytometry). A five parameter weighted regression formula was used to calculate the sample concentrations from the standard curve.

All results were reported as the mean±standard error of the mean for a sample size of n=3 for the CaCo-2 cell experiment and n=9 for the bowel culture experiment. The integrity of cultured bowel tissue was tested for normality by constructing a quantile-quantile plot with S-Plus. The plot for LDH release was approximately linear indicating that a normal distribution is a reasonable assumption for the data. Change in concentration of analyte between treatments was analyzed with SAS using an analysis of variance. A P value of less than 0.05 was considered statistically significant.

Results.

Development of an infant bowel model for necrotizing enterocolitis is verified. A Hematoxylin-eosin staining of a typical section of healthy infant bowel tissue was obtained during open bowel surgery. The presence of intact villi and absence of infiltrated cells suggests infant bowel was viable and non-inflamed before culture. Human intestine CaCo-2 cells were grown in cell culture media with or without oxygen chelating sodium thioglycollate for 6, 12 and 24 h. The percentage change dissolved oxygen levels over time in cell supernatants was observed in reference to baseline levels in cell culture media alone (Time=0 h). Dissolved oxygen levels were significantly lower in cell supernatants with sodium thioglycollate than in cell supernatants without sodium thioglycollate at 6 and 12 h. Data are mean±s.e.m. (n=3). Infant bowel was cultured for 12 h with (hypoxia) or without (normoxia) sodium thioglycollate and hydrogen peroxide was measured in bowel lysates. Sodium thioglycollate significantly induced infant bowel production of hydrogen peroxide. Data are mean±s.e.m. (n=9). Infant bowel was exposed to enterotoxic $E.\ coli$ LPS, hypoxia or the combination in the presence and absence of a 10 h ganglioside pre-exposure. Compared to the control, enterotoxic $E.\ coli$ LPS and hypoxia induced significant bowel necrosis when gangliosides were not present as determined by loss of cell membrane integrity (lactate dehydrogenase release). Ganglioside pre-exposure reduced bowel necrosis following LPS treatment. Values represent mean±s.e.m. (n=9).

The inhibitory effect of gangliosides on infant bowel production of nitric oxide during infection and hypoxia were evaluated. Infant bowel was exposed to enterotoxic $E.\ coli$ LPS, hypoxia or the combination in the presence and absence of a 10 h period of pre-exposure to ganglioside. When gangliosides where not present, LPS, hypoxia and the combined LPS and hypoxia treatment induced significant production of nitric oxide compared to the control as measured by total nitrite, the metabolic by product of nitric oxide. Ganglioside pre-exposure reduced nitric oxide release from infant bowel following enterotoxic $E.\ coli$ LPS infection and the combined LPS and hypoxia treatment. Values represent mean±s.e.m. (n=9).

Inhibitory effect of gangliosides on infant bowel production of proinflammatory eicosanoids and hydrogen peroxide were observed during infection and hypoxia. Infant bowel was exposed to enterotoxic $E.\ coli$ LPS, hypoxia or the combination in the presence and absence of a 10 h period of pre-exposure to ganglioside and LTB4, PGE2 and $H_2O_2$ were measured in bowel lysates. Compared to the control, LPS, hypoxia and the combined LPS and hypoxia treatment without gangliosides triggered significant production of LTB4. Ganglioside pre-exposure reduced LTB4 production by infant bowel following hypoxia and the combined LPS and hypoxia treatment.

Compared to the control, the combined LPS and hypoxia treatment without gangliosides triggered significant production of PGE2 by infant bowel. Ganglioside pre-exposure reduced PGE2 production by infant bowel following combined LPS and hypoxia treatment.

Compared to the control, hypoxia triggered significant production of $H_2O_2$ by infant bowel. Ganglioside pre-exposure reduced infant bowel production of $H_2O_2$ following hypoxia. Values represent the mean±s.e.m. (n=9).

Infant bowel pro-inflammatory cytokines were evaluated for involvement in the pathogenesis of necrotizing enterocolitis and anti-inflammatory effects of gangliosides during infection and hypoxia. Infant bowel was exposed to enterotoxic $E.\ coli$ LPS, hypoxia or the combination in the presence and absence of a 10 h period of preexposure to ganglioside and pro-inflammatory cytokines were measured in bowel lysates.

Observations for granulocyte macrophage-colony stimulating factor (GM-CSF), compared to the control, showed that the combined LPS and hypoxia treatment without gangliosides triggered significant production of GM-CSF by infant bowel.

Tumor necrosis factor-alpha (TNF-α) observations were as follows. The combined LPS and hypoxia treatment without gangliosides induced significant production of TNF-α by infant bowel in comparison to the control. With respect to Interleukin-1beta (IL-1β), when compared to the control, enterotoxic $E.\ coli$ LPS, hypoxia and the combined LPS and hypoxia treatment without gangliosides induced significant production of IL-1β by infant bowel. Ganglioside pre-exposure reduced IL-1β production by infant bowel following the combined LPS and hypoxia treatment. d, Interleukin-6 (IL-6). The combined LPS and hypoxia treatment without gangliosides triggered significant production of IL-6 by infant bowel in comparison to the control. Ganglioside pre-exposure reduced IL-6 production by infant bowel following the combined LPS and hypoxia treatment.

Compared to the control, enterotoxic $E.\ coli$ LPS, hypoxia and the combined LPS and hypoxia treatment without ganglioside induced significant production of IL-8 by infant bowel. Ganglioside pre-exposure reduced IL-8 production by infant bowel following enterotoxic $E.\ coli$ LPS and the combined LPS and hypoxia treatment.

Compared to the control, hypoxia and the combined LPS and hypoxia treatment without gangliosides induced significant production of IL-18 by infant bowel. Values represent the mean±s.e.m. (n=7 or n=9).

The pathogenesis of necrotizing enterocolitis and mechanism by which gangliosides protect infant bowel from inflammation and injury was evaluated. Risk factors associated with the development of necrotizing enterocolitis include pre-maturity, infection, hypoxia-ischemia and formula feeding. There are at least four possible mechanisms by which gangliosides protect infant bowel from injury: 1) gangliosides stabilize membranes and reduce glutamate excitotoxicity during hypoxia; 2) gangliosides bind LPS and prevent LPS interaction with toll like receptor 4 (TLR4); 3) gangliosides inhibit NFκβ activation; and 4) gangliosides inhibit cytosolic phospholipase A2 (cPLA2). None of these mechanisms is in any way considered limiting.

In general, gangliosides improved bowel survival during infection in an infant model of necrotizing enterocolitis. Since primary cultures of enterocytes have limited survival in culture 21, a method was developed to obtain viable, non-inflamed infant bowel during surgery. To overcome limitations of using $E.\ coli$ LPS with immortalized intestinal cell lines and non-physiological hypoxia levels, enterotoxic $E.\ coli$ LPS was used, and an oxygen-chelating compound, sodium thioglycollate, was used to induce bowel necrosis and inflammation in cultured infant bowel as a model for NEC. Oxygen levels were 4.4% lower in media containing sodium thioglycollate after 12 h of human intestine cell culture and gradually returned to normal levels. Similar to other models of ischemia-reperfusion injury, sodium thioglycollate triggered production of reactive oxygen species (FIG. 1d). To test the model, it was examined whether $E.\ coli$ LPS and hypoxia induced necrosis in infant bowel. Using a lactate dehydrogenase (LDH) release assay to measure membrane integrity, it was found that within 12 h of $E.\ coli$ LPS or hypoxia treatment, there was a marked increase in LDH release from infant bowel. Exposure of infant bowel to $E.\ coli$ LPS with hypoxia did not significantly increase LDH release. To investigate whether gangliosides protect infant bowel from *E. coli* LPS and hypoxia-induced necrosis, bowel tissue was pre-exposed to gangliosides for 10 h prior to treatments. The results show that gangliosides significantly attenuate *E. coli* LPS-induced release of LDH.

It was further found that gangliosides inhibit nitric oxide release from infant bowel during infection and hypoxia. *E. coli* LPS or hypoxia alone induced necrosis in infant bowel. Although the combination did not induce necrosis within 12 h, LPS and hypoxia could play an early, secondary role contributing to enterocyte apoptosis and inflammation. Inducible nitric oxide synthase (iNOS) levels are consistently elevated in models of NEC and toxic levels of NO are associated with enterocyte apoptosis and inflammation. Thus, it was evaluated whether *E. coli* LPS and hypoxia would trigger release of toxic concentrations of NO from infant bowel. Total nitrite levels were measured in infant bowel treated with LPS, hypoxia or the combination in the presence and absence of a 10 h period of pre-exposure to ganglioside. The results demonstrate that *E. coli* LPS and hypoxia induce significant release of nitrite by infant bowel and that hypoxia enhances the effect of LPS on nitrite release. When infant bowel was pre-exposed to gangliosides, nitrite release following *E. coli* LPS treatment in the presence and absence of hypoxia was abolished.

Gangliosides were shown to reduce infant bowel production of vasoconstrictors, endothelin-1 and serotonin, during infection and hypoxia. Endothelin-1 is elevated in infant bowel with histopathological features of NEC and induces ischemia, hypoxia and tissue death Although serotonin reuptake inhibitors have been associated with some cases of NEC, the role of serotonin has not previously been investigated in this disease. Thus, these experiments addressed whether *E. coli* LPS or hypoxia trigger production of vasoconstrictors, endothelin-1 and serotonin, in infant bowel and whether gangliosides modulate the process. It was found that *E. coli* LPS significantly induces endothelin-1 production in infant bowel while hypoxia triggers serotonin release. Pre-exposing infant bowel to gangliosides prior to LPS treatment abolished endothelin-1 production. The reduction in serotonin release from infant bowel by gangliosides during hypoxia was not significant.

Gangliosides were found to inhibit eicosanoid and hydrogen peroxide production by infant bowel during infection and hypoxia. Eicosanoids, leukotriene B4 (LTB4) and prostaglandin E2 (PGE2), and reactive oxygen species (ROS) are inflammatory mediators involved in the pathogenesis of NEC. Although it is well established that cyclooxygenase 2 (COX-2) mRNA is elevated in perforated bowel tissue from infants with NEC 25, LTB4 and ROS levels have not been examined in infant bowel. Based on hypoxia-induced NEC models in young animals, intestinal LTB4 and ROS levels are elevated with antioxidant enzyme treatment reducing inflammatory mediator damage to intestine. The effect of *E. coli* LPS and hypoxia on production of eicosanoids and $H_2O_2$ in was assessed in infant bowel and determined whether gangliosides modulate the process. *E. coli* LPS and hypoxia stimulated production of LTB4 and PGE2 in infant bowel while hypoxia induced $H_2O_2$ production. Pre-exposure of infant bowel to gangliosides 10 h prior to infection and hypoxia reduced LTB4 and PGE2 production by 50%. Infant bowel production of $H_2O_2$ during hypoxia was reduced 61% by pre-exposure to gangliosides.

Gangliosides were shown to inhibit pro-inflammatory cytokine production in infant bowel during infection and hypoxia. The role of pro-inflammatory and anti-inflammatory cytokines in NEC remains elusive due to limitations in current models and analyses. Most studies have measured plasma and serum cytokines which reflect the systemic rather than the local intestinal response. Measuring neonatal cell cytokines continues to be challenging as the neonate's immune system gives a low response to common mitogens. Evidence of local bowel cytokine production in NEC is limited to a few studies that measured cytokine mRNA expression in animals and in resected bowel tissue from infants with NEC.

The effect of *E. coli* LPS and hypoxia on production of pro-inflammatory, anti-inflammatory and TH1/TH2 cytokines were evaluated in infant bowel tissue. Granulocyte macrophage-colony stimulating factor (GM-CSF) was found to be produced by infant bowel in response to *E. coli* LPS and hypoxia. Similar to other models of NEC, *E. coli* LPS and hypoxia induce marked production of TNF-$\alpha$, IL-1$\beta$, IL-6, IL-8 and IL-18. Levels of IL-12, IFN-$\gamma$, IL-2, IL-4, IL-5 and IL-10 were too low to detect in control and treated bowel tissue.

To investigate whether gangliosides exhibit anti-inflammatory properties, bowel tissue was pre-exposed to gangliosides for 10 h prior to treatments and pro-inflammatory cytokines were measured. The results show that gangliosides suppress infant bowel production of IL-1$\beta$, IL-6 and IL-8 during *E. coli* LPS infection and hypoxia by 75%, 48% and 48%, respectively.

Discussion.

An infant bowel model of NEC that overcomes limitations of current models was developed to investigate roles of local vasoactive and inflammatory mediators in the pathogenesis of NEC and protective effects of gangliosides. To overcome limited survival time of primary enterocyte cultures, a method to culture viable, non-inflamed infant bowel for 24 h was developed. Unlike immortalized intestinal cell lines that respond poorly to apical *E. coli* LPS 28, infant bowel produced significant amounts of vasoactive and pro-inflammatory mediators and developed necrosis following apical treatment with *E. coli* LPS. Instead of inducing acute intestinal injury under non-physiological, severe hypoxic-ischemic conditions observed in most animal models of NEC, the present model gradually lowers oxygen to more physiological hypoxic levels and then recovers oxygen to normal levels using sodium thioglycollate, an oxygen chelator that establishes anaerobic conditions for bacteria growth. Intestinal inflammation tends to be less severe after complete removal of oxygen as compared with gradual removal. Hydrogen peroxide was generated during hypoxia suggesting that the model represents ischemia-reperfusion injury similar to other models of NEC. The model uses infant tissue and includes the aspect of prematurity that consistently predisposes neonates to this disease along with exposure to compound risk factors such as infection and hypoxia.

In the present model, enterotoxic *E. coli* LPS and hypoxia alone significantly induced lactate dehydrogenase release from infant bowel suggesting loss of membrane integrity and bowel necrosis. The extent of tissue damage was not as profound as expected, particularly during combined infection and hypoxia, indicating that the model might represent an early point in disease progression where transition from apoptosis to necrosis is not complete. The time frame of 24 h in which viable infant bowel can be cultured and treated is limited by microbial growth. However, bowel necrosis was significant enough following LPS treatment to demonstrate that ganglioside pre-exposure reduces bowel necrosis.

To identify the time frame for disease progression, nitric oxide, a vasoactive and inflammatory mediator strongly correlated with enterocyte apoptosis in NEC was measured following infant bowel *E. coli* infection and hypoxia. Similar to other models of NEC, high concentrations of total nitrite were produced by infant bowel following treatment with *E. coli* LPS and hypoxia. Given that NO regulated pro-apoptotic gene BNIP3 and nitrosative stress are associated with enterocyte apoptosis in resected intestine from infants with NEC infection and hypoxia may induce infant bowel apoptosis in this model.

Since apoptosis has been demonstrated to initiate bowel necrosis in models of NEC the model described herein represents progression of NEC from early to late stage. Infection with LPS was a stronger stimulus for NO release than hypoxia. Basal NO production by neonatal intestine during hypoxia is poor. It is also possible that preconditioning occurred and hypoxia inducible factors were released to protect against further hypoxic insult. Nitric oxide production was enhanced when *E. coli* LPS was given under hypoxic conditions. It is well established that LPS triggers NO production by inducible NOS through interaction with toll like receptor 4 (TLR4) and activation of the NFκβ pathway. In addition to the NFκβ pathway, hypoxia triggers NO production by the constitutive, calcium dependent neuronal nitric oxide synthase. Since ganglioside preexposure abolished bowel nitrite production during infection in the presence and absence of hypoxia but not with hypoxia alone, it is likely that gangliosides inhibit NO production primarily by inhibiting the TLR4-NFκβ pathway.

Since the ganglioside mixture used was similar to human milk composition with GM1 present in lower amounts than GD3, it is expected that LPS binding and membrane stabilizing effects of GM1 would be less prominent than NFκβ inhibition by GD3.

In addition to protecting infant bowel from injury, a homeostatic role for gangliosides in maintaining gut blood flow during infection and hypoxia was identified. Nitric oxide and endothelin-1 balance is crucial for maintaining intestinal blood flow and this balance is disturbed in premature infants.

Endothelin-1 is also elevated in intestine afflicted with NEC and is associated with blood vessel constriction In the present model, NO and endothelin-1 levels are elevated during infection and hypoxia and restored to normal levels following pre-exposure to gangliosides. Since LPS induces endothelin-1 expression, it is speculated that gangliosides reduce endothelin-1 levels by binding to LPS and reducing LPS-mediated endothelin-1 synthesis. It is not known whether gangliosides interfere with endothelin-1 synthesis enzymes. The vasoconstrictor, serotonin, was also elevated during hypoxia in the present model, however, the reduction in serotonin following pre-exposure to gangliosides was not significant. It is not known whether gangliosides are taken up by serotonin-producing enterochromaffin cells but it is known that gangliosides alter serotonin receptor sensitivity 16 and interfere with downstream signaling pathways leading to serotonin induced vasoconstriction.

Gangliosides also exhibited both anti-inflammatory and anti-oxidant effects in the present model of NEC. During infection and hypoxia, pro-inflammatory eicosanoids, LTB4 and PGE2, involved in recruiting leukocytes to the inflammatory site were reduced by gangliosides. During hypoxia, gangliosides reduced infant bowel generation of $H_2O_2$, a reactive oxygen mediator that induces oxidative cell membrane damage and enterocyte apoptosis in NEC.

Eicosanoids are produced following NFκβ activation and during hypoxia, production is dependent upon calcium and reactive oxygen species produced following ischemia-reperfusion injury. Calcium and oxygen sensitive enzymes including cytosolic phospholipase A2 (cPLA2), 5-lipoxygenase and cyclooxygenase-2 generate LTB4 and PGE2. Since gangliosides have been demonstrated to inhibit cPLA2 and enhance catalase activity, it is possible that gangliosides exert anti-inflammatory and anti-oxidant effects by inhibiting NFκβ and cPLA2 activation and by increasing catalase activity.

This Example presents insight into the role of local cytokines in the pathogenesis of NEC was gained and anti-inflammatory properties of gangliosides were reinforced in infant bowel. Granulocyte macrophage-colony stimulating factor (GM-CSF), a maturation, proliferation and activation factor of macrophages, was identified to be significantly elevated following *E. coli* infection and hypoxia.

Ganglioside pre-exposure significantly reduced infant bowel production of pro-inflammatory cytokines IL-1β, IL-6 and IL-8. The anti-inflammatory effect is likely attributed to both the ability of the ganglioside to bind LPS and to directly prevent NFκβ activation.

Example 14

Gangliosides Exert a Protective Treatment Effect on CaCo-2 Cells

Figure 20:
FIG. 20 provides a TEM image of Caco-2 cells without ganglioside or DSS (control).
Figure 21:
FIG. 21 provides a TEM image of Caco-2 cells with DSS only.
Figure 22:
FIG. 22 provides a TEM image of Caco-2 cells with DSS and ganglioside.

The effect of gangliosides on Caco-2 cell characteristics, including morphology, is outlined herein using cells isolated according to methods described in previous examples. In this example, a dextran sulphate sodium (DSS) induced model of intestinal cell damage was used, as a model colitis. Ulcerative colitis is a category of inflammatory Bowel Disorder, and thus the model is considered to have relevance to the mechanism of action of Inflammatory Bowel Disorders in humans. FIG. 20 illustrates control Caco-2 cells using transmission electron microscopy (TEM). The cells are incubated in a medium absent ganglioside or dextran sulphate sodium (DSS), and show good morphological structure. FIG. 21 provides a transmission electron micrograph of the Caco-2 cells with DSS present in the medium to induce cellular damage. Damage is apparent when cells are compared with the control cells of FIG. 20. In FIG. 22, a transmission electron micrograph of Caco-2 cells incubated with DSS and ganglioside is shown, and improved morphological structure was observed. These observations illustrate that gangliosides exert a protective treatment effect, and improve barrier function in an IBD cell culture model of Caco-2 cells with DSS induced damage.

Figure 23:
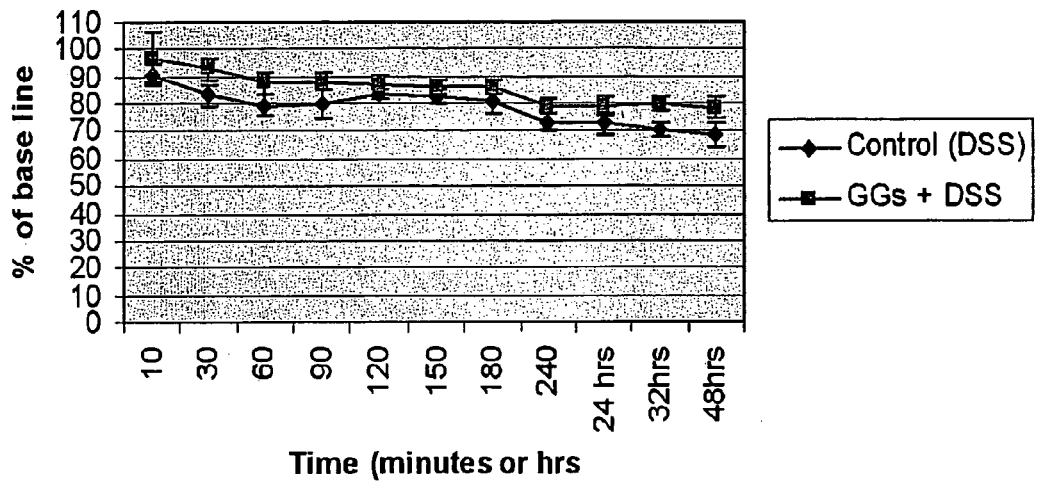
FIG. 23 illustrates the effect of ganglioside on trans epithelial electric resistance of Caco-2 cells.

The Caco-2 cells were also observed for trans epithelial electron resistance (TEER). In an observation illustrated in FIG. 23 (n=6), control cells exposed to DSS were compared with treated cells having exposure to both DSS and gangliosides in the medium. The protective treatment effect of ganglioside on DSS-induced damage in Caco-2 cells is seen by the TEER values being consistently lower over the first 240 minutes, and extending to a 48 hour period. A consistent observation of between about 5% and 10% lower TEER, expressed as a percentage of baseline value (pre-exposure) was observed in the control (DSS only) group versus the treatment of DSS plus ganglioside. This observation emphasizes the protective treatment effect of ganglioside on the DSS model of Inflammatory Bowel Disease, with respect to intestinal cell integrity, and/or intestinal permeability.

Figure 24:
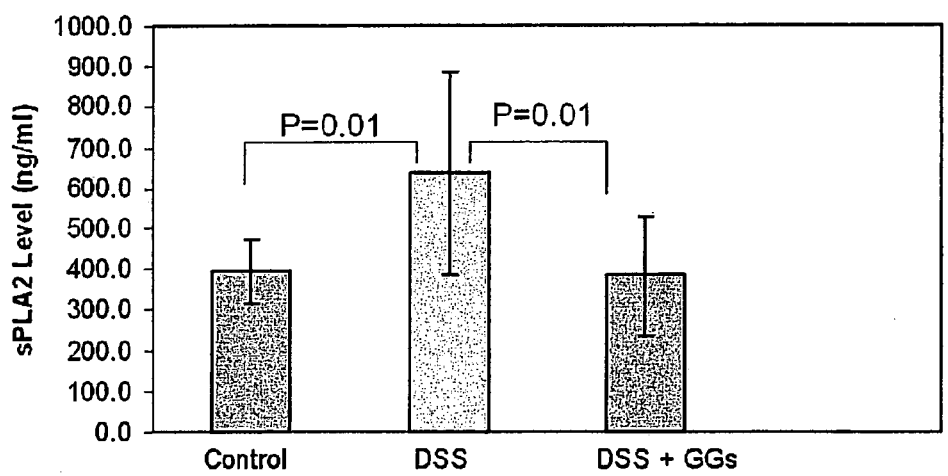
FIG. 24 illustrates the effect of ganglioside supplementation sPLA2 level of Caco-2 cells.

Caco-2 cells were then assessed for sPLA2 (phospholipase A2) level, as shown in FIG. 24 (n=12). The activity of phospholipase A2 is elevated in the intestinal epithelia of patients with Inflammatory Bowel Disease (IBD). Here, the effect of ganglioside supplement on sPLA2 level in Caco-2 basolateral media is evaluated. The control cells having no ganglioside or DSS were compared with a DSS-exposed group of cells and a DSS plus ganglioside incubated Caco-2 cells. The damage induced, as measured by sPLA2 level was evident in an elevated level for the DSS group, but there was no difference detected between the DSS+ganglioside (GG) group versus the control group of Caco-2 cells having no exposure to DSS. Thus, the protective treatment effect of ganglioside on this parameter in this model of Inflammatory Bowel Disease is evidenced.

Figure 25:
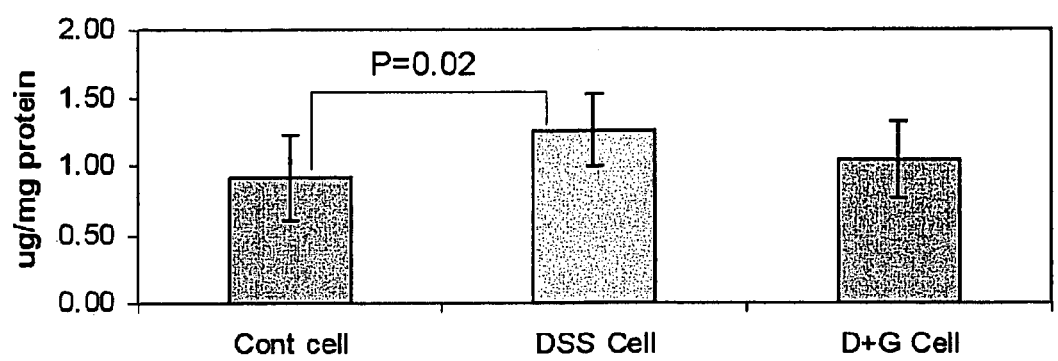
FIG. 25 illustrates the effect of ganglioside supplementation on cellular phospholipid content of Caco-2 cells.

FIG. 25 illustrates the effect of DSS and DSS plus ganglioside (D+G) versus a control Caco-2 cell model on cellular phospholipid content (n=10). Intracellular phosphatidylethanolamine (PE) was evaluated in all three groups, and although a significant increase (P=0.02) in cellular phospholipid content was observed in the DSS group, the difference between the ganglioside-treated group exposed to DSS versus the control group was not a significant difference. Gangliosides decrease the phospholipase A2 concentrations and modulate the phospholipid profile of human Caco-2 cells, and thus exert a protective treatment effect of ganglioside in this cell model of colitis is further affirmed.

The above-described embodiments are intended to be examples only. Alterations, modifications and variations may be effected to the particular embodiments by those of skill in the art without departing from the scope of the invention, which is defined solely by the claims appended hereto. All documents are herein incorporated by reference.

The invention claimed is:

1. A method for treating inflammatory bowel disease in a subject ineed thereof, the method comprising administering a formulation comprising at least one ganglioside to the subject, wherein the at least one ganglioside comprises at least about 80% GD3 by weight of total ganglioside content.

2. A method for treating inflammatory bowel disease in a subject ineed thereof, the method comprising administering a formulation comprising at least one ganglioside to the subject, wherein the formulation comprises at least about 50% GD3 by weight of total ganglioside content and about 10% GD1b by weight of total ganglioside content.

3. A method for treating inflammatory bowel disease in a subject ineed thereof, the method comprising administering a formulation comprising at least one ganglioside to the subject, wherein the formulation comprises at least about 50% GD3 by weight of total ganglioside content and about 5% GM3 by weight of total ganglioside content.

4. The method of claim 1, wherein the formulation is administered to provide from about 1 mg/day to about 10 g/day of ganglioside.

5. The method of claim 1, wherein the formulation is administered to provide from about 5 mg/day to about 500 mg/day of ganglioside.

6. The method of claim 1, wherein lipid components in microdomains are altered by a reduction in platelet activating factor (PAF), a reduction in the ratio of cholesterol to sphingolipid, or a reduction in total diglyceride in the microdomains.

7. The method according to claim 1, wherein the formulation additionally comprises a ganglioside selected from the group consisting of: GM1, GM2, GM3, and GD1b.

8. The method according to claim 7, wherein the formulation comprises about 80% GD3 and about 5% GM3 by weight based on total ganglioside content.

9. The method of claim 1, wherein administering comprises oral consumption.

10. The method of claim 1, wherein the formulation comprises a ganglioside supplemented liquid or food.

11. The method of claim 10 wherein the formulation is a supplemented liquid comprising about 0.01 to about 1000 ppm ganglioside.

12. The method of claim 10 wherein the formulation comprises milk having a fat fraction of from about 1 to about 4% by weight, wherein the fat fraction comprises from about 0.1% to about 2.0% by weight ganglioside.

13. The method of claim 1 wherein inflammatory bowel disease comprises Crohn's disease or ulcerative colitis.

14. The method of claim 2, wherein the formulation is administered to provide from about 1 mg/day to about 10 g/day of ganglioside.

15. The method of claim 2, wherein the formulation is administered to provide from about 5 mg/day to about 500 mg/day of ganglioside.

16. The method of claim 2, wherein lipid components in microdomains are altered by a reduction in platelet activating factor (PAP), a reduction in the ratio of cholesterol to sphingolipid, or a reduction in total diglyceride in the microdomains.

17. The method of claim 2, wherein administering comprises oral consumption.

18. The method of claim 2, wherein the formulation comprises a ganglioside supplemented liquid or food.

19. The method of claim 18, wherein the formulation is a supplemented liquid comprising about 0.01 to about 1000 ppm ganglioside.

20. The method of claim 18 wherein the formulation comprises milk having a fat fraction of from about 1 to about 4% by weight, wherein the fat fraction comprises from about 0.1% to about 2.0% by weight ganglioside.

21. The method of claim 2 wherein inflammatory bowel disease comprises Crohn's disease or ulcerative colitis.

22. The method of claim 3, wherein the formulation is administered to provide from about 1 mg/day to about 10 g/day of ganglioside.

23. The method of claim 3, wherein the formulation is administered to provide from about 5 mg/day to about 500 mg/day of ganglioside.

24. The method of claim 3, wherein lipid components in microdomains are altered by a reduction in platelet activating factor (PAF), a reduction in the ratio of cholesterol to sphingolipid, or a reduction in total diglyceride in the microdomains.

25. The method of claim 3, wherein administering comprises oral consumption.

26. The method of claim 3, wherein the formulation comprises a ganglioside supplemented liquid or food.

27. The method of claim 26, wherein the formulation is a supplemented liquid comprising about 0.01 to about 1000 ppm ganglioside.

28. The method of claim 26 wherein the formulation comprises milk having a fat fraction of from about 1 to about 4% by weight, wherein the fat fraction comprises from about 0.1% to about 2.0% by weight ganglioside.

29. The method of claim 3 wherein inflammatory bowel disease comprises Crohn's disease or ulcerative colitis.

* * * * *